United States Patent
Ohtsuka et al.

(10) Patent No.: US 6,372,735 B1
(45) Date of Patent: Apr. 16, 2002

(54) TRICYCLIC TRIAZOLOBENZAZEPINE DERIVATIVES, PROCESS FOR PRODUCING THE SAME, AND ANTIALLERGIC

(75) Inventors: Yasuo Ohtsuka; Toshio Nishizuka; Sohjiro Shiokawa; Seiji Tsutsumi; Mami Kawaguchi; Hideo Kitagawa; Hiromi Takata; Takashi Shishikura; Toyoaki Ishikura; Kenichi Fushihara, all of Yokohama; Yumiko Okada, Odawara; Sachiko Miyamoto, Odawara; Maki Shiobara, Odawara, all of (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/509,494

(22) PCT Filed: Sep. 29, 1998

(86) PCT No.: PCT/JP98/04363

§ 371 Date: Mar. 29, 2000

§ 102(e) Date: Mar. 29, 2000

(87) PCT Pub. No.: WO99/16770

PCT Pub. Date: Apr. 8, 1999

(30) Foreign Application Priority Data

Sep. 29, 1997 (JP) .............................. 9-264611
Mar. 4, 1998 (JP) ........................... 10-052063

(51) Int. Cl.[7] ...................... A61K 31/55; A61K 31/675; A61P 37/08; C07D 223/10; C07D 487/00

(52) U.S. Cl. ................... 514/212.06; 514/81; 540/487; 540/521

(58) Field of Search .............................. 514/81, 212.06; 540/487, 521

(56) References Cited

U.S. PATENT DOCUMENTS 5,686,442 A    11/1997   Ohtsuka et al. ............. 514/211

FOREIGN PATENT DOCUMENTS

WO            97/00258         1/1997

OTHER PUBLICATIONS

Obrecht, Daniel et al., "A Novel and Efficient Approach for the Combinatorial Synthesis of Structurally Diverse Pyrimidines on Solid Support", Helvetica Chimica ACTA—vol. 80 (1997), pp. 65–72.

*Primary Examiner*—Brenda Coleman
(74) *Attorney, Agent, or Firm*—Wenderoth, Lind & Ponack, L.L.P.

(57) ABSTRACT

Tricyclic triazolobenzazepine derivatives in the form or a prodrug are provided. The compounds according to the present invention are those represented by formula (I) and pharmacologically acceptable salts and solvates thereof. The compounds are useful as antiallergic agents and exhibit excellent bioavailability.

(I)

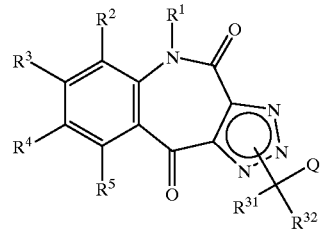

wherein $R^1$ represents hydrogen, OH, alkyl or phenyl alkyl,
$R^2$, $R^3$, $R^4$, and $R^5$ represent hydrogen, halogen, optionally protected hydroxyl, formyl, optionally substituted alkyl, alkenyl, alkoxy or the like, and Q represents a group selected from the following groups (i) to (iv), halogen, or alkoxy:

(i)

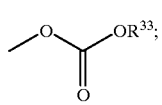

(ii)

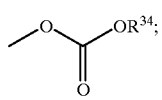

(iii)

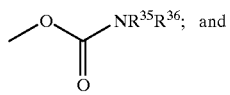

(iv)

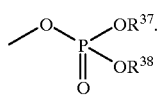

10 Claims, No Drawings

TRICYCLIC TRIAZOLOBENZAZEPINE DERIVATIVES, PROCESS FOR PRODUCING THE SAME, AND ANTIALLERGIC

This application is a national stage entry under 35 U.S.C. § 371 of PCT/JP98/04363, filed Sep. 29, 1998.

BACKGROUND OF THE INVENTION

1. Field of the Invention

The present invention relates to a tricyclic triazolobenzazepine derivative having antiallergic activity as a prodrug, an intermediate for synthesizing the same, a process for producing the same, and an antiallergic agent.

2. Background Art

In recent years, it has been revealed that allergic reactions induced by various stimuli such as immunoreactions can be divided into two reactions, i.e., an immediate reaction which occurs immediately after the stimulation and a delayed reaction which occurs several hours after the stimulation (see, for example, "Laie Asthmatic Responses", P. M. O'byrne, J. Dolovich and F. E. Hargreave, Am. Rev. Respir. Dis., 1987; 136: 740–751). Especially, the control of the latter reaction has become important.

Clinical studies show that there are few drugs which are significantly effective in inhibiting the delayed allergic reaction. Thus, the development of drugs therapeutically effective in treating both the immediate reaction and the delayed reaction has been expected in the art.

Sodium cromoglicate has been known as a representative drug for inhibiting the immediate and delayed allergic reactions. This drug is clinically administered by inhalation because it is not useful when orally administered.

The administration by inhalation, however, is disadvantageous in that it is difficult to properly administer the drug to babies, infants, and children and that it is difficult to continuously administer the drug to patients who are highly sensitive to inhalation stimuli.

Thus the development of oral drugs which can inhibit both the immediate and delayed allergic reactions and have excellent efficacy have been expected in the art.

In recent years, many studies on antiallergic agents and therapeutic agents for asthma have been conducted in the art. Tricyclic compounds containing seven membered ring which have been studied include dibenzoxepine derivatives (Japanese Patent Laid-Open Nos. 10784/1988 and 78292/1993 and Journal of Chemical & Pharmaceutical Bulletin, vol. 39, No. 10, p. 2724 and p. 2729 (1991)), dibenzoxazepine derivatives (Japanese Patent Laid-Open Nos. 184963/1991, 211071/1992, and 65257/1993 and EP 5180720), and dibenzocycloheptene derivatives (WO 93/13068). Further, tricyclic benzazepine derivatives and tricyclic benzothiazepine derivatives are disclosed in EP 0686636, WO 95/18130, and WO 97/00258.

Meanwhile, a prodrug technique has been known as one means for improving the bioavailability of a drug (Keiko Toyo Seizai No Sekkei To Hyoka (Design and Assay of Oral Preparation): edited by Mitsuru Hashida, Yakugyo Jiho Co., Ltd., pp. 216–231 (1995)). Chemical modification of a carboxyl, hydroxyl, amino or other group of the drug through an ester, amido, acetal or other bond can improve the bioavailability of the drug. However, any 1,2,3-triazole-modified prodrug has not been reported in the art.

SUMMARY OF THE INVENTION

The present inventors have synthesized a tricyclic triazolobenzazepine derivative having a chemically modified triazole ring and have found that the derivative has superior bioavailability compared with the corresponding triazolobenzazepine.

In one aspect of the present invention, there are provided tricyclic triazolobenzazepine derivatives as a prodrug represented by formula (I) and pharmacologically acceptable salts and solvates thereof:

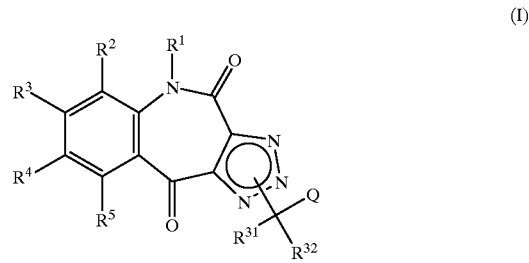

(I)

wherein $R^1$ represents a hydrogen atom, a hydroxyl group, $C_{1-4}$ alkyl, or phenyl $C_{1-4}$ alkyl;

$R^2$, $R^3$, $R^4$, and $R^5$, which may be the same or different, represent any one of the following (a) to (n):
  (a) a hydrogen atom;
  (b) a halogen atom;
  (c) an optionally protected hydroxyl group;
  (d) formyl;
  (e) $C_{1-12}$ alkyl which may be substituted by a halogen atom;
  (f) $C_{2-12}$ alkenyl which has one or more carbon—carbon double bonds and may be substituted by
    (1) a halogen atom,
    (2) cyano,
    (3) —$COR^9$ wherein $R^9$ represents a hydrogen atom or $C_{1-6}$ alkyl,
    (4) —$COOR^{10}$ wherein $R^{10}$ represents a hydrogen atom or $C_{1-6}$ alkyl,
    (5) —$CONR^{11}R^{12}$ wherein $R^{11}$ and $R^{12}$, which may be the same or different, represent
      (i) a hydrogen atom,
      (ii) $C_{1-6}$ alkyl which may be substituted by amino optionally substituted by $C_{10-4}$ alkyl, phenyl optionally substituted by $C_{1-4}$ alkyl which may be substituted by a saturated five- to seven-membered heterocyclic ring containing one or two nitrogen atoms (the nitrogen atoms may be substituted by $C_{1-4}$ alkyl), or a saturated or unsaturated five- to seven-membered heterocyclic ring,
      (iii) phenyl which may be substituted by carboxyl, or
      (iv) a saturated or unsaturated five to seven-membered heterocyclic ring,
    (6) a saturated or unsaturated five- to seven-membered heterocyclic ring which may be substituted by $C_{1-4}$ alkyl or may form a bicyclic ring fused with another ring;
  (g) $C_{1-12}$ alkoxy which may be substituted by
    (1) a halogen atom,
    (2) a hydroxyl group,
    (3) cyano,
    (4) $C_{3-7}$ cycloalkyl,
    (5) phenyl,
    (6) $C_{1-4}$ alkoxy,
    (7) phenoxy, (8) amino which may be substituted by $C_{1-4}$ alkyl,
(9) —$COR^{13}$ wherein $R^{13}$ represents a hydrogen atom, $C_{1-6}$ alkyl, phenyl optionally substituted by a halogen atom or $C_{1-4}$ alkoxy, or phenyl $C_{1-4}$ alkyl,
(10) —$COOR^{14}$ wherein $R^{14}$ represents a hydrogen atom or $C_{1-6}$ alkyl,
(11) —$CONR^{15}R^{16}$ wherein $R^{15}$ and $R^{16}$, which may be the same or different, represent a hydrogen atom or $C_{1-6}$ alkyl which may be substituted by a saturated or unsaturated five- to seven-membered heterocyclic ring, or
(12) a saturated or unsaturated five- to seven-membered heterocyclic ring which may be substituted by $C_{1-4}$ alkyl or phenyl $C_{1-4}$ alkyl;
(h) —C=N—$OR^{16}$ wherein $R^{16}$ represents a hydrogen atom, $C_{1-6}$ alkyl, phenyl $C_{1-4}$ alkyl, or phenyl;
(i) —$(CH_2)mOR^{17}$ wherein m is an integer of 1 to 4, and $R^{17}$ represents a hydrogen atom, $C_{1-6}$ alkyl, or phenyl $C_{1-4}$ alkyl of which one or more hydrogen atoms on the benzene ring may be substituted by $C_{1-4}$ alkyl;
(j) —$(CH_2)k$—$COR^{18}$ wherein k is an integer of 1 to 4, and $R^{18}$ represents a hydrogen atom or $C_{1-4}$ alkyl;
(k) —$(CH_2)j$—$COOR^{19}$ wherein j is an integer of 0 to 4, and $R^{19}$ represents a hydrogen atom or $C_{1-6}$ alkyl;
(l) —$(CH_2)p$—$NR^{20}R^{21}$ wherein p is an integer of 1 to 4, and $R^{20}$ and $R^{21}$, which may be the same or different, represent
  (1) a hydrogen atom,
  (2) $C_{1-6}$ alkyl which may be substituted by amino optionally substituted by $C_{1-4}$ alkyl,
  (3) phenyl $C_{1-4}$ alkyl,
  (4) —$COR^{22}$ wherein $R^{22}$ represents a hydrogen atom or $C_{1-4}$ alkyl which may be substituted by carboxyl, or
  (5) —$SO_2R^{23}$ wherein $R^{23}$ represents $C_{1-4}$ alkyl or phenyl which may be substituted by a halogen atom;
(m) —$(CH_2)q$—$CONR^{24}R^{25}$ wherein q is an integer of 0 to 4, and $R^{24}$ and $R^{25}$, which may be the same or different, represent a hydrogen atom, a saturated or unsaturated five- to seven-membered heterocyclic ring, or $C_{1-6}$ alkyl which may be substituted by a saturated or unsaturated five- to seven-membered heterocyclic ring, or alternatively $R^{24}$ and $R^{25}$ may form a saturated or unsaturated five- to seven-membered heterocyclic ring together with a nitrogen atom to which they are attached (the heterocyclic ring may further contain at least one oxygen, nitrogen, or sulfur atom, may form a bicyclic ring fused with another ring, or may be substituted by $C_{1-4}$ alkyl); and
(n) —$NR^{26}R^{27}$ wherein $R^{26}$ and $R^{27}$, which may be the same or different, represent a hydrogen atom or —$COR^{28}$ wherein $R^{28}$ represents a hydrogen atom, $C_{1-6}$ alkyl, or phenyl which may be substituted by $C_{1-4}$ alkyl or $C_{1-6}$ alkoxy optionally substituted by phenyl;

$R^{31}$ and $R^{32}$, which may be the same or different, represent a hydrogen atom or $C_{1-6}$ alkyl which may be substituted by a halogen atom; and Q represents a group selected from the following groups (i) to (iv) or a halogen atom or $C_{1-6}$ alkoxy:

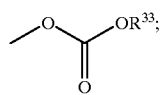

(i)

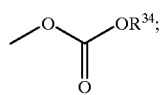

(ii)

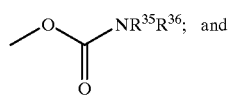

(iii)

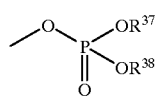

(iv)

wherein $R^{33}$ represents
  $C_{1-6}$ alkyl which may be substituted by $C_{1-6}$ alkoxy optionally substituted by $C_{1-6}$ alkoxy, phenyl optionally substituted by $C_{1-6}$ alkoxy, amino, or nitro, or a saturated or unsaturated five- to seven-membered heterocyclic ring optionally substituted by $C_{1-6}$ alkoxy, amino, or nitro,
  phenyl which may be substituted by $C_{1-6}$ alkoxy, amino, or nitro, or
  a saturated or unsaturated five- to seven-membered heterocyclic ring which may be substituted by $C_{1-6}$ alkoxy, amino, or nitro, or $R^{33}$ may form $C_{1-4}$ alkylene together with $R^{31}$ or $R^{32}$, $R^{34}$ represents
  $C_{1-6}$ alkyl which may be substituted by a halogen atom, carboxyl, phenyl optionally substituted by $C_{1-6}$ alkoxy, amino, or nitro, or a saturated or unsaturated five- to seven-membered heterocyclic ring optionally substituted by $C_{1-6}$ alkoxy, amino, or nitro,
  phenyl which may be substituted by $C_{1-6}$ alkoxy, amino, or nitro, or
  a saturated or unsaturated five- to seven-membered heterocyclic ring which may be substituted by $C_{1-6}$ alkoxy, amino, or nitro, $R^{35}$ and $R^{36}$, which may be the same or different, represent a hydrogen atom or $C_{1-6}$ alkyl which may be substituted by amino optionally substituted by $C_{1-4}$ alkyl or $R^{35}$ and $R^{36}$ may form a saturated or unsaturated five- to seven-membered heterocyclic ring together with a nitrogen atom to which they are attached, and $R^{37}$ and $R^{38}$, which may be the same or different, represent $C_{1-6}$ alkyl.

In another aspect of the present invention, there are provided tricyclic benzazepine derivatives as a prodrug represented by formula (Ia) and pharmacologically acceptable salts and solvates thereof:

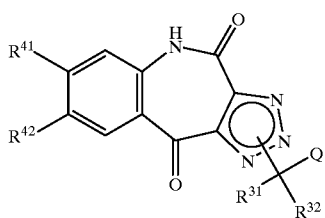

(Ia)

wherein $R^{41}$ and $R^{42}$, which may be the same or different, represent a hydrogen atom, optionally protected hydroxyl, $C_{1-6}$ alkoxy which may be substituted by a halogen atom, or $C_{1-6}$ alkyl which may be substituted by a halogen atom and $R^{31}$, $R^{32}$, and Q are as defined above.

The tricyclic triazolobenzazepine derivatives according to the present invention are useful for the treatment of allergic diseases.

In another aspect of the present invention, there is provided a pharmaceutical composition comprising as an active ingredient the compound represented by formula (I) or (Ia) or a pharmacologically acceptable salt or a solvate thereof.

In a further aspect of the present invention, there are provided intermediates for synthesizing the compounds represented by formulae (I) and (Ia).

Specifically, an intermediate according to the present invention is a compound represented by formula (II) or a salt or solvate thereof:

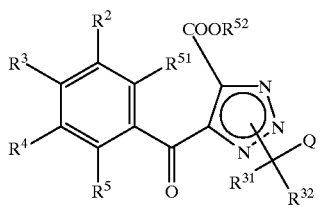

(II)

wherein $R^{51}$ represents nitro or amino, $R^{52}$ represents a hydrogen atom or a protective group for carboxyl, and Q, $R^2$ to $R^5$, $R^{31}$, and $R^{32}$ are as defined above.

Another intermediate according to the present invention is a compound represented by formula (II') or a salt or solvate thereof:

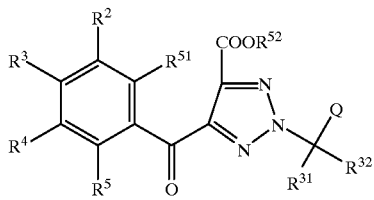

(II')

wherein Q, $R^2$ to $R^5$, $R^{31}$, $R^{32}$, $R^{51}$, and $R^{52}$ are as defined above.

A further intermediate according to the present invention is a compound represented by formula (VI) or a salt or solvate thereof:

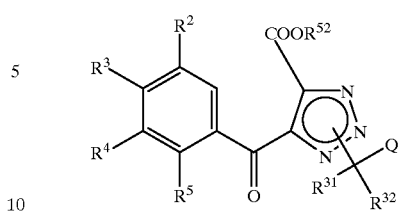

(VI)

wherein Q, $R^2$ to $R^5$, $R^{31}$, $R^{32}$, and $R^{52}$ are as defined above.

A further intermediate according to the present invention is a compound represented by formula (VI') or a salt or solvate thereof:

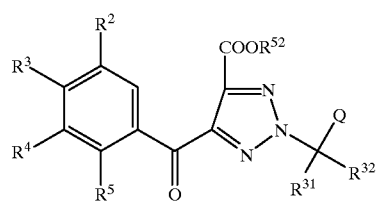

(VI')

wherein Q, $R^2$ to $R^5$, $R^{31}$, $R^{32}$, and $R^{52}$ are as defined above.

A further intermediate according to the present invention is a compound represented by formula (VII) or a salt or solvate thereof:

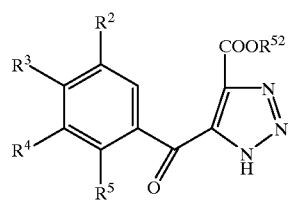

(VII)

wherein $R^2$ to $R^5$, and $R^{52}$ are as defined above.

A further intermediate according to the present invention is a compound represented by formula (VIII) or a salt or solvate thereof:

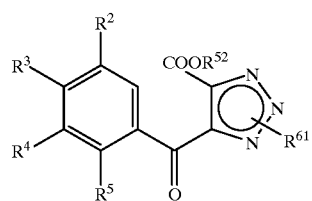

(VIII)

wherein $R^{61}$ represents a protective group for triazole and $R^2$ to $R^5$, and $R^{52}$ are as defined above.

A further intermediate according to the present invention is a compound represented by formula (IXa) or a salt or solvate thereof:

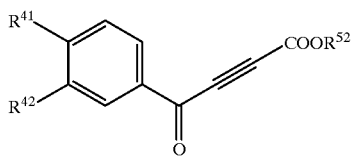

(IXa)

wherein $R^{41}$ to $R^{42}$, and $R^{52}$ are as defined above, provided that $R^{41}$ and/or $R^{42}$ do not represent a hydrogen atom.

A further intermediate according to the present invention is a compound represented by formula (XVIa) or a salt or solvate thereof:

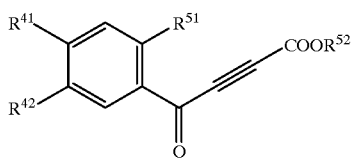

(XVIa)

wherein $R^{41}$ to $R^{42}$, $R^{51}$, and $R^{52}$ are as defined above.

These intermediates are useful in producing the compound s represented by formulae (I) and (Ia).

DETAILED DESCRIPTION OF THE INVENTION

Definition

As used herein, the term "alkyl" or "alkoxy" as a group or a part of a group means straight-chain, branched, or cyclic alkyl or alkoxy.

$C_{1-6}$ alkyls as used herein include straight-chain alkyls such as methyl, ethyl, n-propyl, n-butyl, n-pentyl, and n-hexyl, branched alkyls, such as isopropyl, isobutyl, tert-butyl, and 3-pentyl, and cyclic alkyls, such as cyclopropyl, cyclobutyl, cyclopentyl, and cyclohexyl.

$C_{1-6}$ alkoxys as used herein include straight-chain alkoxys having 1 to 6 carbon atoms, such as methoxy, ethoxy, n-propoxy, n-butoxy, n-pentyloxy, and n-hexyloxy, branched alkoxys, such as isopropyloxy, isobutyloxy, and tert-butyloxy, and cyclic alkoxys, such as cyclopropyloxy and cyclohexyloxy.

$C_{1-6}$ alkyls as used herein include, in addition to the above $C_{1-6}$ alkyls, alkyls having 7 to 16 carbon atoms, such as 1-methylhexyl, 5-methylhexyl, heptyl, octyl, nonyl, decyl, undecyl, and pentadecyl.

The term "halogen atom" as used herein means a fluorine, chlorine, bromine, or iodine atom.

The term "dissimilar atom" as used herein means an oxygen, nitrogen, or sulfur atom.

The term "saturated or unsaturated five- to seven-membered heterocyclic ring" as used herein means a heterocycle containing one or more heteroatoms selected from oxygen, nitrogen, and sulfur atoms. Examples of heterocyclic rings include pyridine, imidazole, oxazole, thiazole, pyrimidine, furan, thiophene, pyrrole, pyrrolidine, piperidine, tetrahydrofuran, and oxazoline.

Compounds

In formula (I), $R^2$, $R^3$, $R^4$, and $R^5$ each independently represent any one of groups (a) to (n).

Examples of protective groups for the hydroxyl group (c) include acetyl, chloroacetyl, dichloroacetyl, trichloroacetyl, benzoyl, 4-nitrobenzoyl, 3-oxobutyryl, benzyl, diphenylmethyl, triphenylmethyl, 4-methoxybenzyl, 3,4-dimethoxybenzyl, methoxymethyl, methoxyethoxymethyl, benzyloxymethyl, trimethylsilyl, tert-butyldimethylsilyl, triphenylsilyl, 2-tetrahydropyranyl, and trimethylsilylethoxymethoxy.

(e) $C_{1-12}$ alkyl is preferably $C_{1-6}$ alkyl, more preferably $C_{1-4}$ alkyl.

(f) $C_{2-12}$ alkenyl is preferably $C_{2-6}$ alkenyl, more preferably $C_{2-4}$ alkenyl, most preferably vinyl.

At least one hydrogen atom on the alkenyl may be substituted by (1) a halogen atom, (2) cyano, (3) —$COR^9$, (4) —$COOR^{10}$, (5) —$CONR^{11}R^{12}$, or (6) a saturated or unsaturated five- to seven-membered heterocyclic ring.

In (5) —$CONR^{11}R^{12}$, $R^{11}$ and $R^{12}$, which may be the same or different, represent a hydrogen atom or $C_{1-6}$ alkyl (preferably $C_{1-4}$ alkyl), phenyl, or a saturated or unsaturated five- to seven-membered heterocyclic ring.

In this case, this alkyl may be further substituted by amino, phenyl, or a saturated or unsaturated five- to seven-membered heterocyclic ring.

Further, one or two hydrogen atoms on this amino may be substituted by $C_{1-4}$ alkyl.

This phenyl may also be substituted by $C_{1-4}$ alkyl. In this case, this $C_{1-4}$ alkyl may be substituted by a saturated five- to seven-membered heterocyclic ring containing one or two nitrogen atoms optionally substituted by $C_{1-4}$ alkyl. Preferred examples thereof include piperidino, 4-piperidyl, 1-pyrrolidinyl, piperazinyl, 4-$C_{1-4}$ alkylpiperazinyl, and morpholino.

(g) $C_{1-12}$ alkoxy is preferably $C_{1-6}$ alkoxy, more preferably $C_{1-4}$ alkoxy.

This alkoxy may be substituted by (9) —$COR^{13}$ wherein $R^{13}$ represents a hydrogen atom, $C_{1-6}$ alkyl (preferably $C_{1-4}$ alkyl), phenyl, or phenyl $C_{1-4}$ alkyl. In this case, this phenyl may be substituted by a halogen atom or $C_{1-4}$ alkoxy. Although the position of the substituent is not particularly limited, the 2- or 4-position on the phenyl ring is preferred.

(g) $C_{1-12}$ alkoxy may be substituted by a saturated or unsaturated five- to seven-membered heterocyclic ring as substituent (12). This heterocyclic ring is preferably a five- or six-membered heterocyclic saturated ring containing one or two nitrogen atoms, for example, piperidino, 4-piperidinyl, 1-pyrrolidinyl, piperazinyl, and morpholino. One or more hydrogen atoms on the heterocyclic ring may be further substituted by $C_{1-4}$ alkyl or phenyl $C_{1-4}$ alkyl. Preferred examples of phenyl $C_{1-4}$ alkyls include benzyls, such as benzyl, 4-methylbenzyl, 4-chlorobenzyl, 4-hydroxybenzyl, 4-nitrobenzyl, 4-methoxybenzyl, and 4-carboxybenzyl, phenethyl, 3-phenylpropyl, and 4-phenylbutyl.

In (i) —$(CH_2)mOR^{17}$, is an integer of 1 to 4, preferably an integer of 1 or 2.

In (j) —$(CH_2)kCOR^{18}$, k is an integer of 0 to 4, preferably 0, 1, or 2.

In (k) —$(CH_2)jCOOR^{19}$, j is an integer of 0 to 4, preferably 0, 1, or 2.

In (m) —$(CH_2)qCONR^{24}R^{25}$, q is an integer of 0 to 4, preferably 0, 1, or 2.

$R^{24}$ and $R^{25}$ may form a saturated or unsaturated five- to seven-membered heterocyclic ring together with a nitrogen atom to which they are attached. This heterocyclic ring may further contain one or more oxygen, nitrogen, or sulfur atoms. The heterocyclic ring may be substituted by $C_{1-4}$ alkyl. Preferred examples of heterocyclic ring include piperazino, piperidino, N-methylpiperazino, morpholino, succinimide, indolyl, 4-methylindolyl, 5-methylindolyl, isoindolyl, phthalimido, 4-methylphthalimido, and 1,1-dioxo-2-benzothiazolyl.

In formulae (I) and (Ia), Q may represent a halogen atom, $C_{1-6}$ alkoxy (preferably $C_{1-4}$ alkoxy), or any one of groups (i) to (iv).

In group (i), one or more hydrogen atoms on this $C_{1-6}$ alkyl represented by $R^{33}$ may be substituted by $C_{1-6}$ alkoxy, phenyl, or a saturated or unsaturated five- to seven-membered heterocyclic ring (preferably a six-membered heterocycle containing one hetero atom). Further, one or more hydrogen atoms on this $C_{1-6}$ alkoxy may be substituted by $C_{1-6}$ alkoxy. One or more hydrogen atoms on this phenyl and the heterocyclic ring may be substituted by $C_{1-6}$ alkoxy, amino, or nitro.

Preferred examples of $C_{1-6}$ alkyls represented by $R^{33}$ include methyl, ethyl, n-propyl, n-butyl, n-pentyl, n-hexyl, isopropyl, isobutyl, tert-butyl, 3-pentyl, cyclopropyl, cyclobutyl, ,cyclopentyl, cyclohexyl, 1,3-diethoxy-2-propyl, 2-isopropoxyethyl, phenethyl, 3-pyridylmethyl, 4-methoxyphenethyl, and 2-(2-methoxyethoxy)ethoxy.

$R^{33}$ may represent phenyl. This phenyl may be substituted by $C_{1-6}$ alkoxy, amino, or nitro, preferably nitro. Preferred examples of phenyls represented by $R^{33}$ include 4-nitrophenyl.

Further, $R^{33}$ may represent a saturated or unsaturated five- to seven-membered heterocyclic ring (preferably a six-membered heterocycle containing one hetero atom). At least one hydrogen atom on the heterocyclic ring may be substituted by $C_{1-6}$ alkoxy, amino, or nitro, preferably nitro. Preferred examples of saturated or unsaturated five- to seven-membered heterocyclic ring represented by $R^{33}$ include 4-piperazyl, 4-piperidyl, and 4-tetrahydropyranyl.

Further, $R^{33}$ may form $C_{1-4}$ alkylene together with any one of $R^{31}$ and $R^{32}$. Preferred examples of $C_{1-4}$ alkylenes include methylene. When $R^{33}$ forms methylene together with $R^{31}$ or $R^{32}$ and $R^{31}$ or $R^{32}$ which is not bonded to $R^{33}$ represents a hydrogen atom, then —$CQR^{31}R^{32}$ represents 4-(2-oxo)-1,3-dioxolyl.

In group (ii), one or more hydrogen atoms on $C_{1-16}$ alkyl represented by $R^{34}$ may be substituted by a halogen atom, carboxyl, phenyl, or a saturated or unsaturated five- to seven-membered heterocyclic ring (preferably a six-membered heterocyclic ring containing one hetero atom). Further, one or more hydrogen atoms on the phenyl and the heterocycle may be substituted by $C_{1-6}$ alkoxy, amino, or nitro Preferred examples of $C_{1-16}$ alkyls represented by $R^{34}$ include methyl, ethyl, n-propyl, n-butyl, n-pentyl, n-hexyl, isopropyl, isobutyl, tert-butyl, 3-pentyl, cyclopropyl, cyclobutyl, cyclopentyl, cyclohexyl, 1-methylhexyl, 5-methylhexyl, heptyl, octyl, nonyl, decyl, undecyl, pentadecyl, chloromethyl, 3-chloropropyl, 2-carboxyethyl, morpholinomethyl, 4-methoxybenzyl, and 4-piperazinylmethyl.

$R^{34}$ may represent phenyl. The phenyl may be substituted by $C_{1-6}$ alkoxy, amino, or nitro, preferably amino. Preferred examples of phenyls represented by $R^{34}$ include 4-aminophenyl.

Further, $R^{34}$ may represent a saturated or unsaturated five- to seven-membered heterocyclic ring (preferably a six-membered heterocyclic ring containing one hetero atom). One or more hydrogen atoms on the heterocyclic ring may be substituted by $C_{1-6}$ alkoxy, amino, or nitro, preferably amino. Preferred examples of saturated or unsaturated five- to seven-membered heterocyclic rings represented by $R^{34}$ include 3-pyridyl and 4-pyridyl.

In group (iii), one or more hydrogen atoms on $C_{1-6}$ alkyl represented by $R^{35}$ and $R^{36}$ may be substituted by amino. Preferred examples of $C_{1-6}$ alkyls represented by $R^{35}$ and $R^{36}$ include 2-(N,N-dimethylamino) ethyl. Preferred examples of saturated or unsaturated five- to seven-membered heterocyclic rings formed by combining $R^{35}$ with $R^{36}$ include 1-morpholino, 1-imidazolyl, and 4-piperazinyl.

A group of preferred compounds represented by formula (I) include:
a group of compounds wherein $R^1$, $R^2$, $R^3$, $R^4$, and $R^5$ represent a hydrogen atom or (g) $C_{1-12}$ alkoxy (preferably $C_{1-6}$ alkoxy) and Q represents group (i) (preferably $R^{33}$ represents $C_{1-4}$ alkyl optionally substituted by $C_{1-4}$ alkoxy);

a group of compounds wherein $R^1$ represents a hydrogen atom, $R^2$, $R^3$, $R^4$, and $R^5$ represent a hydrogen atom or (g) $C_{1-12}$ alkoxy (preferably $C_{1-6}$ alkoxy), and Q represents group (i) (preferably, $R^{33}$ represents $C_{1-4}$ alkyl optionally substituted by $C_{1-4}$ alkoxy);

a group of compounds wherein $R^1$, $R^2$, and $R^5$ represents a hydrogen atom, $R^3$ and $R^4$ represent a hydrogen atom or (g) $C_{1-12}$ alkoxy (preferably $C_{1-6}$ alkoxy), and Q represents group (i) (preferably, $R^{33}$ represents $C_{1-4}$ alkyl optionally substituted by $C_{1-4}$ alkoxy);

a group of compounds wherein $R^1$, $R^2$, and $R^5$ represent a hydrogen atom, $R^3$ and $R^4$ represent a hydrogen atom or (f) $C_{2-12}$ alkenyl, and Q represents group (i) (preferably, $R^{33}$ represents $C_{1-4}$ alkyl optionally substituted by $C_{1-4}$ alkoxy);

a group of compounds wherein $R^1$, $R^2$, and $R^5$ represent a hydrogen atom, $R^3$ and $R^4$ represent a hydrogen atom or (e) $C_{1-12}$ alkyl, and Q represents group (i) (preferably, $R^{33}$ represents $C_{1-4}$ alkyl optionally substituted by $C_{1-4}$ alkoxy);

a group of compounds wherein $R^1$, $R^2$, and $R^5$ represent a hydrogen atom, $R^3$ and $R^4$ represent a hydrogen atom, or (j) group —$(CH_2)kCOR^{18}$, (l) —$(CH_2)pNR^{20}R^{21}$, (m) —$(CH_2)qCONR^{22}R^{23}$, or (n) —$NR^{29}R^{30}$, and Q represents group (i) (preferably, $R^{33}$ represents $C_{1-4}$ alkyl optionally substituted by $C_{1-4}$ alkoxy);

a group of compounds wherein $R^1$, $R^2$, $R^4$, and $R^5$ represent a hydrogen atom, $R^3$ represents (g) $C_{1-12}$ alkoxy (preferably $C_{1-6}$ alkoxy), and Q represents group (i) (preferably, $R^{33}$ represents $C_{1-4}$ alkyl optionally substituted by $C_{1-4}$ alkoxy); and a group of compounds wherein $R^1$, $R^2$, $R^3$, and $R^5$ represent a hydrogen atom, $R^4$ represents (g) $C_{1-12}$ alkoxy (preferably, $C_{1-6}$ alkoxy), and Q represents group (i) (preferably, $R^{33}$ represents $C_{1-4}$ alkyl optionally substituted by $C_{1-4}$ alkoxy).

In formulae (I) and (Ia), —$CR^{31}R^{32}Q$ is preferably located at the 2-position in the triazole ring.

One or more hydrogen atoms on $C_{1-6}$ alkyl represented by $R^{31}$ and $R^{32}$ in formulae (I) and (Ia) and one or more hydrogen atoms on the $C_{1-6}$ alkyl and the $C_{1-6}$ alkoxy in its alkyl portion represented by $R^{41}$ and $R^{42}$ in formula (Ia) may be substituted by a halogen atom. Examples of the substituted alkyls and alkyl portions include trifluoromethyl, 2-fluoroethyl, difluoromethyl, 2,2,2-trifluoroethyl, trichloromethyl, 2-chloroethyl, dichloromethyl, 2,2,2-trichloroethyl, tribromomethyl, 2-bromoethyl, dibromomethyl, 2,2,2-tribromoethyl, pentafluoroethyl, fluoromethyl, 3,3,3-trifluoropropyl, 4,4,4-trichlorobutyl, 5,5,5-trifluoropentyl, and 6,6,6-trifluorohexyl.

Protective groups for optionally protected hydroxyl which may be represented by $R^{41}$ and $R^{42}$ include acetyl, chloroacetyl, dichloroacetyl, trichloroacetyl, benzoyl, 4-nitrobenzoyl, 3-oxobutyryl, benzyl, diphenylmethyl, triphenylmethyl, 4-methoxybenzyl, 3,4-dimethoxybenzyl, methoxymethyl, methoxyethoxymethyl, benzyloxymethyl, trimethylsilyl, tert-butyldimethylsilyl, triphenylsilyl, 2-tetrahydropyranyl, and trimethylsilylethoxymethoxy.

$R^{41}$ and $R^{42}$ represent preferably $C_{1-4}$ alkoxy, more preferably methoxy or isopropyloxy. Still more preferably, $R^{41}$ represents methoxy, and $R^{42}$ represents methoxy or isopropyloxy.

A group of preferred compounds represented by formula (Ia) include a group of compounds wherein $R^{41}$ and $R^{42}$ represent $C_{1-6}$ alkoxy (preferably $C_{1-4}$ alkoxy, more preferably methoxy or isopropyloxy), and Q represents group (i) (preferably, $R^{33}$ represents optionally $C_{1-4}$ alkoxy-substituted $C_{1-4}$ alkyl).

Among the compounds according to the present invention, particularly preferred compounds include 2-(1-isopropoxycarbonyloxy-2-methylpropyl)-7,8-dimethoxy-4 (5H),10-dioxo-2H-1,2,3-triazolo[4,5-c][1]benzazepine, 2-(1-(1,3-diethoxy-2-propoxycarbonyloxy)-2-methylpropyl)-7,8-dimethoxy-4 (5H), 10-dioxo-2H-1,2,3-triazolo[4,5-c][1]benzazepine, 2-(1-(1,3-diethoxy-2-propoxycarbonyloxy)-2-methylpropyl)-8-isopropoxy-7-methoxy-4 (5H),10-dioxo-2H-1,2,3-triazolo[4,5-c][1]benzazepine, and 8-isopropoxy-2-(1-isopropoxycarbonyloxy-2-methylpropyl)-7-methoxy-4 (5H) 10-dioxo-2H-1,2,3-triazolo[4,5-c][1]benzazepine.

In the present invention, protective groups for carboxyl represented by $R^{52}$ include, for example, methyl, ethyl, tert-butyl, benzyl, 4-methoxybenzyl, diphenylmethyl, 4-nitrobenzyl, tert-butyldimethylsilyl, triphenylsilyl, 2-phenylsulfonylethyl, 2-methoxycarbonylethyl, 2-cyanoethyl, and 2-trimethylsilylethyl.

In the present invention, "protective groups for triazole" represented by $R^{61}$ include, for example, benzyl optionally substituted by a halogen atom, hydroxyl, nitro, $C_{1-6}$ alkyl, or $C_{1-6}$ alkoxy, diphenylmethyl, triphenylmethyl, 4-methoxybenzyl, 3,4-dimethoxybenzyl, 3,4,5-trimethoxybenzyl, trimethylsilyl, tert-butyldimethylsilyl, methoxymethyl, benzyloxymethyl, and methoxyethoxy.

A group of preferred intermediate compounds represented by formulae (II), (II'), (VI), and (VI') include compounds wherein, $R^2$ and $R^5$ represent a hydrogen atom, $R^3$ and $R^4$ each independently represent a hydrogen atom, optionally protected hydroxyl, optionally substituted $C_{1-6}$ alkoxy, optionally substituted $C_{1-6}$ alkyl (preferably, optionally substituted $C_{1-6}$ alkoxy), and Q represents group (i) (preferably, $R^{33}$ represents $C_{1-4}$ alkyl optionally substituted by $C_{1-4}$ alkoxy).

A group of preferred intermediate compounds represented by formulae (VII) and (VIII) include compounds wherein $R^2$ and $R^5$ represent a hydrogen atom and $R^3$ and $R^4$ each independently represent a hydrogen atom, optionally protected hydroxyl, optionally substituted $C_{1-6}$ alkoxy, and optionally substituted $C_{1-6}$ alkyl (preferably, optionally substituted $C_{1-6}$ alkoxy).

Preferred examples of compounds represented by formulae (VI) and (VI') include ethyl 5-(3,4-dimethoxybenzoyl)-2-(1-isopropoxycarbonyloxy-2-methylpropyl)-2H-1,2,3-triazole-4-carboxylate, ethyl 2-(1-isopropoxycarbonyloxy-2-methylpropyl)-5-(3-isopropoxy-4-methoxybenzoyl)-2H-1,2,3-triazole-4-carboxylate, ethyl 5-(3,4-dimethoxybenzoyl)-2-(1-(1,3-diethoxy-2-propoxy) carbonyloxy-2-methylpropyl)-2H-1,2,3-triazole-4-carboxylate, and ethyl 2-(1-(1,3-diethoxy-2-propoxy)carbonyloxy-2-methylpropyl)-5-(3-isopropoxy-4-methoxybenzoyl)-2H-1,2,3-triazole-4-carboxylate.

Examples of preferred compounds represented by formula (VII) include methyl 5-(3,4-dimethoxybenzoyl)-1H-1,2,3-triazole-4-carboxylate, ethyl 5-(3,4-dimethoxybenzoyl)-1H-1,2,3-triazole-4-carboxylate, methyl 5-(3-isopropoxy-4-methoxybenzoyl)-1H-1,2,3-triazole-4-carboxylate, and ethyl 5-(3-isopropoxy-4-methoxybenzoyl)-1H-1,2,3-triazole-4-carboxylate.

Examples of preferred compounds represented by formula (IX) include methyl 4-(3,4-dimethoxyphenyl)-4-oxo-2-butynoate, ethyl 4-(3,4-dimethoxyphenyl)-4-oxo-2-butynoate, methyl 4-(3-isopropoxy-4-methoxyphenyl)-4-oxo-2-butynoate, and ethyl 4-(3-isopropoxy-4-methoxyphenyl)-4-oxo-2-butynoate.

Examples of preferred compounds represented by formula (XVI) include ethyl 4-(4,5-dimethoxy-2-nitrophenyl)-4-oxo-2-butynoate and ethyl 4-(5-isopropoxy-4-methoxy-2-nitrophenyl)-4-oxo-2-butynoate.

In the compounds according to the present invention, tautomers and position isomers derived from triazole ring, cis-trans isomers derived from alkenyl as the substituent, and enantiomers derived from the group —$CQR^{33}R^{34}$ may exist, and any of the isomers and a mixture thereof fall within the scope of the present invention.

The compounds according to the present invention may be formed into pharmacologically acceptable salts thereof. Such salts include non-toxic salts. Preferred salts include alkali metal or alkaline earth metal salts, such as sodium, potassium, and calcium salts, hydrohalogenic acid salts, such as hydrofluoride salts, hydrochloride salts, hydrobromide salts, and hydroiodide salts, inorganic acid salts, such as nitric acid salts, perchloric acid salts, sulfuric acid salts, and phosphoric acid salts, lower alkylsulfonic acid salts, such as methanesulfonic acid salts, trifluoromethanesulfonic acid salts, and ethanesulfonic acid salts, arylsulfonic acid salts, such as benzenesulfonic acid salts and p-toluenesulfonic acid salts, organic acid salts, such as fumaric acid salts, succinic acid salts, citric acid salts, tartaric acid salts, oxalic acid salts, and maleic acid salts, and amino acid salts, such as glutamic acid salts and aspartic acid salts.

Solvates of the compounds according to the present invention include hydrates and ethanol solvates.

Production of compounds

The compounds according to the present invention may be synthesized by the following process 1 or 2.

<Process 1>

The compound represented by formula (I) may be produced by reacting a compound represented by formula (III)

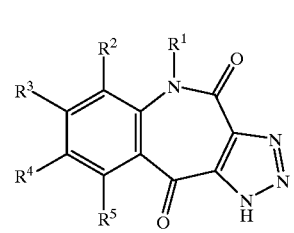

(III)

wherein $R^1$ to $R^5$ are as defined above, with a compound represented by formula (IV)

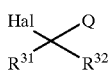

(IV)

wherein Q, $R^{31}$ and $R^{32}$ are as defined above and Hal represents a halogen atom, in a solvent which is not involved in the reaction (for example, water, ethanol, isopropyl alcohol, tetrahydrofuran, diisopropyl ether, methylene chloride, acetone, N,N-dimethylformamide, dimethylsulfoxide) in the presence of a base at a temperature of 0 to 150° C. for 1 to 48 hr. Bases as used herein include organic bases such as pyridine and triethylamine, and inorganic bases such as potassium carbonate, sodium carbonate, cesium carbonate, sodium hydrogencarbonate, sodium hydroxide, and potassium hydroxide. Preferably, the compound may be prepared by the reaction in N,N-dimethylformamide in the presence of sodium hydrogencarbonate at a reaction temperature of 20 to 100° C. for 1 to 24 hr. The compound represented by formula (I) is produced as a mixture of a 1-substituted triazole, a 2-substituted triazole, and a 3-substituted triazole in any ratio.

The compound represented by formula (III) may be produced by processes described, for example, in WO 95/18130 and WO 97/00258.

The compound represented by formula (I) may be purified by conventional purification methods, for example, recrystallization, reprecipitation, solvent extraction, column chromatography on silica gel, or column chromatography on adsorptive resin.

<Process 2>

The compound represented by formula (I) may be produced by reducing the compound of formula (IIa)

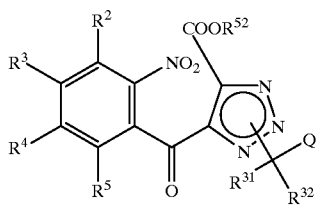

(IIa)

wherein Q, $R^2$ to $R^5$, $R^{31}$, $R^{32}$, and $R^{52}$ are as defined above, to prepare a compound represented by formula (IIb)

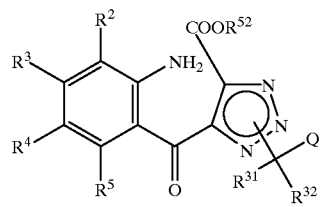

(IIb)

wherein Q, $R^2$ to $R^5$, $R^{31}$, $R^{32}$, and $R^{52}$ are as defined above, and then cyclizing the compound represented by formula (IIb).

Conventional catalytic reductions (preferably in the presence of a nickel or palladium catalyst in a solvent, for example, ethyl acetate, an alcohol solvent such as ethanol, water, or a mixture thereof) or reduction using a metal such as iron or zinc, for example, reduction in a zinc-acetic acid system, and the like may be used for the reduction reaction. The reduction may be carried out at a temperature of 10 to 100° C. for 0.1 to 10 hr.

The cyclization may be carried out by reacting the compound represented by formula (IIb) with a strong base such as sodium hydride, potassium hydride, sodium methoxide, sodium ethoxide, or potassium tert-butoxide, in a solvent which is not involved in the reaction (for example, an alcohol such as methanol, ethanol, or isopropyl alcohol, toluene, N,N-dimethylformamide, dimethylsulfoxide, dioxane, tetrahydrofuran, or a mixture of two or more of these solvents) at a temperature of 0 to 100° C. for 1 to 48 hr, generally 5 to 24 hr.

The cyclization reaction may also be carried out in an acetic acid or trifluoroacetic acid solvent by reacting the compound represented by formula (IIb) at a temperature of 20 to 100° C. for 1 to 24 hr.

After the cyclization, Q may be further converted to another substituent.

In both the above reduction and cyclization reactions, the position isomerization of the substituent on the triazole is not observed. When a compound represented by formula (IIa') is used alone, the compound represented by formula (I) is obtained as a single compound.

The compound represented by formula (I) may be purified by conventional purification methods, for example, recrystallization, reprecipitation, solvent extraction, column chromatography on silica gel, or column chromatography on adsorptive resin.

The compound represented by formula (IIa) may be synthesized according to the following scheme. In the scheme, M represents lithium, magnesium chloride, magnesium bromide, magnesium iodide, zinc bromide, zinc iodide, cadmium bromide, cadmium iodide, or copper, $R^{62}$ represents sodium, $C_{1-6}$ alkylsilyl (for example, trimethylsilyl), or $C_{1-6}$ alkyltin, and Q, Hal, $R^2$ to $R^5$, $R^{31}$, $R^{32}$, $R^{52}$, and $R^{61}$ are as described above.

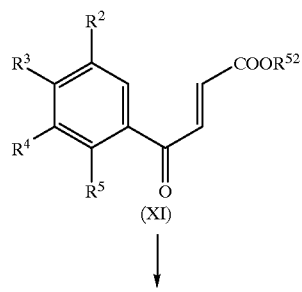

(XI)

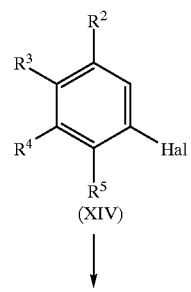

(XIV)

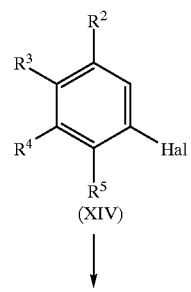

(XVII)

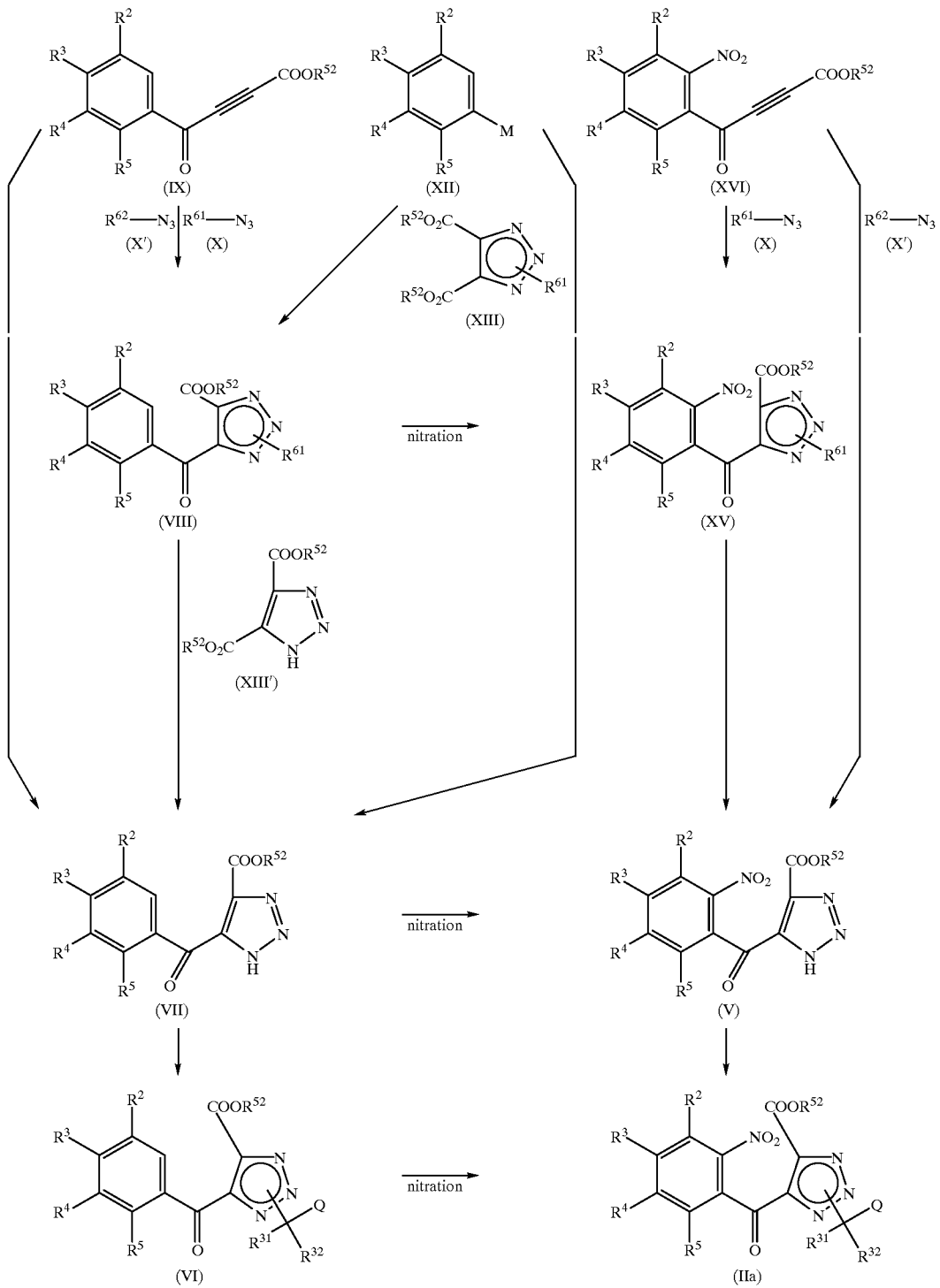

Synthesis (1) of compound of formula (IIa)

The compound represented by formula (IIa) may be produced from a compound represented by formula (V) by the following process A, B, C or D. According to the process B, C, or D, the compound represented by formula (IIa) having the substituent —CQR$^{31}$R$^{32}$ (represented by formula (IIa')) can be prepared, wherein the substituent is introduced into the triazole ring at its 2-position.

<Process A>

The compound represented by formula (IIa) may be prepared by reacting the compound represented by formula (V):

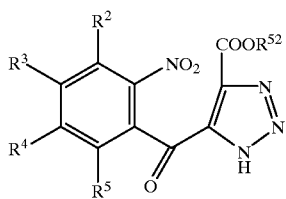

wherein Q, $R^2$ to $R^5$, and $R^{52}$ are as defined above, with the compound represented by formula (IV) according to process 1. As with the compound (I) prepared by process 1, the compound represented by formula (IIa) thus prepared is a mixture of three types of isomers. For example, the compound represented by formula (V) may be prepared in accordance with a process described in WO 95/18130.

<Process B>

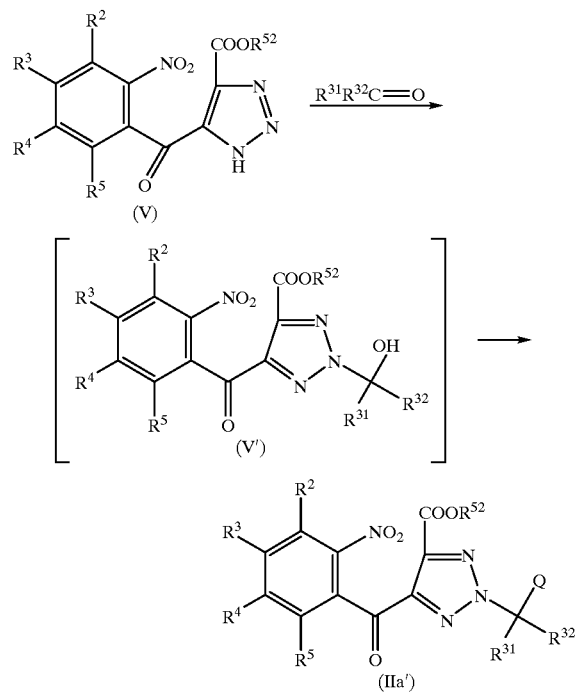

wherein Q, $R^2$ to $R^5$, $R^{31}$, $R^{32}$, and $R^{52}$ are as defined above.

The compound represented by formula (V) is reacted with a ketone or an aldehyde represented by $R^{31}R^{32}C=O$ in a solvent which is not involved in the reaction (for example, methylene chloride, ethyl acetate, or acetonitrile) at a temperature of −78 to 100° C., preferably −20 to 50° C. for 0.1 to 24 hr, generally 0.1 to 1 hr. In this case, a hemiacetal represented by the compound (V') is produced in the reaction system. This reaction is promoted by the addition of an acid catalyst. Preferred acid catalysts used herein include protonic acids such as p-toluenesulfonic acid, pyridinium salt of p-toluenesulfonic acid, D-(+)-camphorsulfonic acid, trifluoroacetic acid, sulfuric acid, hydrochloric acid, perchloric acid and phosphoric acid, and Lewis acids, such as boron trifluoride-diethyl ether complex, aluminum chloride, and titanium tetrachloride.

Q in formula (IIa') may be introduced by further adding various reactants to the compound represented by formula (V'). The compound represented by formula (IIa') wherein Q is any one of groups (i) to (iv), a halogen atom, or a $C_{1-6}$ alkoxy may be synthesized in accordance with the following.

(1) The compound represented by formula (IIa') wherein Q is group (i) may be prepared by reacting the reaction solution containing the compound represented by formula (V') with a compound represented by formula $R^{71}$-C(=O)—$R^{72}$ (wherein $R^{71}$ and $R^{72}$ each independently represent a chlorine atom, 4-nitrophenyl, or 1-imidazolyl) including 1,1'-carbonyldiimidazole, phosgene, p-nitrophenyl chloroformate, or bis (p-nitrophenyl) carbonate, optionally in the presence of a base such as pyridine, to prepare a compound represented by formula (IIa') wherein Q represents —$OCOR^{71}$ (wherein $R^{71}$ represents a chlorine atom, 4-nitrophenyl, or 1-imidazolyl) and then reacting the resulting compound with an alcohol represented by formula $R^{33}OH$ (wherein $R^{33}$ is as defined above) The substituent Q may be further converted to another substituent.

(2) The compound represented by formula (IIa') wherein Q represents group (ii) may be prepared by adding an acylating agent represented by $R^{34}COHal$ (wherein Hal and $R^{34}$ are as defined above) or $(R^{34}CO)_2O$ (wherein $R^{34}$ is as defined above) to the reaction solution containing the compound represented by formula (V'), optionally in the presence of a base such as pyridine.

The compound represented by formula (IIa') wherein Q represents group (ii) may also be prepared by fusing the compound represented by formula (V') with a compound represented by formula $R^{34}COOH$ (wherein $R^{34}$ is as defined above). Preferred condensing agents used herein include active esterifying agents such as dicyclohexylcarbodiimide, pyridine derivatives, and phosphoric acid derivatives, and dehydrating agents such as thionyl chloride and phosphorus oxychloride.

The compound may also be prepared by reacting the compound (IIa') (wherein the substituent Q represents a halogen atom, which may be synthesized by a process described in process (4), with a sodium or potassium salt of a carboxylic acid represented by formula $R^{34}COOH$ (wherein $R^{34}$ is as defined above) in a solvent which is not involved in the reaction in the presence of tetra-n-butylammonium bromide. Q may be further converted to another substituent.

(3) The compound represented by formula (IIa') wherein Q represents group (iii) may be prepared by reacting the compound, produced in process (1), represented by formula (IIa') (wherein $R^2$ to $R^5$, $R^{31}$, $R^{32}$, and $R^{52}$ are as defined above and Q represents —$OCOR^{71}$ (wherein $R^{71}$ is as defined above)), optionally after isolation, with an amine represented by $R^{35}R^{36}NH$ (wherein $R^{35}$ and $R^{36}$ are as defined above).

(4) The compound represented by formula (IIa'), wherein Q represents group (iv), a halogen atom, or $C_{1-6}$ alkoxy, may be prepared by adding a chlorophosphoric ester represented by $(R^{37}O)(R^{38}O)POCl$, an alcohol represented by $R^{73}OH$ (wherein $R^{73}$ represents $C_{1-6}$ alkyl), or a halogenating agent such as thionyl chloride or thionyl bromide, to the reaction solution containing the compound (V'). The reaction may be carried out generally at a temperature of −20 to 100° C. for 0.1 to 48 hr.

All the compounds represented by formula (IIa') synthesized by the process via the hemiacetal represented by the compound (V') are obtained as triazoles substituted at the 2-position.

<Process C>

The compound represented by formula (IIa'), wherein Q represents group (i), may be prepared by reacting the compound represented by formula (V) with a compound represented by $R^{31}R^{32}C=O$ (wherein $R^{31}$ and $R^{32}$ are as defined above) (for example, isobutyl aldehyde) in an organic solvent such as acetone, acetonitrile, or ethyl acetate, at a temperature of −20 to 100° C., preferably 22 to 28° C., to prepare a compound represented by formula (V') and then reacting the compound represented by formula (V') in the same solution with a compound represented by HalCOOR$^{33}$ (wherein Hal and R$^{33}$ are as defined above) (for example, isopropyl chlorocarbonate), together with an alkali metal carbonate such as sodium carbonate or potassium carbonate, and an alkali metal iodide such as sodium iodide or potassium iodide, at 25 to 60° C., post-treating the product, and crystallizing the treated product. Solvents used for the crystallization include lower alcohols, such as methanol, ethanol, and isopropyl alcohol. These solvents may be used together with water.

All the compounds represented by formula (IIa') synthesized by this process are obtained as triazoles substituted at the 2-position. The above process is advantageous in that 1,1'-carbonyldiimidazole, which is expensive and unstable, is not used as the reactant, any by-product derived from 1,1'-carbonyldiimidazole is not produced, and the compounds represented by formula (IIa') wherein Q represents the group (i) are obtained in high purity at high yield.

<Process D>

The compound represented by formula (IIa'), wherein Q represents group (i), may also be prepared by directly reacting the compound represented by formula (V) with the compound represented by formula (IV) (for example, 1-chloro-2-methylpropyl-isopropyl carbonate).

More specifically, the compound represented by formula (V) may be reacted with the compound represented by formula (IV) in an organic solvent such as acetone, acetonitrile, ethyl acetate, or N,N-dimethylformamide, together with an inorganic base such as sodium carbonate, potassium carbonate, cesium carbonate, or sodium hydroxide, and an alkali metal iodide such as sodium iodide or potassium iodide, at 25 to 60° C. for 1 to 70 hr.

The compound represented by formula (IIa') may be purified by conventional purification methods, for example, a solvent extraction, crystallization, or column chromatography on silica gel.

All the compounds represented by formula (IIa') synthesized by the above process can be advantageously obtained as triazoles substituted at the 2-position. This seems to be due to the addition of the alkali metal iodide to the reaction system. The process is further advantageous in that the compounds represented by formula (IIa') can be simply produced from the compound represented by formula (V) in a single step. An additional advantage of the process is that the formation of by-products derived from impurities contained in a ketone or an aldehyde (for example, isobutyric acid in isobutylaldehyde) represented by R$^{31}$R$^{32}$C=O which is reacted with the compound represented by formula (V) in the process B and C can be avoided and high-purity compounds represented by formula (IIa') can be obtained.

Synthesis (2) of compound of formula (IIa)

The compound represented by formula (IIa) may be produced by nitration of the compound represented by formula (VI). The nitration may be carried out in the presence of a nitrating agent such as (concentrated) nitric acid or fuming nitric acid without a solvent or in a solvent which is not involved in the reaction (for example, acetic anhydride, concentrated sulfuric acid, methylene chloride, or chloroform) at −10 to 50° C. for 10 min to 24 hr.

The compound represented by formula (VI) may be prepared by introducing —CQR$^{31}$R$^{32}$ into the triazole group of the compound represented by formula (VII). The substituent —CQR$^{31}$R$^{32}$ may be introduced according to the process A, B. C, or D.

The compound represented by formula (VII) may be prepared by deprotecting the compound represented by formula (VIII).

The deprotection may be carried out according to a method described in D. R. Buckle and C. J. M. Rockell, J. Chem. Soc., Perkin Trans. I, 627 (1982), F. E. Nielsen, E. B. Pedersen, J. Heterocycl. Chem., 22, 1693 (1985). Specifically, when R$^{61}$ represents a benzyl, diphenylmethyl, triphenylmethyl, 4-methoxybenzyl, 3,4,5-trimethoxybenzyl, benzyloxymethyl, or trimethylsilyl, the deprotection may be carried out by reacting the compound represented by formula (VIII) with a mineral acid such as dilute hydrochloric acid or dilute sulfuric acid, or an organic acid such as trifluoroacetic acid either as such or after dilution with a solvent which is not involved in the reaction (for example, methylene chloride or toluene) at 15 to 80° C. for 1 to 24 hr.

The compound represented by formula (VII) may also be prepared by reacting the compound represented by formula (XII) with the compound represented by formula (XIII') in a solvent which is not involved in the reaction (for example, tetrahydrofuran, diethyl ether, diisopropyl ether, tert-butyl methyl ether, or toluene) at −78 to 100° C. for 15 min to 24 hr. The compound represented by formula (XIII') may be easily produced by reacting metal azide compounds such as sodium azide represented by formula (x'), various alkylsilyl azides, and various alkyltin azides, with an acetylenedicarboxylic diester.

The compound represented by formula (VII) may also be prepared by reacting the compound represented by formula (IX) with the metal azide compound represented by formula (X') in a solvent which is not involved in the reaction (for example, water, ethanol, isopropyl alcohol, tetrahydrofuran, diisopropyl ether, methylene chloride, acetone, toluene, ethyl acetate, N,N-dimethylformamide, or dimethylsulfoxide) at 0 to 120° C. for 1 to 24 hr.

Synthesis of compound represented by formula (VIII)

The compound represented by formula (VIII) may be prepared by reacting the compound represented by formula (IX) with the azide organic compound represented by formula (X) such as p-methoxybenzyl azide. The reaction may be carried out by a reaction of the compound represented by formula (IX) with the compound represented by formula (X').

The compound represented by formula (IX) may be prepared by reacting the compound represented by formula (XI) with chlorine, bromine, or iodine in a solvent which is not involved in the reaction (for example, water, ethanol, isopropyl alcohol, tetrahydrofuran, diisopropyl ether, methylene chloride, acetic acid, N,N-dimethylformamide, or dimethylsulfoxide) at −10 to 30° C. for 10 min to 24 hr and then reacting the resultant halide with an organic base such as triethylamine, diisopropylethylamine, triisopropylamine, pyridine, picoline, lutidine, collidine, or quinoline, or an inorganic base such as potassium carbonate sodium carbonate, cesium carbonate, potassium hydrogencarbonate, or sodium hydrogencarbonate in the absence of a solvent or in a solvent which is not involved in the reaction (for example, water, ethanol, isopropyl alcohol, tetrahydrofuran, diisopropyl ether, methylene chloride, acetone, toluene, N,N-dimethylformamide, or dimethylsulfoxide) at 0 to 50° C. for 1 to 24 hr.

The compound represented by formula (XI) may be prepared by a method described, for example, in Eur. J. Med. Chem., 23, 45 (1988) or U.S. Pat. No. 4,562,068.

The compound represented by formula (VIII) may also be prepared by converting a halo represented by formula (XIV) to an organometal compound represented by formula (XII) (for example, M represents lithium, magnesium chloride, magnesium bromide, magnesium iodide, zinc bromide, zinc iodide, cadmium bromide, cadmium iodide, copper or the like) and then reacting the compound represented by formula (XII) with the compound represented by formula (XIII) in a solvent which is not involved in the reaction (for example, tetrahydrofuran, diethyl ether, diisopropyl ether, tert-butyl methyl ether, or toluene) at −78 to 100° C. for 15 min to 24 hr. The compound represented by formula (XIII) may be easily prepared by reacting an azide compound (X) synthesized, for example, by a method described in J. Heterocyclic Chem., 21, 1669 (1984) with an acetylenedicarboxylic diester.

Synthesis of compound of formula (V)

The compound represented by formula (V) may be prepared by deprotecting the compound represented by formula (XV). The deprotection may be carried out by the method described in connection with the deprotection of the compound represented by formula (VIII) to produce the compound represented by formula (VII).

The compound represented by formula (V) may also be produced by reacting the compound represented by formula (XVI) with the compound represented by formula (X'). The reaction may be carried out by the method described above in connection with the reaction of the compound represented by formula (IX) with the compound represented by formula (X').

The compound represented by formula (V) may also be produced by nitrating the compound represented by formula (VII). The nitration may be carried out by the method described above in connection with the nitration of the compound represented by formula (VI) to produce the compound represented by formula (IIa).

The compound represented by formula (XV) may be produced by reacting the compound represented by formula (XVI) with the compound represented by formula (X). The reaction may be carried out by the method described above in connection with the reaction of the compound represented by formula (IX) with the compound represented by formula (X).

The compound represented by formula (XVI) may be produced from the compound represented by formula (XVII) by the method described above in connection with the production of the compound represented by formula (IX). from the compound represented by formula (XI).

The compound represented by formula (XVII) may be produced by a method described, for example, in Eur. J. Med. Chem., 23, 45 (1988) or U.S. Pat. No. 4,562,068.

The compound represented by formula (XV) may also be produced by nitrating the compound represented by formula (VIII). The nitration may be carried out by the method described above in connection with the nitration of the compound represented by formula (VI) to produce the compound represented by formula (IIa).

Further, the compound represented by formula (XV) may also be produced, for example, by a method described in WO 95/18130.

Pharmaceutical Composition

Oral administration of the compound represented by formula (I) according to the present invention to experimental animals have shown that the compound represented by formula (III) is detected in a higher concentration in plasma compared with administration of the compound represented by formula (III) alone. WO 95/18130 and WO 97/00258 disclose use of the compound represented by formula (III) as a therapeutic agent for allergic diseases. The compound represented by formula (I), after it is passed through various mucous membranes including digestive tracts, is converted in vivo to the compound represented by formula (III) which develops antiallergic activity.

The compound according to the present invention can be used as therapeutic agents for allergic diseases, for example, bronchial asthma, aczema, hives, allergic gastroenteritis, allergic rhinitis, and allergic conjunctivitis. The term "therapy" or "treatment" include "prevention" or "prophylaxis."

When orally administered, the compound according to the present invention may be formulated using conventional pharmaceutically acceptable excipients (for example, lactose, crystalline cellulose, starch, and calcium phosphate), binders (for example, starch, sodium carmellose, and hydroxypropylcellulose), disintegrators (calcium carmellose, calcium carbonate and the like), and lubricants (magnesium stearate, talc and the like) into tablets, capsules, granules, dry syrups, and various liquid preparations commonly used in medical treatment by conventional methods. Further, these various preparations may also be sustained—release preparations which release the ingredient for a long period of time.

According to pharmacological activities including antiallergic action of the compound represented by formula (III), the compound according to the present invention may be applied to various treatments through administration routes other than oral administration. Dosage forms for this purpose include, but are not limited to, sublingual tablets, suppositories, inhalants, nasal drops, eye drops, and percutaneous absorption preparations, for example, patches or ointments/creams.

Although the content of the compound according to the present invention in the pharmaceutical composition depends on the preparations, it is generally in the range of from 1 to 70% by weight, preferably from about 5 to 50% by weight, based on the whole composition.

The dose for the treatment of allergic diseases may be appropriately determined individually in view of the direction for use, the age and sex of patients, the severity of symptoms and the like. In the case of oral preparations, sublingual tablets, or suppositories, however, the compound according to the present invention, or the salt or solvate thereof may be administered at a dose in the range of from 0.05 to 5 g/day, preferably 0.1 to 1.0 g/day, at one time or dividedly several times. Regarding other dosage forms, the dose may be properly increased or decreased depending on the intended use.

EXAMPLES

The present invention is further illustrated by the following Examples that are not intended as a limitation of the invention.

Synthesis Example 1

7,8-Dimethoxy-4 (5H),10-dioxo-1H-1,2,3-triazolo [4,5-c][1]benzazepine (a) 1.5 N butyl lithium (26.8 ml, 40.2 mmol) was added to a solution of diisopropylamine (6.0 ml, 42.8 mmol) in tetrahydrofuran (75 ml) under an argon atmosphere at −78° C. The mixture was stirred for one hr. Ethyl propiolate (3.4 ml, 33.5 mmol) and a solution of 4,5-dimethoxy-2-nitrobenzaldehyde (5.0 g, 23.7 mmol) in tetrahydrofuran (50 ml) were added thereto in that order, and the mixture was stirred at −78° C. for additional 1.5 hr. A solution of acetic acid (7.0 ml, 122 mmol) in tetrahydrofuran (20 ml) was added thereto, followed by addition of water. The mixture was extracted with ethyl acetate. The organic layer was washed with dilute hydrochloric acid, water, a saturated aqueous sodium hydrogencarbonate solution, and saturated brine solution in that order. The organic layer was then dried over anhydrous magnesium sulfate. The solvent was evaporated under reduced pressure to give ethyl 4-hydroxy-4-(4,5-dimethoxy-2-nitrophenyl)-2-butynoate as an oil (8.59 g). The resultant ethyl 4-hydroxy-4-(4,5-dimethoxy-2-nitrophenyl)-2-butynoate was dissolved in toluene (80 ml).

4-Methoxybenzyl azide (11.6 g, 71.1 mmol) was added to the solution. The mixture was heated at 100° C. with stirring overnight. The reaction solution was cooled to room temperature and then purified by column chromatography on silica gel (hexane : ethyl acetate=2:1).

The precipitate created in the eluate was collected by filtration to give a 1:5 mixture (2.60 g, 23%) of ethyl 4-(hydroxy-(4,5-dimethoxy-2-nitrophenyl)methyl)-1-(4-methoxybenzyl)-1H-1,2,3-triazole-5-carboxylate (a-1: low polar product (LP)) and ethyl 5-(hydroxy-(4,5-dimethoxy-2-nitrophenyl)methyl)-1-(4-methoxybenzyl)-1H-1,2,3-triazole-4-carboxylate (a-2: high polar product (MP)). On the other hand, the filtrate was concentrated under reduced pressure to give a 2.5:1 mixture (4.68 g, 42%) of the compound (a-1: (LP)) and the compound (a-2: (MP)).

2.5:1 Mixture of a-1 (LP) and a-2 (MP):

$^1$H-NMR (CDCl$_3$): δ 1.38 (15/7H, t), 1.39 (6/7H, t), 3.56 (6/7H, s), 3.72 (6/7H, s), 3.78 (15/7H, s), 3.91 (6/7H, s), 3.97 (15/7H, s), 3.99 (15/7H, s), 4.41 (4/7H, q), 4.44 (10/7H, q), 4.97 (5/7H, d), 5.07 (2/7H, d), 5.48 (2/7H, d), 5.78 (5/7H, d), 5.71 (2/7H, d), 5.84 (5/7H, d), 6.32 (2/7H, s), 6.83 (10/7H, d), 6.67 (4/7H, d), 6.99 (4/7H, d), 7.07 (2/7H, d), 7.21 (10/7H, d), 7.48 (2/7H, s), 7.51 (5/7H, s), 7.71 (5/7H, s). EIMS: m/z 472 (M$^+$).

(b) Manganese dioxide (14 g) was added to a solution of the 2.5:1 mixture (4.63 g, 9.80 mmol) of the compound a-1 and the compound a-2 prepared in step (a) in methylene chloride (100 ml). The mixture was stirred at room temperature overnight. Manganese dioxide (4.6 g) was added thereto, and the mixture was stirred at room temperature for 8 hr. The reaction solution was filtered through Celite, followed by washing with ethyl acetate. The solvent was evaporated under reduced pressure. The residue was purified by column chromatography on silica gel (hexane:ethyl acetate=2:1) to give ethyl 1-(4-methoxybenzyl)-4-(4,5-dimethoxy-2-nitrobenzoyl)-1H-1,2,3-triazole-5-carboxylate as a brown crystal powder (b-1: LP) (2.75 g, 60%) and ethyl 1-(4-methoxybenzyl)-5-(4,5-dimethoxy-2-nitrobenzoyl)-1H-1,2,3-triazole-4-carboxylate as a brown crystal powder (b-2: MP) (1.12 g, 24%).

b-1 (LP):

$^1$H-NMR (CDCl$_3$): δ 1.38 (3H,t), 3.78 (3H,s), 3.98 (3H,s), 4.02 (3H,s), 4.43 (2H,q), 5.72 (2H,s), 6.85 (2H,d), 6.99 (1H,s), 7.24 (2H,d), 7.69 (1H,s). SIMS: m/z 471 (M$^+$+1).

b-2 (MP):

$^1$H-NMR (CDCl$_3$): δ 1.19 (3H, t), 3.79 (3H, s), 3.91 (3H, s), 4.00 (3H, s), 4.10 (2H, q), 5.79 (2H, s), 6.80 (1H, s), 6.88 (2H, d), 7.42 (2H, d), 7.52 (1H, s). EIMS: m/z 470 (M$^+$).

(c) A 1 N aqueous sodium hydroxide solution (13 ml) was added to a solution of ethyl 1-(4-methoxybenzyl)-4-(4,5-dimethoxy-2-nitrobenzoyl)-1H-1,2,3-triazole-5-carboxylate (b-1) (3.04 g, 6.46 mmol), prepared in step (b), in tetrahydrofuran (40 ml). The mixture was stirred at room temperature for 3.5 hr. The reaction solution was diluted with ether, and water was added thereto. The aqueous layer was acidified with hydrochloric acid and extracted with ethyl acetate, followed by washing with water and saturated brine solution. The organic layer was dried over anhydrous magnesium sulfate. The solvent was evaporated under reduced pressure to give 1-(4-methoxybenzyl)-4-(4,5-dimethoxy-2-nitrobenzoyl)-1H-1,2,3-triazole-5-carboxyic acid as light yellow oil (c-1':LP) (2.55 g, 89%). The resultant 1-(4-methoxybenzyl)-4-(4,5-dimethoxy-2-nitrobenzoyl)-1H-1,2,3-triazole-5-carboxylic acid (c-1':LP) (1.07 g, 2.42 mmol) was dissolved in a mixed solvent composed of ethanol (50 ml) and ethyl acetate (50 ml). 10% palladium-carbon (129 mg) was added thereto. The mixture was stirred in a hydrogen atmosphere at room temperature for 4 hr. Methylene chloride was added to the reaction solution to dissolve the precipitated crystal, followed by filtration through Celite. The filtrate was concentrated under reduced pressure to give 4-(2-amino-4,5-dimethoxybenzoyl)-1-(4-methoxybenzyl)-1H-1,2,3-triazole-5-carboxylic acid (c-1: LP) (1.06 g, 100%).

c-1' (LP);

$^1$H-NMR (CDCl$_3$): δ 3.78 (3H, s), 3.99 (3H, s), 4.06 (3H, s), 6.02 (2H, s), 6.84 (2H, d), 6.94 (1H, s), 7.40 (2H, d), 7.76 (1H, s), 13.80 (1H, brs). SIMS: m/z 443 (M+1).

c-1 (LP);

$^1$H-NMR (CDCl$_3$): δ 3.78 (3H, s), 3.88 (3H, s), 3.94 (3H, s), 6.06 (2H, s), 6.11 (1H, s), 6.86 (2H, d), 7.45 (2H, d), 8.58 (1H, s). SIMS: m/z 413 (M$^+$+1).

Likewise, ethyl 1-(4-methoxybenzyl)-5-(4,5-dimethoxy-2-nitrobenzoyl)-1H-1,2,3-triazole-4-carboxylate (b-2) (3.12 g, 6.63 mmol) prepared in step (b) was hydrolyzed in a tetrahydrofuran (100 ml) solution with a 1 N aqueous sodium hydroxide solution (13 ml) at room temperature for 3.5 hr. Thus, 1-(4-methoxybenzyl)-5-(4,5-dimethoxy-2-nitrobenzoyl)-1H-1,2,3-triazole-4-carboxylic acid (c-2': MP) (2.32 g, 79%) was obtained as a yellow crystal powder.

c-2' (MP);

$^1$H-NMR (CDCl$_3$): δ 3.80 (3H, s), 3.94 (3H, s), 4.00 (3H, s), 5.79 (2H, s), 6.89 (1H, s), 6.91 (2H, d), 7.47 (2H, d), 7.54 (1H, s). SIMS: m/z 443 (M$^+$+1).

(d) Tributylamine (0.64 ml, 2.69 mmol), 2-fluoro-1-methylpyridinium p-toluenesulfonate (793 mg, 2.80 mmol), and 3,4-dihydro-2H-pyrido[1,2-a]pyrimidin-2-one (453 mg, 3.06 mmol) were added in that order to a solution of 4-(2-amino-4,5-dimethoxybenzoyl)-1-(4-methoxybenzyl)-1H-1,2,3-triazole-5-carboxylic acid (c-1) (1.05 g, 2.55 mmol) in methylene chloride (30 ml) in an argon atmosphere under ice cooling. The mixture was stirred under ice cooling for one hr and then stirred at room temperature for 2 hr.

Water was added to the reaction mixture, and the mixture was extracted with chloroform. The organic layer was washed with dilute hydrochloric acid, water, saturated aqueous sodium hydrogencarbonate solution, and saturated brine solution. The organic layer was dried over anhydrous magnesium sulfate. The solvent was evaporated under reduced pressure. The resultant precipitate was collected by filtration, washed with diethyl ether and water, and dried to give 7,8-dimethoxy-3-(4-methoxybenzyl)-4 (5H),10-dioxo-3H-1,2,3-triazolo[4,5-c][1]benzazepine as light yellow crystal powder (d-1:LP) (477 mg, 48%).

d-1 (LP):

$^1$H-NMR (DMSO-d$_6$): δ 3.72 (3H, s), 3.84 (6H, s), 6.09 (2H, s), 6.90 (2H, d), 7.16 (1H, s), 7.30 (2H, d), 7.67 (1H, s), 11.33 (1H, s). EIMS: m/z 394 (M$^+$).

(e) Anisole (0.5 ml) and trifluoroacetic acid (5.0 ml) were added to 7,8-dimethoxy-3-(4-methoxybenzyl)-4(5H),10-dioxo-3H-1,2,3-triazolo[4,5-c][1]benzazepine (d-1) (471 mg, 1.19 mmol). The mixture was stirred at 60° C. for 3 hr. Thereafter, the solvent was evaporated under reduced pressure. The resultant precipitate was collected by filtration, washed with diethyl ether and water, and then dried to give the title compound 7,8-dimethoxy-4 (5H), 10-dioxo-1H-1,2,3-triazolo[4,5-c][1]benzazepine (e) as yellow powder (319 mg, 98%). The 7,8-dimethoxy-4(5H), 10-dioxo-1H-1,2,3-triazolo[4,5-c][1]benzazepine (e) (238 mg, 0.867 mmol) was dissolved in a 1 N aqueous sodium hydroxide solution. The solution was purified on Diaion HP-20 (water:acetone=9:1) to give the title compound: a sodium salt of 7,8-dimethoxy-4(5H), 10-dioxo- 1H-1,2,3-triazolo[4,5-c][1]benzazepine (e') as light yellow powder (231 mg, 90%:).

e:
$^1$H-NMR (DMSO-d$_6$): δ 3.85 (3H, s), 3.86 (3H, s), 7.22 (1H, s), 7.70 (1H, s), 11.23 (1H, s). SIMS: m/z 275 (M$^+$+1).
e':
FDMS: m/z 274 (M$^+$–Na+1).

Synthesis Example 2

Ethyl 5-(4,5-dimethoxy-2-nitrobenzoyl)-1H-1,2,3-triazole-4- carboxylate

Anisole (1 ml) was added to a solution of an about 1:1 mixture (4.4 g) of ethyl 1-(4-methoxybenzyl)-4-(4,5-dimethoxy-2-nitrobenzoyl)-1H-1,2,3-triazole-5-carboxylate (Synthesis Example 1, b-1) and ethyl 1-(4-methoxybenzyl)-5-(4,5-dimethoxy-2-nitrobenzoyl)-1H-1,2,3-triazole-4-carboxylate(Synthesis Example 1, b-2) in trifluoroacetic acid (10 ml), and the mixture was stirred at 60° C. for 10 hr. After the mixture was allowed to stand for cooling, the solvent was evaporated under reduced pressure, followed by azeotropic evaporation using toluene. The resultant crystal was collected by filtration, washed with diethyl ether, and then dried to give ethyl 5-(4,5-dimethoxy-2-nitrobenzoyl)-1H-1,2,3-triazole-4-carboxylate (3.12 g, 95%).

$^1$H-NMR (CDCl$_3$): δ 1.42 (3H, t), 4.00 (3H, s), 4.03 (3H, s), 4.47 (2H, q), 7.02 (1H, s), 7.67 (1H, s).

Synthesis Example 3

Ethyl 4-(5-isopropoxy-4-methoxy-2-nitrobenzoyl)-1-(4-methoxybenzyl)-1H-1,2,3-triazole-5-carboxylate and ethyl 5-(5-isopropoxy-4-methoxy-2-nitrobenzoyl)-1-(4-methoxybenzyl)-1H-1,2,3-triazole-4-carboxylate (a) 1.5 N butyl lithium (22.6 ml, 33.8 mmol) was added to a solution of diisopropylamine (5.0 ml, 36.0 mmol) in tetrahydrofuran (75 ml) under an argon atmosphere at –78° C., and the mixture was stirred for one hr. Ethyl propiolate (2.9 ml, 28.2. mmol) and a solution of 5-isopropoxy-4-methoxy-2-nitrobenzaldehyde (4.5 g, 18.8 mmol) in tetrahydrofuran (50 ml) were then added thereto in that order, and the mixture was stirred at –78° C. for additional 1.5 hr. A solution of acetic acid (5.9 ml, 102 mmol) in tetrahydrofuran (20 ml) was added to the reaction solution. Water was then added thereto, followed by extraction with ethyl acetate. The organic layer was washed with dilute hydrochloric acid, water, a saturated aqueous sodium hydrogencarbonate solution, and saturated brine solution. The organic layer was dried over anhydrous magnesium sulfate. The solvent was evaporated under reduced pressure to give ethyl 4-(5-isopropoxy-4-methoxy-2-nitrophenyl)-4-hydroxy-2-butynoate (7.27 g). The resultant ethyl 4-(5-isopropoxy-4-methoxy-2-nitrophenyl)-4-hydroxy-2-butynoate was dissolved in toluene (60 ml). 4-Methoxybenzyl azide (9.2 g, 56.4 mmol) was added to the solution. The mixture was heated at 100° C. with stirring overnight. The reaction solution was cooled to room temperature. The solvent was evaporated under reduced pressure. The residue was purified by column chromatography on silica gel (hexane:ethyl acetate=1:2) to give a 1:1 mixture (7.01 g, 75%) of ethyl 4-(1-hydroxy-(5-isopropoxy-4-methoxy-2-nitrophenyl)methyl)-1-(4-methoxybenzyl)-1H-1,2,3-triazole-5-carboxylate (a-1: low polar product (LP)) and ethyl 5-(1-hydroxy-(5-isopropoxy-4-methoxy-2-nitrophenyl)methyl)-1-(4-methoxybenzyl)-1H-1,2,3-triazole-4-carboxylate (a-2: high polar product (MP)).

1:1 mixture of a-1 (LP), a-2 (MP):
$^1$H-NMR (CDCl$_3$): δ 1.34–1.55 (9H, m), 3.59 (1H, d), 3.77 (3H, s), 3.92 (3H, s), 4.41 (2H, q), 4.69–4.76 (1H, m), 5.81 (1H, s), 5.83 (1H, s), 6.82 (2H, d), 6.93 (1H, d), 7.20 (2H, d), 7.43 (1H, s), 7.67 (1H, s). SIMS: m/z 501 (M$^+$+1).

(b) Active manganese dioxide (24 g) was added to a solution of the 1:1 mixture (7.01 g, 14.02 mmol) of the compound (a-1) and the compound (a-2), prepared in the above step (a), in methylene chloride (160 ml), and the mixture was stirred at room temperature overnight. The reaction solution was filtered through Celite and washed with methylene chloride. The solvent was then evaporated under reduced pressure to give a 1:1 mixture (6.98 g, 100%) of ethyl 4-(5-isopropoxy-4-methoxy-2-nitrobenzoyl)-1-(4-methoxybenzyl)-1H-1,2,3-triazole-5-carboxylate (b-1:LP) and ethyl 5-(5-isopropoxy-4-methoxy-2-nitrobenzoyl)-1-(4-methoxybenzyl)-1H-1,2,3-triazole-4-carboxylate (b-2 :MP) as a foam.

1:1 mixture of b-1 (LP), b-2 (MP):
$^1$H-NMR (CDCl$_3$ ): δ 1.17 (3/2H, t), 1.37–1.43 (9/2H, m), 3.78 (3H, s), 3.97 (3/2H, s), 3.99 (3/2H, s), 4.08 (1H, q), 4.42 (1H, q), 4.55–4.60 (1/2H, m), 4.67–4.72 (1/2H, m), 5.70 (1H, s), 5.78 (1H, s), 6.79 (1/2H, s), 6.84–6.88 (2H, m), 6.97 (1/2H, s), 7.24 (1H, d) 7.42 (1H, d), 7.52 (1/2H, s), 7.67 (1/2H, s). EIMS: m/z 498 (M$^+$).

Intermediate 1

Methyl 4-(3,4-dimethoxyphenyl)-4-oxo-2-butynoate

A solution of bromine (0.05 ml) in methylene chloride (5 ml) was added dropwise to a solution of methyl 4-(3,4-dimethoxyphenyl)-4-oxo-2-butenoate (201 mg, 0.8 mmol) in methylene chloride (5 ml) under ice cooling over a period of 20 min. The mixture was stirred under ice cooling for 1 hr. The reaction temperature was then raised to room temperature. The reaction solution was treated by a conventional method to give methyl 2,3-dibromo-4-(3,4-dimethoxyphenyl)-4-oxobutanoate (332 mg, 100%) in the form of a diastereo mixture (mixing ratio=61:39) as a colorless foam. The diastereo mixture was used in the next reaction without separation.

Major component:
$^1$H-NMR (CDCl$_3$): δ 3.74 (3H, s), 3.92 (3H, s), 3.95 (3H, s), 4.83 (1H, d)/ 5.44 (1H, d), 6.91 (1H, d), 7.49 (1H, d), 7.64 (1H, dd). EIMS: m/z 411 (M$^+$+1).

Minor component:
$^1$H-NMR (CDCl$_3$): δ 3.88 (3H, s), 3.94 (3H, s), 3.96 (3H, s), 4.96 (1H, d), 5.62 (1H, d), 6.92 (1H, d), 7.57 (1H, d), 7.64 (1H, dd). EIMS: m/z 411 (M$^+$+1).

A solution of triethylamine (27 mg) in methylene chloride (0.5 ml) was added to a solution of methyl 2,3-dibromo-4-(3,4-dimethoxyphenyl)-4-oxobutanoate (49 mg, 0.1 mmol), prepared above, in methylene chloride (0.5 ml). The mixture was stirred at room temperature for 15 min and then heated under reflux with stirring for 2 hr. The mixture was then treated by a conventional method, and the crude product was purified by column chromatography on silica gel (hexane/ ethyl acetate) to give the title compound as a yellow crystal (21 mg, 71%).

$^1$H-NMR (CDCl$_3$): δ 3.89 (3H, s), 3.95 (3H, s), 3.99 (3H, s), 6.94 (1H, d), 7.56 (1H, d), 7.82 (1H, dd). EIMS: m/z 248 (M$^+$).

Intermediate 2

Ethyl 4-(3,4-Dimethoxyphenyl)-4-oxo-2-butynoate

The procedure as described above in connection with Intermediate 1 was repeated to prepare ethyl 2,3-dibromo-4-(3,4-dimethoxyphenyl)-4-oxobutanoate (7.3 g, 95%) in the form of a diastereo mixture as a colorless foam (mixing ratio=63:37) from, a solution of ethyl 4-(3,4-dimethoxyphenyl)-4-oxo-2-butenoate (4.8 g, 18 mmol) in methylene chloride (500 ml) and a solution of bromine (1.1 ml) in methylene chloride (100 ml). The diastereo mixture was used in the next reaction without separation.

Major component:
$^1$H-NMR (CDCl$_3$): δ 1.24 (3H, t), 3.94 (3H, s), 3.97 (3H, s), 4.20 (2H, q), 4.84 (1H, d), 5.46 (1H, d), 6.93 (1H, d), 7.51 (1H, d), 7.66 (1H, dd). EIMS: m/z 424 (M$^+$).

Minor component:
$^1$H-NMR (CDCl$_3$): δ 1.38 (3H, t), 3.96 (3H, s), 3.98 (3H, s), 4.36 (1H, q), 4.97 (1H, d), 5.65 (1H, d), 6.94 (1H, d), 7.59 (1H, d), 7.67 (1H, dd). EIMS: m/z 424 (M$^+$+1).

A solution of ethyl 2,3-dibromo-4-(3,4-dimethoxyphenyl)-4-oxobutanoate (4.76 g, 11.2 mmol), prepared above, in methylene chloride (20 ml) and a solution of triethylamine (4 g) in methylene chloride (5 ml) were subjected to reaction and treatment in the same manner as described above in connection with Intermediate 1. The crude product was purified by column chromatography on silica gel (hexane/ethyl acetate) to give the title compound (2.4 g, 82%) as a yellow crystal.

$^1$H-NMR (CDCl$_3$): δ 1.37 (3H, t), 3.94 (3H, s), 3.98 (3H, s), 4.35 (2H, q), 6.95 (1H, d), 7.57 (1H, d), 7.83 (1H, dd). EIMS: m/z 262 (M$^+$).

Intermediate 3

Ethyl 4-(4 5-dimethoxy-2-nitrophenyl)-4-oxo-2-butynoate

The procedure as described above in connection with Intermediate 1 was repeated to prepare ethyl 2,3-dibromo-4-(4,5-dimethoxy-2-nitrophenyl)-4-oxobutanoate (337 mg, 100%) in the form of a diastereo mixture as light brown oil (mixing ratio=2:1) from a solution of ethyl 4-(4,5-dimethoxy-2-nitrophenyl)-4-oxo-2-butenoate (199 mg, 0.6 mmol) in methylene chloride (10 ml) and a solution of bromine (0.04 ml) in methylene chloride (5 ml). The diastereo mixture was used in the next reaction without separation.

Major component:
$^1$H-NMR (CDCl$_3$): δ 1.32 (3H, t), 4.01 (6H, s), 4.31 (2H, q), 5.03 (1H, d), 5.52 (1H, d), 6.99 (1H, s), 7.63 (1H, s).

Minor component:
$^1$H-NMR (CDCl$_3$): δ 1.34 (3H, t), 4.01 (6H, s), 4.31 (2H, q), 4.91 (1H, d), 5.25 (1H, d), 7.02 (1H, s), 7.65 (1H, s).

Diisopropylethylamine (74 μl) was allowed to act on the product (90 mg, 0.2 mmol), prepared above, in methylene chloride (1 ml). The crude product was purified by column chromatography on silica gel (hexane/ethyl acetate) to give the title compound (17 mg, 29%) as a yellow crystal powder.

This compound may also be produced by oxidizing ethyl 4-hydroxy-4-(4,5-dimethoxy-2-nitrophenyl)-2-butynoate described in Synthesis Example 1 in methylene chloride with active manganese dioxide under conventional reaction conditions (for example, at room temperature for 10 hr).

$^1$H-NMR (CDCl$_3$) : δ 1.36 (3H, t), 4.01 (3H, s), 4.02 (3H, s), 4.27 (2H, q), 7.06 (1H, s), 7.55 (1H, s).

Intermediate 4

Methyl 5-(3,4-dimethoxybenzoyl)-1-(4-methoxybenzyl)-1H-1,2,3-triazole-4-carboxylate and methyl 4-(3,4-dimethoxybenzoyl)-3-(4-methoxybenzyl)-1H-1,2,3-triazole-5-carboxylate A solution of 4-methoxybenzyl azide (37 mg, 0.2 mmol) in toluene (1 ml) was added to a solution of methyl 4-(3,4-dimethoxyphenyl)-4-oxo-2-butynoate (47 mg, 0.2 mmol) (Intermediate 1) in toluene (1 ml). The mixture was stirred at 100° C. for 18 hr. The reaction solution was concentrated under reduced pressure. The residue was purified by column chromatography on silica gel (hexane/ethyl acetate) to give the title compound (low polar colorless oil (30 mg, 39%) and high polar compound as a light yellow foam (40 mg, 51%)).

Low polar compound:
$^1$H-NMR (CDCl$_3$): δ 3.71 (3H, s), 3.72 (3H, s), 3.87 (3H, s), 3.88 (3H, s), 5.75 (2H, s), 6.80 (2H, d), 6.82 (1H, d), 7.26 (2H, d), 7.58 (1H, dd), 7.62 (1H, d). EIMS: m/z 411 (M$^+$).

High polar compound:
$^1$H-NMR (CDCl$_3$): δ 3.60 (3H, s), 3.64 (3H, s), 3.81 (3H, s), 3.85 (3H, s), 5.43 (2H, s), 6.57 (2H, d), 6.60 (1H, d), 6.77 (1H, d), 6.99 (2H, d), 7.25 (1H, d). EIMS: m/z 412 (M$^+$+1).

Intermediate 5

Ethyl 5-(3,4-dimethoxybenzoyl)-1H-1,2,3-triazole-4-carboxylate

In the same manner as in Intermediate 4, a solution of 4-methoxybenzyl azide (1.8 g) in toluene (10 ml) was added to a solution of ethyl 4-(3,4-dimethoxyphenyl)-4-oxo-2-butynoate (intermediate 2) (2.4 g, 9.2 mmol) in toluene (80 ml). The mixture was stirred at 100° C. for 18 hr. The reaction solution was concentrated under reduced pressure to give a mixture of ethyl 5-(3,4-dimethoxybenzoyl)-1-(4-methoxybenzyl)-1H-1,2,3-triazole-4-carboxylate and ethyl 4-(3,4-dimethoxybenzoyl)-3-(4-methoxybenzyl)-1H-1,2,3-triazole-5-carboxylate as an oil. The oil was used in the next reaction without purification.

Major component:
$^1$H-NMR (CDCl$_3$): δ 1.08 (3H, t), 3.68 (3H, s), 3.88 (3H, s), 3.92 (3H, s), 4.18 (2H, q), 5.51 (2H, s), 6.64 (2H, d), 6.67 (1H, d), 6.86 (2H, d), 7.07 (1H, dd), 7.31 (1H, d).

Minor component:
$^1$H-NMR (CDCl$_3$): δ 1.14 (3H, t), 3.80 (3H, s), 3.94 (3H, s), 3.95 (3H, s), 4.24 (2H, q), 5.82 (2H, s), 6.85–6.90 (3H, m), 7.33 (2H, d), 7.63 (1H, dd), 7.68 (1H, d).

A mixture of the above crude product, trifluoroacetic acid (7.9 ml), and anisole (1.2 g) was heated with stirring at 90° C. for 2 hr. The reaction mixture was concentrated under reduced pressure. Ethyl acetate was added to the residue. The mixture was extracted with a saturated aqueous sodium hydrogencarbonate solution. The aqueous layer was neutralized with hydrochloric acid and again extracted with ethyl acetate. The organic layer was washed with brine solution and dried over anhydrous magnesium sulfate. The solvent was evaporated to give the title compound as a light yellow solid (2.9 g, 91% in two steps).

¹H-NMR (CDCl₃): δ 1.23 (3H, s), 3.95 (3H, s), 3.96 (3H, s), 4.31 (2H, q), 5.59 (2H, s), 6.87 (1H, d), 7.41 (1H, dd), 7.62 (1H, d).

Intermediate 6

Ethyl 5(or 4)-(3,4-dimethoxybenzoyl)-1-(4-methoxybenzyl)-1H-1,2,3-triazole-4 (or 5)-carboxylate (a) A solution of butyl lithium in hexane (1.58 M, 0.24 ml, 0.39 mmol) was added at −78° C. to a solution of 4-bromoveratrol (50 μl, 0.35 mmol) in tetrahydrofuran (1.5 ml) under an argon atmosphere. After 15 min, this solution was added at −78° C. to a solution of diethyl 1-(4-methoxybenzyl)-1H-1,2,3-triazole-4,5-dicarboxylate (117 mg, 0.35 mmol) in tetrahydrofuran (1 ml). The mixture was stirred for 40 min. A saturated aqueous ammonium chloride solution was added to the reaction solution. The mixture was extracted with ethyl acetate. The organic layer was washed with saturated brine solution and dried. The solvent was evaporated. The residue was purified by column chromatography on silica gel (ethyl acetate/hexane) to give the title compound as a single compound (60 mg, 40%). The Rf value of silica gel thin-layer chromatography on silica gel and ¹H-NMR spectrum were the same as those for the major component of the mixture of two position isomers obtained by the conversion of Intermediate 5 to a triazole compound.

¹H-NMR (CDCl₃): δ 1.08 (3H, t), 3.68 (3H, s), 3.88 (3H, s), 3.92 (3H, s), 4.18 (2H, q), S.51 (2H, s), 6.64 (2H, d), 6.67 (1H, d), 6.86 (2H, d), 7.07 (1H, dd), 7.31 (1H, d). EIMS: m/z 425 (M⁺)

(b) A solution of 4-bromoveratrol (183 mg, 0.84 mmol) in tetrahydrofuran (1 ml) was added to a mixture of magnesium (33 mg, 1.36 mg atom) in tetrahydrofuran (1 ml) at room temperature under an argon atmosphere. After 20 min, the reaction solution was heated under reflux for 30 min. A minor amount of iodine was added thereto, followed by stirring for additional 20 min. The reaction solution was added to a solution of diethyl 1-(4-methoxybenzyl)-1H-1,2,3-triazole-4,5-dicarboxylate (218 mg, 0.84 mmol) in tetrahydrofuran (1 ml) under ice cooling. The temperature of the reaction solution was raised, and the reaction solution was then stirred at room temperature for 3 days. A saturated aqueous ammonium chloride solution was added to the reaction solution to stop the reaction The reaction mixture was treated in the same manner as in step (a) and purified by column chromatography on silica gel to give the title compound (68 mg, 19%).

Intermediate 7

Ethyl 5(4,5-dimethoxy-2-nitro benzoyl)-1-(4-methoxybenzyl)-1H-1,2,3-triazole-4-carboxylate and ethyl 4-(4,5-dimethoxy-2-nitrobenzoyl)-1-(4-methoxybenzyl)-1H-1,2,3-triazole-5-carboxylate In the same manner as in Intermediate 4,4-methoxybenzyl azide (19 mg) was added to a solution of ethyl 4-(4,5-dimethoxy-2-nitrophenyl)-4-oxo-2-butynoate (17 mg, 0.055 mmol), synthesized as described above in connection with Intermediate 3, in toluene (1 ml) The mixture was stirred at 60° C. for 20 hr. The reaction solution was concentrated. The residue was purified by column chromatography on silica gel (hexane/ethyl acetate) to give yellow crystal powder (low polar product:high polar product=2:3 mixture) (19 mg, 73%) The Rf value of thin-layer chromatography on silica gel and ¹H-NMR (CDCl₃) spectrum were the same as those for compounds b-1 (high polar product) and b-2 (low polar product) prepared in Synthesis Example 1.

Intermediate 8

Ethyl 5-(3,4-dimethoxybenzoyl)-2-(1-isopropoxycarbonyloxy-2-methylpropyl)-2H-1,2,3-triazole-4-carboxylate p-Toluenesulfonic acid monohydrate (482 mg, 2.5 mmol) and isobutylaldehyde (3.4 ml, 37 mmol) were added to a solution of ethyl 5-(3,4-dimethoxybenzoyl)-1H-1,2,3-triazole-4-carboxylate (7.7 g, 25 mmol), prepared in the same manner as described above in connection with Intermediate 5, in methylene chloride (115 ml) under an argon atmosphere at −20° C. The mixture was stirred at −20° C. for one hr. Carbonyldiimidazole (6.2 g, 38 mmol) was added thereto, followed by stirred at −20° C. for additional one hr. Isopropyl alcohol (20 ml) was added thereto. The mixture was cooled to −30° C. Trifluoroacetic acid (5.8 ml, 75 mmol) was added thereto. The mixture was stirred at room temperature for 18 hr. The reaction solution was treated by a conventional method and purified by column chromatography on silica gel (hexane/ethyl acetate) to give the title compound as a colorless liquid (10.9 g, 93.4%).

¹H-NMR (CDCl₃): δ 0.87 (3H, d), 1.15 (3H, d), 1.27 (3H, t), 1.28 (3H, d), 1.33 (3H, d), 2.76 (1H, m), 3.94 (3H, s), 3.96 (3H, s), 4.34 (2H, q), 4.90 (1H, sept), 6.54 (1H, d), 6.89 (1H, d), 7.47 (1H, d), 7.64 (1H, s). TSPMS: m/z 464 (M⁺+1).

Intermediate 9

Ethyl 5-(4,5-dimethoxy-2-nitrobenzoyl)-2-(1-isopropoxycarbonyloxy-2-methylpropyl)-2H-1,2,3-triazole-4-carboxylate 70% nitric acid (1 ml) was added to ethyl 5-(3,4-dimethoxybenzoyl)-2-(1-isopropoxycarbonyloxy-2-methylpropyl)-2H-1,2,3-triazole-4-carboxylate (86 mg, 0.19 mmol) as Intermediate 8 under ice cooling. The mixture was stirred at that temperature for 30 min. The reaction solution was poured into ice and then extracted with ethyl acetate. The organic layer was washed with a saturated aqueous sodium hydrogencarbonate solution and saturated brine solution in that order and dried over anhydrous magnesium sulfate. The solvent was evaporated to give the title compound as a single compound (49 mg, 52%). The Rf value of thin-layer chromatography on silica gel and ¹H-NMR spectrum were the same as those of the title compound of Example 20 (a).

¹H-NMR (CDCl₃): δ 0.72 (3H, d), 1.05 (3H, d), 1.25 (3H, d), 1.28 (3H, d), 1.44 (3H, t), 2.56 (1H, m), 4.00 (3H, s), 4.08 (3H, s), 4.49 (2H, q), 4.85 (1H, m), 6.35 (1H, d), 7.06 (1H, s), 7.62 (1H, s).

Example 1

1-(1-Isopropoxycarbonyloxyethyl)-7,8-dimethoxy-4 (5H), 10-dioxo-1H-1,2,3-triazolo[4,5-c][1] benzazepine (substituted at 1-position), 2-(1-isopropoxycarbonyloxyethyl)-7,8-dimethoxy-4(5H), 10-dioxo-2H-1,2,3-triazolo[4,5-c][1]benzazepine (substituted at 2-position), and 3-(1-isopropoxycarbonyloxyethyl)-7,8-dimethoxy-4 (5H), 10-dioxo-3H-1,2,3-triazolo[4,5-c][1]benzazeoine (substituted at 3-position)

1-Iodoethylisopropyl carbonate (2.82 g) and sodium hydrogencarbonate (919 mg) were added to a solution of 7,8-dimethoxy-4(5H), 10-dioxo-1H-1,2,3-triazolo[4,5-c][1] benzazepine (Synthesis Example 1) (1.00 g) in N,N-dimethylformamide (20 ml) under an argon atmosphere. The mixture was stirred at 60° C. for 18 hr. The solvent was evaporated under reduced pressure. Water and ethyl acetate were added thereto. The organic layer was separated. The organic layer was washed with water and saturated brine solution in that order and dried over anhydrous magnesium sulfate. The solvent was evaporated under reduced pressure. The resultant mixture was repeatedly purified by column chromatography on silica gel (hexane/ethyl acetate). As a result, the compound substituted at 3-position (275 mg), the compound substituted at 2-position (55 mg), and the compound substituted at 1-position (66 mg) were obtained each as yellow powder in the order of elution.

1-(1-Isopropoxycarbonyloxyethyl)-7,8-dimethoxy-4 (5H), 10-dioxo-1H-1,2,3-triazolo[4,5-c][1]benzazepine (substituted at 1-position).

$^1$H-NMR (CDCl$_3$): δ 1.24 (3H, d), 1.29 (3H, d), 2.14 (1H, d), 3.98 (3H, s), 4.08 (3H, s), 4.80–4.90 (2H, m), 7.10 (1H, s), 7.74 (1H, s), 7.80 (1H, q), 11.07 (1H, s).

2-1-Isopropoxycarbonyloxyethyl)-7,8-dimethoxy-4 (5H), 10-dioxo-2H-1,2,3-triazolo[4,5-c][1]benzazepine (substituted at 2-position).

$^1$H-NMR (CDCl$_3$): δ 1.27 (3H, d), 1.31 (3H, d), 2.06 (1H, d), 4.00 (3H, s), 4.06 (3H, s), 4.85–4.95 (2H, m), 6.85 (1H, s), 7.13 (1H, q), 787 (1H, s), 9.97 (1H, s).

3-(1-Isopropoxycarbonyloxyethyl)-7,8-dimethoxy-4 (5H), 10-dioxo-3H-1,2,3-triazolo[4,5-c][1]benzazepine (compound substituted at 3-position).

$^1$H-NMR (CDCl$_3$): δ 1.21 (3H, d), 1.29 (3H, d), 2.12 (1H, d), 4.00 (3H, s), 4.01 (3H, s), 4.75–4.85 (2H, m), 6.57 (1H, s), 7.90 (1H, s), 7.91 (1H, q), 8.86 (1H, s).

Example 2

7,8-Dimethoxy-4 (5H), 10-dioxo-1-(pivaloyloxymethyl)-1H-1,2,3-triazolo[4,5-c][1] benzazepine (substituted at 1-position), 7,8-dimethoxy-4(5H), 10-dioxo-2-(pivaloyloxymethyl)-2H-1,2,3-triazolo[4,5-c][1]benzazepine (substituted at 2-position), and 7,8-dimethoxy-4(5H), 10-dioxo-3-(pivaloyloxymethyl)-3H-1,2,3-triazolo[4,5-c][1] benzazepine (substituted at 3-position).

The title compound (345 mg, 89%) was prepared as a mixture of three compounds from 7,8-dimethoxy-4(5H), 10-dioxo-1H-1,2,3-triazolo[4,5-c][1]benzazepine (Synthesis Example 1) (296 mg) in the same manner as in Example 1, except that pivaloyloxymethyl chloride and sodium iodide were used instead of 1-iodoethylisopropyl carbonate. This was purified by column chromatography on silica gel (hexane/ethyl acetate) to separate three isomers as yellow powders.

7,8-Dimethoxy-4(5H),10-dioxo-1-(pivaloyloxymethyl)-1H-1,2,3-triazolo[4,5-c][1]benzazepine (substituted at 1-position).

$^1$H-NMR (DMSO-d$_6$): δ 1.13 (9H, s), 3.85 (6H, s), 6.74 (2H, s), 7.18 (1H, s), 7.70 (1H, s), 11.48 (1H, s).

7,8-Dimethoxy-4(5H), 10-dioxo-2-(pivaloyloxymethyl)-2H-1,2,3-triazolo[4,5-c][1]benzazepine (substituted at 2-position).

$^1$H-NMR (DMSO-d$_6$) : δ 1.16 (9H, s), 3.84 (3H, s), 3.85 (3H, s), 6.54 (2H, s), 7.17 (1H, s), 7.64 (1H, s), 11.17 (1H, s).

7,8-Dimethoxy-4 (5H), 10-dioxo-3-(pivaloyloxymethyl)-3H-1,2,3-triazolo[4,5-c][1]benzazepine (substituted at 3-position).

$^1$H-NMR (DMSO-d$_6$) : δ 1.12 (9H, s), 3.83 (3H, s), 3.86 (3H, s), 6.70 (2H, s), 7.20 (1H, s), 7.59 (1H, s), 11.29 (1H, s).

Example 3

2-(Ethoxycarbonyloxymethyl)-7,8-dimethoxy-4 (5H), 10-dioxo-2H-1,2,3-triazolo[4,5-c][1] benzazepine (3a) Ethyl 5-(4,5-dimethoxy-2-nitrobenzoyl)-1H-1,2,3-triazole-4-carboxylate (Synthesis Example 2) (70 mg) and p-toluenesulfonic acid monohydrate (17 mg) were suspended in methylene chloride (10 ml) under an argon atmosphere. Paraformaldehyde (6 mg) was added thereto. The mixture was stirred at room temperature for 30 min. Pyridine (0.05 ml) and ethyl chloroformate (0.04 ml) were added thereto, and the mixture was stirred at room temperature for one hr. Further, pyridine (0.02 ml) and ethyl chloroformate (0.04 ml) were added thereto, and the mixture was stirred for 10 min. The solvent was evaporated under reduced pressure. Ethyl acetate (15 ml) and a saturated aqueous sodium hydrogencarbonate solution (10 ml) were added thereto, followed by separation. The organic layer was washed with a saturated aqueous sodium hydrogencarbonate solution (10 ml) and saturated brine solution (10 ml) in that order and dried over anhydrous magnesium sulfate. The solvent was evaporated under reduced pressure to give ethyl 2-(ethoxycarbonyloxymethyl)-5-(4,5-dimethoxy-2-nitrobenzoyl)-2H-1,2,3-triazole-4-carboxylate as a light yellow foam (48 mg, 53%).

$^1$H-NMR (CDCl$_3$): δ 1.31 (3H, t), 1.44 (3H, t), 4.01 (3H, s), 4.03 (3H, s), 4.25 (2H, q), 4.49 (2H, q), 6.21 (2H, s), 7.02 (1H, s), 7.66 (1H, s). EIMS: m/z 452 (M$^+$).

(3b) Ethyl 2-(ethoxycarbonyloxymethyl)-5-(4,5-dimethoxy-2-nitrobenzoyl)-2H-1,2,3-triazole-4-carboxylate (45 mg) prepared in step (3a) was dissolved in ethyl acetate (1 ml). Palladium hydroxide (15 mg) was added to the solution. The mixture was stirred in a hydrogen atmosphere at room temperature for 15 hr. The reaction solution was filtered through Celite. The filtrate was concentrated under reduced pressure to give ethyl 5-(2-amino-4,5-dimethoxybenzoyl)-2-(ethoxycarbonyloxymethyl)-2H-1,2,3-triazole-4-carboxylate as a yellow oil (40 mg, 95%).

$^1$H-NMR (CDCl$_3$): δ 1.27 (3H, t), 1.33 (3H, t), 3.66 (3H, s), 3.90 (3H, s), 4.27 (2H, q), 4.34 (2H, q), 6.15 (1H, s), 6.38 (2H, s), 6.49 (2H, brs), 6.76 (1H, s). EIMS: m/z 422 (M$^+$).

(3c) Ethyl 5-(2-amino-4,5-dimethoxybenzoyl)-2-(ethoxycarbonyloxymethyl)-2H-1,2,3-triazole-4-carboxylate (40 mg) prepared in step (3b) was dissolved in acetic acid (2 ml). The solution was stirred at 100° C. for 2 hr. After the solution was allowed to cool, the solvent was evaporated under reduced pressure. Water was added to the residue. The resultant precipitate was collected by filtration, washed with saturated aqueous sodium hydrogencarbonate solution and water, and dried to give the title compound as a yellow crystal powder (20 mg, 56%).

$^1$H-NMR (DMSO-d$_6$): δ 1.23 (3H, t), 3.84 (3H, s), 3.86 (3H, s), 4.22 (2H, q), 6.56 (2H, s), 7.18 (1H, s), 7.65 (1H, s), 11.2 (1H, brs) EIMS: m/z 376 (M$^+$).

Example 4

2-(Isobutoxycarbonyloxymethyl)-7,8-dimethoxy-4 (5H),10-dioxo-2H-1,2,3-triazolo[4,5-c][1] benzazepine (4a) In the same manner as in Example 3 (3a), provided that isobutyl chloroformate was used instead of ethyl chloroformate, ethyl 2-(isobutoxycarbonyloxymethyl)-5-(4,5-dimethoxy-2-nitrobenzoyl)-2H-1,2,3-triazole-4-carboxylate (172 mg, 90%) was prepared as a light yellow oil from ethyl 5-(4,5-dimethoxy-2-nitrobenzoyl)-1H-1,2,3-triazole-4-carboxylate (Synthesis Example 2) (140 mg).

$^1$H-NMR (CDCl$_3$): δ 0.92–0.96 (6H, m), 1.44 (3H, t), 1.93–2.04 (1H, m), 3.90–3.98 (2H, m), 4.00 (3H, s), 4.03 (3H, s), 4.50 (2H, q), 6.21 (2H, s), 7.01 (1H, s), 7.65 (1H, s). EIMS: m/z 480 (M$^+$).

(4b) In the same manner as in Example 3 (3b), ethyl 5-(2-amino-4,5-dimethoxybenzoyl-2-(isobutoxycarbonyloxymethyl)-2H-1,2,3-triazole-4-carboxylate (148 mg, 94%) was prepared as a yellowish brown oil from ethyl 2-(isobutoxycarbonyloxymethyl)-5-(4,5-dimethoxy-2-nitrobenzoyl)-2H-1,2,3-triazole-4-carboxylate (170 mg) prepared in step (4a).

$^1$H-NMR (CDCl$_3$): δ 0.93–0.96 (6H, m), 1.27 (3H, t), 1.95–2.02 (1H, m), 3.65 (3H, s), 3.90 (3H, s), 3.90 (3H, s), 3.99 (2H, d), 4.34 (2H, q), 6.15 (1H, s), 6.38 (2H, s), 6.49 (2H, brs), 6.76 (1H, s). EIMS: m/z 450 (M$^+$).

(4c) In the same manner as in Example 3 (3c), the title compound (45 mg, 31%) was prepared as a yellow powder from ethyl 5-(2-amino-4,5-dimethoxybenzoyl)-2-(isobutoxycarbonyloxymethyl)-2H-1,2,3-triazole-4-carboxylate (143 mg) prepared in step (4b).

$^1$H-NMR (DMSO-d$_6$): δ 0.87 (3H, d), 0.89 (3H, d), 1.88–1.95 (1H, m), 3.83 (3H, s), 3.85 (3H, s), 3.98 (2H, dd), 6.57 (2H, s), 7.18 (1H, s), 7.65 (1H, s), 11.16 (1H, brs). EIMS: m/z 4d4 (M$^+$).

Example 5

2-(Hexyloxycarbonyloxymethyl)-7,8-dimethoxy-4 (5H), 10-dioxo-2H-1,2,3-triazolo[4,5-c][1] benzazepine (5a) In the same manner as in Example 3 (3a), provided that hexyl chloroformate (0.2 ml) was used instead of ethyl chloroformate, ethyl 2-(hexyloxycarbonyloxymethyl)-5-(4,5-dimethoxy-2-nitrobenzoyl)-2H-1,2,3-triazole-4-carboxylate (168 mg, 83%) was prepared as a light yellow oil from ethyl 5-(4,5-dimethoxy-2-nitrobenzoyl)-1H-1,2,3-triazole-4-carboxylate (Synthesis Example 2) (140 mg).

$^1$H-NMR (CDCl$_3$): δ 0.86–0.90 (3H, m), 1.20–1.32 (6H, m), 1.44 (3H, t), 1.58–1.67 (2H, m)r, 4.00 (.3H, s), 4.03 (3H, s), 4.18 (2H, t), 4.50 (2H, q), 6.20 (2H, s), 7.01 (1H, s), 7.65 (1H, s). EIMS: m/z 508 (M$^+$).

(5b) In the same manner as in Example 3 (3b), ethyl 5-(2-amino-4,5-dimethoxybenzoyl)-2-(hexyloxycarbonyloxymethyl)-2H-1,2,3-triazole-4-carboxylate (149 mg, 96%) was prepared as a yellow oil from ethyl 2-(hexyloxycarbonyloxymethyl)-5-(4,5-dimethoxy-2-nitrobenzoyl)-2H-1,2,3-triazole-4-carboxylate (165 mg) prepared in step (5a).

$^1$H-NMR (CDCl$_3$): δ 0.88 (3H, t), 1.27 (3H, t), 1.31–1.43 (6H, m), 1.62–1.69 (2H, m), 3.66 (3H, s), 3.90 (3H, s), 4.20 (2H, t), 4.34 (2H, q), 6.15 (1H, s), 6.37 (2H, s), 6.50 (2H, brs), 6.77 (1H, s). EIMS: m/z 478 (M$^+$).

(5c) In the same manner as in Example 3 (3c), the title compound (88 mg, 68%) was prepared as yellow powder from ethyl 5-(2-amino-4,5-dimethoxybenzoyl)-2-(hexyloxycarbonyloxymethyl)-2H-1,2,3-triazole-4-carboxylate (145 mg) prepared in step (3b).

$^1$H-NMR (DMSO-d$_6$): δ 0.83 (3H, t), 1.24–1.28 (6H, m), 1.58–1.62 (2H, m), 3.84 (3H, s), 3.86 (3H, s), 4.17 (2H, t), 6.56 (2H, s), 7.18 (1H, s), 7.65 (1H, s), 11.16 (1H, brs). EIMS: m/z 432 (M$^+$).

Example 6

2-(n-Butoxycarbonyloxymethyl)-7,8-dimethoxy-4 (5H), 10-dioxo-2H-1,2,3-triazolo[4,5-c][1] benzazepine (6a) In the same manner as in Example 3 (3a), provided that n-butyl chloroformate (0.26 ml) was used instead of ethyl chloroformate, ethyl 2-(n-butoxycarbonyloxymethyl)-5-(4,5-dimethoxy-2-nitrobenzoyl)-2H-1,2,3-triazole-4-carboxylate (166 mg, 86%) was prepared as a yellow oil from ethyl 5-(4,5-dimethoxy-2-nitrobenzoyl)-1H-1,2,3-triazole-4-carboxylate (Synthesis Example 2) (140 mg).

$^1$H-NMR (CDCl$_3$): δ 0.94 (3H, t), 1.35–1.41 (2H, m), 1.44 (3H, t), 1.61–1.68 (2H, m), 4.00 (3H, s), 4.03 (3H, s), 4.19 (2H, t), 4.50 (2H, q), 6.20 (2H, s), 7.02 (1H, s), 7.66 (1H, s). EIMS: m/z 480 (M$^+$).

(6b) In the same manner as in Example 3 (3b), ethyl 5-(2-amino-4,5-dimethoxybenzoyl)-2-(n-butoxycarbonyloxymethyl)-2H-1,2,3-triazole-4-carboxylate (150 mg, 100%) was prepared as a yellow oil from ethyl 2-(n-butoxycarbonyloxymethyl)-5-(4,5-dimethoxy-2-nitrobenzoyl)-2H-1,2,3-triazole-4-carboxylate (160 mg) prepared in step (6a).

$^1$H-NMR (CDCl$_3$): δ 0.83 (3H, t), 1.27 (3H, t), 1.36–1.42 (2H, m), 1.63–1.69 (2H, m), 3.66 (3H, s), 3.91 (3H, s), 4.20 (2H, t), 4.34 (2H, q), 6.15 (1H, s), 6.38 (2H, s), 6.50 (2H, brs), 6.76 (1H, s). EIMS: m/z 450 (M$^+$).

(6c) In the same manner as in Example 3 (3c), the title compound (78 mg, 64%) was prepared as yellow powder from ethyl 5-(2-amino-4,5-dimethoxybenzoyl)-2-(n-butoxycarbonyloxymethyl)-2H-1,2,3-triazole-4-carboxylate (150 mg) prepared in step (6b).

$^1$H-NMR (DMSO-d$_6$): δ 0.87 (3H, t), 1.28–1.36 (2H, m), 1.55–1.62 (2H, m), 3.84 (3H, s), 3.85 (3H, s), 4.18 (2H, t), 6.56 (2H, s), 7.17 (1H, s), 7.64 (1H, s), 11.16 (1H, brs). EIMS: m/z 404 (M$^+$).

Example 7

2-(Isopropoxycarbonyloxymethyl)-7,8-dimethoxy-4 (5H), 10-dioxo-2H-1,2,3-triazolo[4,5-c][1] benzazepine (7a) In the same manner as in Example 3 (3a), provided that 1M toluene solution (6 ml) of isopropyl chloroformate was used instead of ethyl chloroformate, a 2:1 mixture (906 mg) of ethyl 2-(isopropoxycarbonyloxymethyl)-5-(4,5-dimethoxy-2-nitrobenzoyl)-2H-1,2,3-triazole-4-carboxylate and ethyl 2-(isopropoxycarbonyl)-5-(4,5-dimethoxy-2-nitrobenzoyl)-2H-1,2,3-triazole-4-carboxylate was prepared as a light yellow foam from ethyl 5-(4,5-dimethoxy-2-nitrobenzoyl)-1H-1,2,3-triazole-4-carboxylate (Synthesis Example 2) (700 mg).

$^1$H-NMR (CDCl$_3$): δ 1.29 (6H, d), 1.43–1.50 (3H, m), 4.01–4.04 (6H, m), 4.47–4.55 (2/3H, m), 5.28–5.35 (1/3H, m), 6.19 (4/3H, s), 7.01 (2/3H, s), 7.04 (1/3H, s), 7.65 (2/3H, s), 7.67 (1/3H, s).

(7b) The 2:1 mixture (870 mg) of ethyl 2-(isopropoxycarbonyloxymethyl)-5-(4,5-dimethoxy-2-nitrobenzoyl)-2H-1,2,3-triazole-4-carboxylate and ethyl 2-(isopropoxycarbonyl)-5-(4,5-dimethoxy-2-nitrobenzoyl)-2H-1,2,3-triazole-4-carboxylate prepared in step (7a) was reacted in the same manner as in Example 3 (3a). The reaction product was purified by column chromatography on silica gel (hexane/ethyl acetate) to give a 4:1 mixture (612 mg) of ethyl 5-(2-amino-4,5-dimethoxybenzoyl)-2-

(isopropoxycarbonyloxymethyl)-2H-1,2,3-triazole-4-carboxylate and ethyl 5-(2-amino-4,5-dimethoxybenzoyl)-2-(isopropoxycarbonyl)-2H-1,2,3-triazole-4-carboxylate as a light yellow foam.

$^1$H-NMR (CDCl$_3$): δ 1.25–1.30 (3H, m), 1.31 (6H, d), 3.66 (3H, s), 3.90 (3H, s), 4.32–4.39 (2H, m), 4.90–4.96 (4/5H, m), 5.30–5.46 (1/5H, m), 6.14 (1H, s), 6.36 (8/5H, s), 6.49 (2H, brs), 6.77 (1H, s).

(7c) In the same manner as in Example 3 (3c), the title compound (450 mg, 75%) was prepared as light yellow powder from the 4:1 mixture (610 mg) of ethyl 5-(2-amino-4,5-dimethoxybenzoyl)-2-(isopropoxycarbonyloxymethyl)-2H-1,2,3-triazole-4-carboxylate and ethyl 5-(2-amino-4,5-dimethoxybenzoyl)-2-(isopropoxycarbonyl)-2H-1,2,3-triazole-4-carboxylate prepared in step (7b).

$^1$H-NMR (DMSO-d$_6$): δ 1.25 (6H, d), 3.84 (3H, s), 3.85 (3H, s), 4.83–4.88 (1H, m), 6.66 (2H, s), 7.18 (1H, s), 7.65 (1H, s), 11.18 (1H, s).

Example 8

2-(Benzoyloxymethyl)-7,8-dimethoxy-4 (5H), 10-dioxo-2H- 1,2,3-triazolo[4,5-c][1]benzazepine (8a) In the same manner as in Example 3 (3a), provided that benzoyl chloride (0.28 ml) was used instead of ethyl chloroformate, a crude product of ethyl 2-(benzoyloxymethyl)-5-(4,5-dimethoxy-2-nitrobenzoyl)-2H-1,2,3-triazole-4-carboxylate (230 mg) was prepared as a light yellow oil from ethyl 5-(4,5-dimethoxy-2-nitrobenzoyl)-1H-1,2,3-triazole-4-carboxylate (Synthesis Example 2) (210 mg)

(8b) In the same manner as in Example 3 (3b), a crude product of ethyl 5-(2-amino-4,5-dimethoxybenzoyl)-2-(benzoyloxymethyl)-2H-1,2,3-triazole-4-carboxylate (195 mg) was prepared as a yellow oil from the crude product of 2-(benzoyloxymethyl)-5-(4,5-dimethoxy-2-nitrobenzoyl)-2H-1,2,3-triazole-4-carboxylate (230 mg) prepared in step (8a).

(8c) In the same manner as in Example 3 (3c), the title compound (40 mg, yield in three steps 56%) was prepared as yellow powder from the crude product of ethyl 5-(2-amino-4,5-dimethoxybenzoyl)-2-(benzoyloxymethyl)-2H-1,2,3-triazole-4-carboxylate prepared in step (8b).

$^1$H-NMR (DMSO-d$_6$): δ 3.82 (3H, 5), 3.84 (3H, s), 6.80 (2H, s), 7.14 (1H, s), 7.56 (2H, t), 7.62 (1H, s), 7.72 (1H, t), 8.01 (2H, d), 11.14 (1H, brs).

Example 9

2-(Lauroyloxymethyl)-7,8-dimethoxy-4 (5H), 10-dioxo-2H-1,2,3-triazolo[4,5-c][1]benzazepine (9a) In the same manner as in Example 3 (3a), provided that lauroyl chloride (0.37 ml) was used instead of ethyl chloroformate. Thus, ethyl 2-(lauroyloxymethyl)-5-(4,5-dimethoxy-2-nitrobenzoyl)-2H-1,2,3-triazole-4-carboxylate (190 mg, 85%) was prepared as a light yellow oil from ethyl 5-(4,5-dimethoxy-2-nitrobenzoyl)-1H-1,2,3-triazole-4-carboxylate (Synthesis Example 2) (140 mg).

$^1$H-NMR (CDCl$_3$): δ 0.88 (3H, t), 1.20–1.30 (16H, m), 1.44 (3H, t), 1.55–1.65 (2H, m), 2.35 (2H, t), 4.01 (3H, s), 4.03 (3H, s), 4.50 (2H, q), 6.19 (2H, s), 7.03 (1H, s), 7.65 (1H, s). EIMS: m/z 562 (M$^+$).

(9b) In the same manner as in Example 3 (3b), ethyl 5-(2-amino-4,5-dimethoxybenzoyl)-2-(lauroyloxymethyl)-2H-1,2,3-triazole-4-carboxylate (157 mg, 96%) was prepared as a yellow oil from ethyl 2-lauroyloxymethyl-5-(4,5-dimethoxy-2-nitrobenzoyl)-2H-1,2,3-triazole-4-carboxylate (172 mg) prepared in step (9a).

$^1$H-NMR (CDCl$_3$): δ 0.86 (3H, t), 1.24–1.29 (16H, m), 1.27 (3H, t), 1.55–1.65 (2H, m), 2.38 (2H, t), 3.66 (3H, s), 3.90 (3H, s), 4.34 (2H, q), 6.15 (1H, s), 6.36 (2H, s), 6.50 (2H, brs), 6.75 (1H, s). EIMS: m/z 532 (M$^+$).

(9c) In the same manner as in Example 3 (3c), the title compound (95 mg, 70%) was prepared as a yellow powder from ethyl 5-(2-amino-4,5-dimethoxybenzoyl)-2-(lauroyloxymethyl)-2H-1,2,3-triazole-4-carboxylate (150 mg) prepared in step (9b).

$^1$H-NMR (DMSO-d$_6$): δ 0.83 (3H, t), 1.15–1.20 (16H, m), 1.51 (2H, ml, 2.41 (2H, t), 3.84 (3H, s) 3.85 (3H, s), 6.54 (2H, s), 7.18 (1H, s), 7.65 (1H, s), 11.17 (1H, brs). EIMS: m/z 486 (M$^+$).

Example 10

7,8-Dimethoxy-4 (5H), 10-dioxo-2-(palmitoyloxymethyl)-2H-1,2,3-triazolo[4,5-c][1]benzazepine (10a) In the same manner as in Example 3 (3a), provided that palmitoyl chloride (0.49 ml) was used instead of ethyl chloroformate, ethyl 5-(4,5-dimethoxy- 2-nitrobenzoyl)-2-(palmitoyloxymethyl)-2H-1,2,3-triazole-4-carboxylate (194 mg, 79%) was prepared as a light yellow oil from ethyl 5-(4,5-dimethoxy-2-nitrobenzoyl)-1H-1,2,3-triazole-4-carboxylate (Synthesis Example 2) (140 mg).

$^1$H-NMR (CDCl$_3$): δ 0.88 (3H, t), 1.20–1.30 (24H, m), 1.44 (3H, t), 1.55–1.59 (2H, m), 2.35 (2H, t), 4.01 (3H, s), 4.03 (3H, s), 4.50 (2H, q), 6.19 (2H, s), 7.03 (1H, s), 7.65 (1H, s). EIMS: m/z 618 (M$^+$).

(10b) In the same manner as in Example 3 (3b), ethyl 5-(2-amino-4,5-dimethoxybenzoyl)-2-(palmitoyloxymethyl)-2H-1,2,3-triazole-4-carboxylate (158 mg, 88%) was prepared as a yellow oil from ethyl 5-(4,5-dimethoxy-2-nitrobenzoyl)-2-(palmitoyloxymethyl)-2H-1,2,3-triazole-4-carboxylate (190 mg) prepared in step (10a).

$^1$H-NMR (CDCl$_3$): δ 0.88 (3H, t), 1.24–1.29 (24H, m), 1.27 (3H, t), 1.60–1.65 (2H, m), 2.38 (2H, t), 3.66 (3H, s), 3.91 (3H, s), 4.34 (2H, q), 6.15 (1H, s), 6.36 (2H, s), 6.50 (2H, brs), 6.76 (1H, s). EIMS: m/z 588 (M$^+$).

(10c) In the same manner as in Example 3 (3c), the title compound (117 mg, 82%) was prepared as yellow powder from ethyl 5-(2-amino-4,5-dimethoxybenzoyl)-2-(palmitoyloxymethyl)-2H-1,2,3-triazole-4-carboxylate (155 mg) prepared in step (10b).

$^1$H-NMR (DMSO-d$_6$): δ 0.84 (3H, t), 1.14–1.21 (24H, m), 1.51 (2H, m), 2.41 (2H, t), 3.84 (3H, s), 3.85 (3H, s), 6.54 (2H, s), 7.18 (1H, s), 7.65 (1H, s), 11.18 (1H, brs). EIMS: m/z 542 (M$^+$).

Example 11

2-(4-Chlorobutyryloxymethyl)-7,8-dimethoxy-4 (5H), 10-dioxo-2H-1,2,3-triazolo[4,5-c][1]benzazepine (11a) In the same manner as in Example 3 (3a), provided that 4-chlorobutyryl chloride (0.36 ml) was used instead of ethyl chloroformate, ethyl 2-(4-chlorobutyryloxymethyl)-5-(4,5-dimethoxy-2-nitrobenzoyl)-2H-1,2,3-triazole-4-carboxylate (312 mg, 80%) was prepared as a light yellow foam from ethyl 5-(4,5-dimethoxy-2-nitrobenzoyl)-1H-1,2,3-triazole-4-carboxylate (Synthesis Example 2) (280 mg).

¹H-NMR (CDCl₃): δ 1.45 (3H, t), 2.05 2.14 (2H, m), 2.55–2.64 (2H, m), 3.55–3.60 (2H, m), 4.02 (3H, s), 4.03 (3H, s), 4.50 (2H, q), 6.22 (2H, s), 7.03 (1H, s), 7.65 (1H, s). EIMS: m/z 484 (M⁺).

(11b) In the same manner as in Example 3 (3b), ethyl 5-(2-amino-4,5-dimethoxybenzoyl)-2-(4-chlorobutyryloxymethyl)-2H-1,2,3-triazole-4-carboxylate (270 mg, 91%) was prepared as a yellow oil from ethyl 2-(4-chlorobutyryloxymethyl)-5-(4,5-dimethoxy-2-nitrobenzoyl)-2H-1,2,3-triazole-4-carboxylate (315 mg).

¹H-NMR (CDCl₃): δ 1.24–1.29 (3H, m), 2.12 (2H, m), 2.60 (2H, t), 3.58–3.61 (2H, m), 3.65 (3H, s), 3.91 (3H, s), 4.34 (2H, q), 6.15 (1H, s), 6.38 (2H, s), 6.51 (2H, brs), 6.74 (1H, s). EIMS: m/z 454 (M⁺).

(11c) In the same manner as in Example 3 (3c), the title compound (180 mg, 74%) was prepared as yellow powder from ethyl 5-(2-amino-4,5-dimethoxybenzoyl)-2-(4-chlorobutyryloxymethyl-2H-1,2,3-triazole-4-carboxylate (270 mg).

¹H-NMR (DMSO-d₆): δ 1.96–2.03 (2H, m), 2.38 (2H, t), 3.66 (2H, t), 3.83 (3H, s), 3.85 (3H, s), 6.54 (2H, s), 7.15 (1H, s), 7.63 (1H, s), 11.14 (1H, brs). EIMS: m/z 408 (M⁺).

Example 12

2-(4-Aminobenzoyloxymethyl)-7,8-dimethoxy-4 (5H), 10-dioxo-2H-1,2,3-triazolo[4,5-c][1]benzazepine (12a) In the same manner as in Example 3 (3a), provided that p-nitrobenzoyl chloride (223 mg) was used instead of ethyl chloroformate, ethyl 5-(4,5-dimethoxy-2-nitrobenzoyl)-2-(4-nitrobenzoyloxymethyl)-2H-1,2,3-triazole-4-carboxylate (118 mg, 56%) was prepared as a light yellow foam from ethyl 5-(4,5-dimethoxy-2-nitrobenzoyl)-1H-1,2,3-triazble-4-carboxylate (Synthesis Example 2) (140 mg).

¹H-NMR (CDCl₃): δ 1.45 (3H, t), 4.00 (3H, s), 4.03 (3H, s), 4.51 (2H, q), 6.48 (2H, s), 7.06 (1H, s), 7.62 (1H, s), 8.20 (2H, d), 8.30 (2H, d). EIMS: m/z 529 (M⁺).

(12b) In the same manner as in Example 3 (3b), ethyl 5-(2-amino-4,5-dimethoxybenzoyl)-2-(4-aminobenzoyloxymethyl)-2H-1,2,3-triazole-4-carboxylate (100 mg, 98%) was prepared as a yellowish brown oil from ethyl 5-(4,5-dimethoxy-2-nitrobenzoyl)-2-(4-nitrobenzoyloxymethyl)-2H-1,2,3-triazole-4-carboxylate (115 mg) prepared in step (12b).

¹H-NMR (CDCl₃): δ 1.29 (3H, t), 3.54 (3H, s), 3.89 (3H, s), 4.15 (2H, brs), 4.33 (2H, q), 6.14 (1H, s), 6.40 (2H, brs), 6.56 (2H, s), 6.56–6.67 (2H, m), 6.76 (1H, s),7.83–7.91 (2H, m). EIMS: m/z 469 (M⁺).

(12c) In the same manner as in Example 3 (3c), the title compound (54 mg, 59%) was prepared as yellow powder from ethyl 5-(2-amino-4,5-dimethoxybenzoyl)-2-(4-aminobenzoyloxymethyl)-2H-1,2,3-triazole-4-carboxylate (102 mg) prepared in step (12b).

¹H-NMR (DMSO-d₆): δ 3.83 (3H, s), 3.85 (3H, s), 6.21 (2H, s), 6.56 (2H, d), 6.68 (2H, s), 7.16 (1H, s), 7.64 (1H, s), 7.67 (2H, d), 11.14 (1H, brs). EIMS: m/z 423 (M⁺).

Example 13

7,8-Dimethoxy-4(5H), 10-dioxo-2-(3-pyridylcarbonyloxymethyl)-2H-1,2,3-triazolo[4,5-c][1]benzazepine (13a) In the same manner as in Example 3 (3a), provided that thionyl chloride (0.06 ml) was used instead of ethyl chloroformate, ethyl 2-chloromethyl-5-(4,5-dimethoxy-2-nitrobenzoyl)-2H-1,2,3-triazole-4-carboxylate (146 mg, 92%) was prepared as a light yellow foam from ethyl 5-(4,5-dimethoxy-2-nitrobenzoyl)-1H-1,2,3-triazole-4-carboxylate (Synthesis Example 2) (140 mg).

¹H-NMR (CDCl₃): δ 1.45 (3H, t), 4.00 (3H, s), 4.03 (3H, s), 5.98 (2H, s), 7.04 (1H, s), 7.66 (1H, s). EIMS: m/z 398 (M⁺).

(13b) In the same manner as in Example 3 (3b), ethyl 5-(2-amino-4,5-dimethoxybenzoyl)-2-chloromethyl-2H-1,2,3-triazole-4-carboxylate (120 mg, 93%) was prepared as a light yellow oil from ethyl 2-chloromethyl-5-(4,5-dimethoxy-2-nitrobenzoyl)-2H-1,2,3-triazole-4-carboxylate (140 mg) prepared in step (13a).

¹H-NMR (CDCl₃): δ 1.28 (3H, t), 3.66 (3H, s), 3.91 (3H, s), 4.34 (2H, q), 6.15 (3H, s), 6.42 (2H, brs), 6.73 (1H, s). EIMS: m/z 368 (M⁺).

(13c) In the same manner as in Example 3 (3c), 2-chloromethyl-7,8-dimethoxy-4 (5H), 10-dioxo-2H-1,2,3-triazolo[4,5-c][1]benzazepine (66 mg, 66%) was prepared as light yellow powder form ethyl 5-(2-amino-4,5-dimethoxybenzoyl)-2-chloromethyl-2H-1,2,3-triazole-4-carboxylate (114 mg) prepared in step (13b).

¹H-NMR (DMSO-d₆): δ 3.84 (3H, s) 3.85 (3H, s), 6.68 (2H, s), 7.17 (1H, s), 7.64 (1H, s), 11.16 (1H, brs) EIMS: m/z 322 (M⁺).

(13d) 2-Chloromethyl-7,8-dimethoxy-4(5H), 10-dioxo-2H-1,2,3-triazolo[4,5-c][1]benzazepine (47 mg) prepared in step (13c) was dissolved in N,N-dimethylformamide (5 ml). Tetra-n-butylammonium bromide (10.5 mg), nicotinic acid (20 mg), and potassium carbonate (34 mg) were added to the solution. The mixture was stirred at 70° C. for 1.5 hr. After the mixture was allowed to stand for cooling, the reaction solution was post-treated by a conventional method and subjected to separation and purification to give the title compound (41 mg, 67%) as a light yellow powder.

¹H-NMR (DMSO-d₆): δ 3.84 (3H, s), 3.85 (3H, s), 6.83 (2H, s), 7.16 (1H, s), 7.60 (1H, dd), 7.64 (1H, s), 8.35 (1H, ddd), 8.86 (1H, dd), 9.12 (1H, d), 11.16 (1H, brs). FABMS: m/z 410 (M⁺+1).

Example 14

7,8-Dimethoxy-4 (5H), 10-dioxo-2-(4-pyridylcarbonyloxymethyl)-2H-1,2,3-triazolo[4,5-c][1]benzazepine (14a) In the same manner as in Example 13 (13d), provided that isonicotinic acid (24 mg) was used instead of nicotinic acid, the title compound (30 mg, 46%) was prepared as light yellow powder from 2-chloromethyl-7,8-dimethoxy-4 (5H), 10-dioxo-2H-1,2,3-triazolo[4,5-c][1]benzazepine (52 mg) prepared in step (13c).

¹H-NMR (DMSO-d₆): δ 3.83 (3H, s), 3.85 (3H, s), 6.84 (2H, s), 7.17 (1H, s), 7.64 (1H, s), 7.87 (2H, d), 8.83 (2H, d), 11.18 (1H, brs). FABMS: m/z 410 (M⁺+1).

Example 15

2-(1-Isobutyryloxyethyl)-7,8-dimethoxy-4 (5H), 10-dioxo-2H-1,2,3-triazolo[4,5-c][1]benzazepine (15a) In the same manner as in Example 3 (3a), provided that acetaldehyde (0.13 ml) and thionyl chloride (0.7 ml) were used respectively instead of paraformaldehyde and ethyl chloroformate, ethyl 2-(1-chloroethyl)-5-(4,5-dimethoxy-2-nitrobenzoyl)-2H-1,2,3-triazole-4-carboxylate (736 mg, 74%) was prepared as a light yellow foam from ethyl 5-(4,5-dimethoxy-2-nitrobenzoyl)-1H-1,2,3-triazole-4-carboxylate (Synthesis Example 2) (840 mg).

$^1$H-NMR (CDCl$_3$): δ 1.45 (3H, t), 2.14 (3H, d), 4.01 (3H, s), 4.03 (3H, s), 4.50 (2H, q), 6.42 (1H, q), 7.06 (1H, s), 7.64 (1H, s). LCMS: m/z 413 (M$^+$+1).

(15b) In the same manner as in Example 3 (3b), ethyl 5-(2-amino-4,5-dimethoxybenzoyl)-2-(1-chloroethyl)-2H-1,2,3-triazole-4-carboxylate (545 mg, 80%) was prepared as a light yellow foam from ethyl 2-(1-chloroethyl)-5-(4,5-dimethoxy-2-nitrobenzoyl)-2H-1,2,3-triazole-4-carboxylate (735 mg) prepared in step (15a).

$^1$H-NMR (CDCl$_3$): δ 1.28 (3H, t), 2.28 (3H, d), 3.65 (3H, s), 3.91 (3H, s), 4.35 (2H, q), 6.15 (1H, s), 6.51 (2H, brs), 6.6 (1H, q), 6.75 (1H, s). LCMS: m/z 383 (M$^+$+1).

(15c) In the same manner as in Example 3 (3c), 2-(1-chloroethyl)-7,8-dimethoxy-4(5H), 10-dioxo-2H-1,2,3-triazolo[4,5-c][1]benzazepine (426 mg, 90%) was prepared as a light yellow powder from ethyl 5-(2-amino-4,5-dimethoxybenzoyl)-2-(1-chloroethyl)-2H-1,2,3-triazole-4-carboxylate (540 mg) prepared in step (15b).

$^1$H-NMR (DMSO-d$_6$): δ 2.20 (3H, d), 3.84 (3H, s), 3.86 (3H, s), 7.18 (1H, s), 7.21 (1H, q), 7.65 (1H, s), 11.19 (1H, s). FABMS: m/z. 337 (M$^+$+1).

(15d) In the same manner as in Example 13 (13d), provided that isobutyric acid (0.023 ml) was used instead of ethyl chloroformate. Thus, the title compound (32 mg, 41%) was prepared as a light yellow powder from 2-(1-chloroethyl)-7,8-dimethoxy-4 (5H), 10-dioxo-2H-1,2,3-triazolo[4,5-c][1]benzazepine (67 mg) prepared in step (15c).

$^1$H-NMR (DMSO-d$_6$): δ 1.05 (3H, d), 1.10 (3H, d), 1.88 (3H, d), 2.60–2.67 (1H, m), 3.84 (3H, s) 3.85 (3H, s), 7.18 (1H, s), 7.23 (1H, q), 7.65 (1H, s), 11.16 (1H, brs). LCMS: m/z 389 (M$^+$+1).

Example 16

7,8-Dimethoxy-2-(4-methoxyphenylacetoxymethyl)-4 (5H), 10-dioxo-2H-1,2,3-triazolo[4,5-c][1]benzazepine (16a) In the same manner as in Example 3 (3a), provided that a methylene chloride solution of acid chloride prepared from p-methoxyphenylacetic acid (400 mg) and thionyl chloride (0.88 ml) was used instead of ethyl chloroformate, ethyl 5(4,5-dimethoxy-2-nitrobenzoyl)-2-(4-methoxyphenylacetoxymethyl)-2H-1,2,3-triazole-4-carboxylate (210 mg, 66%) was prepared as a light yellow oil from ethyl 5-(4,5-dimethoxy-2-nitrobenzoyl)-1H-1,2,3-triazole-4-carboxylate (Synthesis Example 2) (210 mg).

$^1$H-NMR (CDCl$_3$): δ 1.45 (3H, t), 3.61 (2H, s), 3.79 (3H, s), 4.00 (3H, s), 4.03 (3H, s), 4.50 (2H, q), 6.20 (2H, s), 6.84 (2H, d), 7.03 (1H, s), 7.14 (2H, d), 7.64 (1H, s). LCMS: m/z 528 (M$^+$).

(16b) In the same manner as in Example 3 (3b), ethyl 5-(2-amino-4,5-dimethoxybenzoyl)-2-(4-methoxyphenylacetoxymethyl)-2H-1,2,3-triazole-4-carboxylate (180 mg, 95%) was prepared as a yellow oil from ethyl 5-(4,5-dimethoxy-2-nitrobenzoyl)-2-(4-methoxyphenylacetoxymethyl)-2H-1,2,3-triazole-4-carboxylate (200 mg) prepared in step (16a).

$^1$H-NMR (CDCl$_3$): δ 1.28 (3H, t), 3.60 (3H, s), 3.64 (2H, s), 3.79 (3H, s), 3.91 (3H, s), 4.35 (2H, q), 6.15 (1H, s), 6.37 (2H, s), 6.50 (2H, brs), 6.73 (1H, s), 6.84 (2H, d), 7.17 (2H, d). LCMS: m/z 499 (M$^+$+1).

(16c) In the same manner as in Example 3 (3c), the title compound (118 mg, 75%) was prepared as a yellow powder from ethyl 5-(2-amino-4,5-dimethoxybenzoyl)-2-(4-methoxyphenylacetoxymethyl)-2H-1,2,3-triazole-4-carboxylate (175 mg) prepared in step (16b).

$^1$H-NMR (DMSO-d$_6$): δ 3.71 (3H, s), 3.74 (3H, s), 3.85 (3H, s), 6.56 (2H, s), 6.85 (2H, d), .7.18 (1H, s), 7.18 (2H, d), 7.65 (1H, s), 11.17 (1H, brs) LCMS: m/z 453 (M$^+$+1).

Example 17

7,8-Dimethoxy-2-(N-(2-(N,N-dimethylamino)ethyl) carbamoyl oxymethyl)-4 (5H), 10-dioxo-2H-1,2,3-triazolo[4,5-c][1]benzazepine (17a) In the same manner as in Example 3 (3a), provided that p-nitrophenyl chloroformate (806 mg) was used instead of ethyl chloroformate, ethyl 5-(4,5-dimethoxy-2-nitrobenzoyl)-2-(4-nitrophenoxycarbonyloxymethyl)-2H-1,2,3-triazole-4-carboxylate (778 mg, 71%) was prepared from ethyl 5-(4,5-dimethoxy-2-nitrobenzoyl)-1H-1,2,3-triazole-4-carboxylate (Synthesis Example 2) (700 mg).

$^1$H-NMR (CDCl$_3$): δ 1.46 (3H, t), 4.01 (3H, s), 4.03 (3H, s), 4.52 (2H, q), 6.34 (2H, s), 7.05 (1H, s), 7.40 (2H, d), 7.64 (1H, s), 8.30 (2H, d).

(17b) N,N-dimethylethylenediamine (0.02 ml) was added to a solution of ethyl 5-(4,5-dimethoxy-2-nitrobenzoyl)-2-(4-nitrophenoxycarbonyloxymethyl)-2H-1,2,3-triazole-4-carboxylate (83 mg), prepared in step (17a), in methylene chloride solution (1.5 ml) under ice cooling. The mixture was stirred for 2 hr. The reaction solution was post-treated by a conventional method and subjected to separation and purification to give ethyl 5-(4,5-dimethoxy-2-nitrobenzoyl)-2-(N-(2-(N,N-dimethylamino)ethyl)carbamoyloxymethyl)-2H-1,2,3-triazole-4-carboxylate (64 mg, 85%).

$^1$H-NMR (CDCl$_3$): δ 1.43 (3H, t), 2.21 (6H, s), 2.41 (2H, t), 3.20–3.30 (2H, m), 4.00 (3H, s), 4.03 (3H, s), 4.49 (2H, q), 5.49 (1H, s), 6.18 (2H, s), 7.02 (1H, s), 7.65 (1H, s).

(17c) In the same manner as in Example 3 (3b), ethyl 5-(2-amino-4,5-dimethoxybenzoyl)-2-(N-(2-(N,N-dimethylamino)ethyl) carbamoyloxymethyl)-2H-1,2,3-triazole-4-carboxylate (56 mg, 100%) was prepared from ethyl 5-(4,5-dimethoxy-2-nitrobenzoyl)-2-(N-(2-(N,N-dimethylamino)ethyl)carbamoyloxymethyl)-2H-1,2,3-triazole-4-carboxylate (59 mg) prepared in step (17b).

$^1$H-NMR (CDCl$_3$): δ 1.25 (3H, t), 2.75 (6H, s), 3.05–3.15 (2H, m), 3.58–3.68 (2H, m), 3.67 (3H, s), 3.90 (3H, s), 4.32 (2H, q), 6.15 (1H, s), 6.37 (2H, s), 6.50 (2H, brs), 6.75 (1H, s). FABMS: m/z 465 (M$^+$+1).

(17d) In the same manner as in Example 3 (3c), the title compound (28 mg, 56%) was prepared as a white powder from ethyl 5-(2-amino-4,5-dimethoxybenzoyl)-2-(N-(2-(N,N-dimethylamino)ethyl)carbamoyloxymethyl)-2H-1,2,3-triazole-4-carboxylate (56 mg) prepared in step (17c).

$^1$H-NMR (DMSO-d$_6$): δ 2.77 (6H, s), 3.10–3.20 (2H, m), 3.35–3.45 (2H, m), 3.84 (3H, s), 3.86 (3H, s), 6.49 (2H, s), 7.20 (1H, s), 7.65 (1H, s), 7.98 (1H, t), 11.16 (1H, s). EIMS: m/z 418 (M$^+$+1).

Example 18

2-(Diethoxyphosphoryloxymethyl)-7,8-dimethoxy-4 (5H), 10-dioxo-2H-1,2,3-triazolo[4,5-c][1]benzazepine (18a) In the same manner as in Example 3 (3a), provided that diethyl chlorophosphate (0.12 ml) was used instead of ethyl chloroformate, a crude product of ethyl 2-(diethoxyphosphoryloxymethyl)-5-(4,5-dimethoxy-2-nitrobenzoyl)-2H-1,2,3-triazole-4-carboxylate (205 mg) was prepared from ethyl 5-(4,5-dimethoxy-2-nitrobenzoyl)-1H-1,2,3-triazole-4-carboxylate (Synthesis Example 2) (255 mg)

(18b) In the same manner as in Example 3 (3b), a crude product of ethyl 5-(2-amino-4,5-dimethoxybenzoyl)-2-(diethoxyphosphoryloxymethyl)-2H-1,2,3-triazole-4-carboxylate (186 mg) was prepared from the crude product of ethyl 2-(diethoxyphosphoryloxymethyl)-5-(4,5-dimethoxy-2-nitrobenzoyl)-2H-1,2,3-triazole-4-carboxylate (205 mg) prepared in step (18a).

(18c) In the same manner as in Example 3 (3c), the title compound (73 mg, yield in three steps 41%) was prepared from the crude product of ethyl 5-(2-amino-4,5-dimethoxybenzoyl)-2-(diethylphosphoryloxymethyl)-2H-1,2,3-triazole-4-carboxylate (179 mg) prepared in step (18b).

$^1$H-NMR (DMSO-d$_6$): δ 1.20 (6H, t), 3.84 (3H, s), 3.86 (3H, s), 4.00–4.10 (4H, m), 6.41 (2H, d), 7.19 (1H, s), 7.66 (1H, s), 11.18 (1H, s). FABMS: m/z 441 (M$^+$+1).

Example 19

7,8-Dimethoxy-4 (5H), 10-dioxo-2-(1-(3-pentyloxycarbonyloxy)propyl)- 2H-1,2,3-triazolo[4,5-c][1]benzazepine (19a) Ethyl 5-(4,5-dimethoxy-2-nitrobenzoyl)-1H-1,2,3-triazole-4-carboxylate (Synthesis Example 2) (2.1 g) and p-toluenesulfonic acid monohydrate (23 mg) were suspended in methylene chloride (60 ml) under an argon atmosphere. Propionaldehyde (0.48 ml) was added to the suspension. The mixture was stirred at room temperature for 10 min. 1,1'-Carbonyldiimidazole (1.07 g) was added thereto, and the mixture was stirred at room temperature for 10 min. The mixture was post-treated by a conventional method and then subjected to separation and purification to give ethyl 2(1-(imidazolylcarbonyloxy)propyl)-5-(4,5-dimethoxy-2-nitrobenzoyl)-2H-1,2,3-triazole-4-carboxylate (2.35 g, 78%) as a light yellow foam.

$^1$H-NMR (CDCl$_3$): δ 0.95 (3H, t), 1.45 (3H, t), 2.34–2.46 (2H, m), 4.01 (3H, s), 4.05 (3H, s), 4.50 (2H, q), 6.94 (1H, t), 7.08 (1H, m), 7.09 (1H, s), 7.39–7.40 (1H, m), 7.60 (1H, s), 8.12 (1H, m).

(19b) Ethyl 2-(l-(imidazolylcarbonyloxy)propyl)-5-(4,5-dimethoxy-2-nitrobenzoyl)-2H-1,2,3-triazole-4-carboxylate (377 mg) prepared in step (19a) was dissolved in toluene (12 ml). 3-Pentanol (1.6 ml) was added to the solution. The mixture was heated under reflux for 20 hr. The mixture was post-treated by a conventional method and subjected to separation and purification to give ethyl 5-(4,5-dimethoxy-2-nitrobenzoyl)-2-(1-(3-pentyloxycarbonyloxy) propyl)-2H-1,2,3-triazole-4-carboxylate (280 mg) as a light yellow oil.

$^1$H-NMR (CDCl$_3$) : δ 0.82–0.99 (9H, m), 1.44 (3H, t), 1.56–1.79 (4H, m), 2.18–2.29 (2H, m), 4.00 (3H, s), 4.03 (3H, s), 4.50 (2H, q), 4.54–4.60 (1H, m), 6. 62 (1H, t), 7.04 (1H, s), 7.62 (1H, s). LCMS: m/z 522 (M$^+$).

(19c) In the same manner as in Example 3 (3b), ethyl 5-(2-amino-4,5-dimethoxybenzoyl)-2-(1-(3-pentyloxycarbonyloxy)propyl)-2H-1,2,3-triazole-4-carboxylate (185 mg, yield in two steps 50%) was prepared as a light yellow oil from ethyl 5-(4,5-dimethoxy-2-nitrobenzoyl)-2-(1-(3-pentyloxycarbonyloxy)propyl)-2H-1,2,3-triazole-4-carboxylate (270 mg) prepared in step (19b).

$^1$H-NMR (CDCl$_3$): δ 0.85 (3H, t), 0.92 (3H, t), 0.97 (3H, t), 1.28 (3H, t), 1.57–1.67 (4H, m), 2.30–2.49 (2H, m), 3.64 (3H, s), 3.90 (3H, s), 4.34 (2H, q), 4.56–4.62 (1H, m), 6.14 (1H, s), 6.48 (2H, brs), 6.77 (1H, t), 6.78 (1H, s). LCMS: m/z 493 (M$^+$+1).

(19d) In the same manner as in Example 3 (3c), the title compound (135 mg, 83%) was prepared as light yellow powder from ethyl 5-(2-amino-4,5-dimethoxybenzoyl)-2-(1-(3-pentyloxycarbonyloxy)propyl)-2H-1,2,3-triazole-4-carboxylate (180 mg) prepared in step (19c).

$^1$H-NMR (CDCl$_3$): δ 0.84 (3H, t), 0.92 (3H, t), 0.98 (3H, t), 1.55–1.67 (4H, m), 2.39–2.50 (2H, m), 4.00 (3H, s), 4.05 (3H, s), 4.60 (1H, quintet), 6.75 (1H, s), 6.92 (1H, t), 7.88 (1H, s), 9.54 (1H, s). LCMS: m/z 447 (M$^+$).

Example 20

2-(1-Isopropoxycarbonyloxy-2-methylpropyl)-7,8-dimethoxy-4(5H), 10-dioxo-2H-1,2,3-triazolo[4,5-c][1]benzazepine (20a) Ethyl 5-(4,5-dimethoxy-2-nitrobenzoyl)-1H-1,2,3-triazole-4-carboxylate (Synthesis Example 2) (1.07 g) and p-toluenesulfonic acid monohydrate (53 mg) were suspended in methylene chloride (10 ml) under an argon atmosphere. Isobutyl aldehyde (330 mg) was added to the suspension. The mixture was stirred at room temperature for 25 min. 1,1'-carbonyldiimidazole (744 mg) and methylene chloride (5.0 ml) were added thereto, and the mixture was stirred at room temperature for 25 min. Isopropyl alcohol (920 mg) was added thereto, and the mixture was stirred at room temperature for 3 hr and then refluxed for 21 hr. The mixture was post-treated by a conventional method and subjected to separation and purification to give ethyl 2-(1-isopropoxycarbonyloxy-2-methylpropyl)-5 (4,5-dimethoxy-2-nitrobenzoyl)-2H-1,2,3-triazole-4-carboxylate as a light yellow foam (520 mg, 34%).

$^1$H-NMR (CDCl$_3$): δ 0.72 (3H, d), 1.05 (3H, d), 1.25 (3H, d), 1.28 (3H, d), 1.44 (3H, t), 2.56 (1H, m), 4.00 (3H, s), 4.08 (3H, s), 4.49 (2H, q), 4.85 (1H, m), 6.35 (1H, d), 7.06 (1H, s), 7.62 (1H, s).

(20a) Ethyl 5-(4,5-dimethoxy-2-nitrobenzoyl)-1H-1,2,3-triazole-4-carboxylate (Synthesis Example 2) (50 g) was suspended in ethyl acetate (500 ml). Isobutyl aldehyde (20 ml) was added to the suspension at 25° C. under a nitrogen stream. The mixture was stirred at that temperature for 20 min.

Next, sodium iodide (21.4 g) and potassium carbonate (78.9 g) were added thereto. Further, 50 ml of isopropyl chloroformate was added thereto, and a reaction was allowed to proceed with stirring at 60° C. for 45 hr.

Ethyl acetate (100 ml) was added to the reaction solution. The mixture was washed twice with 750 ml of water and then washed with a 20% aqueous sodium chloride solution (500 ml). The organic layer was dried over anhydrous magnesium sulfate and concentrated under reduced pressure.

The residue was crystallized from aqueous methanol to give ethyl 2-(1-isopropoxycarbonyloxy-2-methylpropyl)-5-(4,5-dimethoxy-2-nitrobenzoyl)-2H-1,2,3-triazole-4-carboxylate (70.2 g, 96.7%). The $^1$H-NMR spectrum of this compound was the same as that of the compound prepared in step (20a).

(20a") Ethyl 5-(4,5-dimethoxy-2-nitrobenzoyl)-1H-1,2,3-triazole-4-carboxylate (Synthesis Example 2) (5.00 g) was suspended in ethyl acetate (50 ml). 1-Chloro-2-methylpropylisopropyl carbonate (8.34 g), sodium iodide (2.14 g), and potassium carbonate (7.89 g) were added to the suspension at 25° C. under a nitrogen stream. A reaction was allowed to proceed with stirring at 60° C. for 96 hr.

Ethyl acetate (10 ml) was added to the reaction solution. The mixture was washed twice with water (75 ml) and then washed with a 20% aqueous sodium chloride solution (50 ml). The organic layer was dried over anhydrous magnesium sulfate and concentrated under reduced pressure.

The residue was purified by column chromatography on silica gel (n-hexane/ethyl acetate) to give ethyl 2-(1-isopropoxycarbonyloxy-2-methylpropyl)-5(4,5-dimethoxy-2-nitrobenzoyl)-2H-1,2,3-triazole-4-carboxylate (0.89 g, 12.3%). The $^1$H-NMR spectrum of this compound was the same as that of the compound prepared in step (20a).

(20b) In the same manner as in Example 3 (3b), ethyl 5-(2-amino-4,5-dimethoxybenzoyl)-2-(1-isopropoxycarbonyloxy-2-methylpropyl)-2H-1,2,3-triazole-4-carboxylate (485 mg, 99%) was prepared as a light yellow foam from ethyl 2-(1-isopropoxycarbonyloxy-2-methylpropyl)-5(4,5-dimethoxy-2-nitrobenzoyl)-2H-1,2,3-triazole-4-carboxylate (520 mg) prepared in step (20a).

$^1$H-NMR (CDCl$_3$): δ 0.85 (3H, d), 1.14 (3H, d), 1.26 (3H, d), 1.28 (3H, t), 1.31 (3H, d), 2.75 (1H, m), 3.81 (3H, s), 3.90 (3H, s), 4.34 (2H, q), 4.86 (1H, m), 6.14 (1H, s), 6.49 (2H, brs), 6.51 (1H, d), 6.77 (1H, s).

(20c) In the same manner as in Example 3 (3c), the title compound (273 mg, 62%.) was prepared as a light yellow powder from ethyl 5-(2-amino-4,5-dimethoxybenzoyl)-2-(1-isopropoxycarbonyloxy-2-methylpropyl)-2H-1,2,3-triazole-4-carboxylate (485 mg) prepared in step (20b).

$^1$H-NMR (CDCl$_3$): δ 0.85 (3H, d), 1.15 (3H, d), 1.25 (3H, d), 1.31 (3H, d), 2.80 (1H, m), 4.00 (3H, s), 4.05 (3H, s), 4.86 (1H, m), 6.68 (1H, d), 6.73 (1H, s), 7.88 (1H, s), 9.47 (1H, brs) LCMS: m/z 433 (M$^+$+1).

Example 21

2-(Acetoxymethyl)-7,8-dimethoxy-4 (5H), 10-dioxo-2H-1,2,3-triazolo[4,5-c][1]benzazepine (21a) In the same manner as in Example 19 (a), provided that paraformaldehyde (45 mg) and acetic anhydride (0.3 ml) were used respectively instead of propionaldehyde and 1,1'-carbonyldiimidazole, ethyl 2-(acetoxymethyl)-5-(4,5-dimethoxy-2-nitrobenzoyl)-2H-1,2,3-triazole-4-carboxylate (618 mg, 98%) was prepared as a light yellow foam from ethyl 5-(4,5-dimethoxy-2-nitrobenzoyl)-1H-1,2,3-triazole-4-carboxylate (Synthesis Example 2) (525 mg).

$^1$H-NMR (CDCl$_3$): δ 1.45 (3H, t), 2.12 (3H, s), 4.01 (3H, s), 4.03 (3H, s), 4.50 (2H, q), 6.19 (2H, s), 7.04 (1H, s), 7.65 (1H, s). EIMS: m/z 422 (M$^+$).

(21b) In the same manner as in Example 3 (3b), ethyl 2-(acetoxymethyl)-5-(2-amino-4,5-dimethoxybenzoyl)-2H-1,2,3-triazole-4-carboxylate (510 mg, 90%) was prepared as a yellow oil from ethyl 2-(acetoxymethyl)-5-(4,5-dimethoxy-2-nitrobenzoyl)-2H-1,2,3-triazole-4-carboxylate (610 mg) prepared in step (21a).

$^1$H-NMR (CDCl$_3$): δ 1.27 (3H, t), 2.15 (3H, s), 3.66 (3H, s), 3.91 (3H, s), 4.34 (2H, q), 6.15 (1H, s), 6.35 (2H, s), 6.50 (2H, brs), 6.75 (1H, s). EIMS: m/z 392 (M$^+$).

(21c) In the same manner as in Example 3 (3c), the title compound (360 mg, 84%) was prepared as yellow powder from ethyl 2-(acetoxymethyl),-5-(2-amino-4,5-dimethoxybenzoyl)-2H-1,2,3-triazole-4-carboxylate (492 mg) prepared in step (21b).

$^1$H-NMR (DMSO-d$_6$): δ 2.12 (3H, s), 3.83 (3H, s), 3.84 (3H, s), 6.52 (2H, s), 7.14 (1H, s), 7.63 (1H, s), 11.2 (1H, brs). EIMS: m/z 346 (M$^+$)

Example 22

2-(Isobutyryloxymethyl)-7,8-dimethoxy-4 (5H), 10-dioxo-2H-1,2,3-triazolo[4,5-c][1]benzazepine (22a) In the same manner as in Example 19 (19a), provided that paraformaldehyde (12 mg) and isobutyric anhydride (0.17 ml) were used respectively instead of propionaldehyde and 1,1'-carbonyldiimidazole, ethyl 2-(isobutyryloxymethyl)-5-(4,5-dimethoxy-2-nitrobenzoyl)-2H-1,2,3-triazole-4-carboxylate (178 mg, 99%) was prepared as a light yellow oil from ethyl 5-(4,5-dimethoxy-2-nitrobenzoyl)-1H-1,2,3-triazole-4-carboxylate (Synthesis Example 2) (140 mg).

$^1$H-NMR (CDCl$_3$): δ 1.15 (3H, d), 1.21 (3H, d), 1.45 (3H, t), 2.57–2.68 (1H, m), 4.01 (3H, s), 4.03 (3H, s), 4.50 (2H, q), 6.20 (2H, s), 7.03 (1H, s), 7.65 (1H, s).

(22b) In the same manner as in Example 3 (3b), ethyl 5-(2-amino-4,5-dimethoxybenzoyl)-2-(isobutyryloxymethyl)-2H-1,2,3-triazole-4-carboxylate (510 mg, 90%) was prepared as a yellow oil from ethyl 2-(isobutyryloxymethyl)-5-(4,5-dimethoxy-2-nitrobenzoyl)- 2H-1,2,3-triazole-4-carboxylate (610 mg) prepared in step (22a)

$^1$H-NMR (CDCl$_3$) : δ 1.18 (6H, d), 1.28 (3H, t), 2.61–2.66 (1H, m), 3.65 (3H, s), 3.90 (3H, s), 4.34 (2H, q), 6.15 (1H, s), 6.36 (2H, s), 6.50 (2H, brs), 6.75 (1H, s). EIMS: m/z 420 (M$^+$).

(22c) In the same manner as in Example 3 (3c), the title compound (360 mg, 84%) was prepared as yellow powder from ethyl 5-(2-amino-4,5-dimethoxybenzoyl)-2-(isobutyryloxymethyl)-2H-1,2,3-triazole-4-carboxylate (492 mg) prepared in step (22b).

$^1$H-NMR (DMSO-d$_6$): δ 1.10 (6H, d), 2.62–2.69 (1H, m), 3.84 (3H, s) 3.85 (3H, s), 6.54 (2H, s), 7.18 (1H, s), 7.64 (1H, s), 11.16 (1H, brs). EIMS: m/z 374 (M$^+$).

Example 23

2-(n-Butyryloxymethyl)-7,8-dimethoxy-4 (5H), 10-dioxo-2H-1,2,3-triazolo[4,5-c][1]benzazepine (23a) In the same manner as in Example 19 (19a), provided that paraformaldehyde (12 mg) and butyric anhydride (0.13 ml) were used respectively instead of propionaldehyde and 1,1'-carbonyldiimidazole, ethyl 2-(n-butyryloxymethyl)-5-(4,5-dimethoxy-2-nitrobenzoyl)-2H-1,2,3-triazole-4-carboxylate (178 mg, 99%) was prepared as a light yellow foam from ethyl 5-(4,5-dimethoxy-2-nitrobenzoyl)-1H-1,2,3-triazole-4-carboxylate (Synthesis Example 2) (140 mg).

$^1$H-NMR (CDCl$_3$): δ 0.92 (3H, t), 1.44 (3H, t), 1.61–1.71 (2H, m), 2.44 (2H, t), 4.01 (3H, s), 4.03 (3H, s), 4.50 (2H, q), 6.20 (2H, s), 7.03 (1H, s), 7.65 (1H, s). EIMS: m/z 450 (M$^+$).

(23b) In the same manner as in Example 3 (3b), ethyl 5-(2-amino-4,5-dimethoxybenzoyl)-2-(n-butyryloxymethyl)-2H-1,2,3-triazole-4-carboxylate (126 mg, 83%) was prepared as a yellow oil from ethyl 2-(n-butyryloxymethyl)-5-(4,5-dimethoxy-2-nitrobenzoyl)-2H-1,2,3-triazole-4-carboxylate (160 mg) prepared in step (23a).

$^1$H-NMR (CDCl$_3$): δ 0.95 (3H, t), 1.27 (3H, t), 1.64–1.70 (2H, m), 2.37 (2H, t), 3.65 (3H, s), 3.91 (3H, s), 4.34 (2H, q), 6.15 (1H, s), 6.36 (2H, s), 6.50 (2H, brs), 6.75 (1H, s). EIMS: m/z 420 (M$^+$).

(23c) In the same manner as in Example 3 (3c), the title compound (86 mg, 80%) was prepared as yellow powder from ethyl 5-(2-amino-4,5-dimethoxybenzoyl)-2-(n-butyryloxymethyl)-2H-1,2,3-triazole-4-carboxylate (120 mg) prepared in step (23b).

$^1$H-NMR (DMSO-d$_6$): δ 0.87 (3H, t), 1.51–1.60 (2H, m), 2.43 (2H, t), 3.84 (3H, s), 3.85 (3H, s), 6.54 (2H, s), 7.17 (1H, s), 7.64 (1H, s), 11.2 (1H, brs). EIMS: m/z 374 (M$^+$).

Example 24

2-(3-Carboxyropionyloxymethyl)-7,8-dimethoxy-4 (5H), 10-dioxo-2H-1,2,3-triazolo[4,5-c][1]benzazepine (24a) In the same manner as in Example 19 (19a), provided that paraformaldehyde (15 mg) and a methylene chloride solution of an acid chloride prepared from a monobenzyl ester of succinic acid (520 mg) and thionyl chloride (0.91 ml) were used respectively instead of propionaldehyde and 1,1'-carbonyldiimidazole, ethyl 2-(3-(benzyloxycarbonyl)propionyloxymethyl)-5-(4,5-dimethoxy-2-nitrobenzoyl)-2H-1,2,3-triazole-4-carboxylate (148 mg, 58%) was prepared from ethyl 5-(4,5-dimethoxy-2-nitrobenzoyl)-1H-1,2,3-triazole-4-carboxylate (Synthesis Example 2) (175 mg).

$^1$H-NMR (CDCl$_3$): δ 1.44 (3H, t), 2.69 (4H, s), 3.99 (3H, s), 4.02 (3H, s), 4.49 (2H, q), 5.11 (2H, s), 6.19 (2H, s), 7.03 (1H, s), 7.30–7.40 (5H, m), 7.63 (1H, s).

(24b) In the same manner as in Example 3 (3b) and (3c), the title compound (7 mg, 26%) was prepared from ethyl 2-(3-(benzyloxycarbonyl)propionyloxymethyl)-5-(4,5-dimethoxy-2-nitrobenzoyl)-2H-1,2,3-triazole-4-carboxylate (100 mg) prepared in step (24a).

$^1$H-NMR (DMSO-d$_6$): δ 2.60 (4H, m), 3.83 (3H, s), 3.85 (3H, s), 6.54 (2H, s), 7.17 (1H, s), 7.64 (1H, s), 11.16 (1H, s), 12.54 (1H, brs). FABMS: m/z 405 (M$^+$+1).

Example 25

2-(Cyclohexylcarbonyloxymethyl)-7,8-dimethoxy-4 (5H), 10-dioxo-2H-1,2,3-triazolo[4,5-c][1]benzazepine (25a) In the same manner as in Example 19 (19a), provided that paraformaldehyde (15 mg) and cyclohexylcarbonyl chloride (0.54 ml) were used respectively instead of propionaldehyde and 1,1'-carbonyldiimidazole, ethyl 2-(cyclohexylcarbonyloxymethyl)-5-(4,5-dimethoxy-2-nitrobenzoyl)-2H-1,2,3-triazole-4-carboxylate (416 mg) was prepared from ethyl 5-(4,5-dimethoxy-2-nitrobenzoyl)-1H-1,2,3-triazole-4-carboxylate (Synthesis Example 2) (175 mg).

$^1$H-NMR (CDCl$_3$): δ 1.20–2.00 (10H, m), 1.44 (3H, t), 2.35 (1H, m), 4.00 (3H, s), 4.03 (3H, s), 4.49 (2H, q), 6.19 (2H, s), 7.03 (1H, s), 7.65 (1H, s). FABMS: m/z 491 (M$^+$+1).

(25b) In the same manner as in Example 3 (3b) and (3c), the title compound (32 mg, 18%) was prepared from ethyl 2-(cyclohexylcarbonyloxymethyl)-5-(4,5-dimethoxy-2-nitrobenzoyl)-2H-1,2,3-triazole-4-carboxylate (a) (200 mg) prepared in step (25a).

$^1$H-NMR (DMSO-d$_6$): δ 1.16–1.90 (10H, m), 2.45 (1H, m), 3.83 (3H, s), 3.85 (3H, s), 6.51 (2H, s), 7.16 (1H, s), 7.64 (1H, s), 11.15 (1H, s). FABMS: m/z 415 (M$^+$+1).

Example 26

7,8-Dimethoxy-2-(3-methoxypentan-3-yl)-4 (5H), 10-dioxo-2H-1,2,3-triazolo[4,5-c][1]benzazepine (26a) p-Toluenesulfonic acid monohydrate (20 mg) was added to a solution of 3-pentanone (3.1 ml) and trimethyl orthoformate (3.3 ml) in methylene chloride (10 ml). The mixture was heated for one hr with stirring. This solution (4 ml) was added to a solution of ethyl 5-(4,5-dimethoxy-2-nitrobenzoyl)-1H-1,2,3-triazole-4-carboxylate (Synthesis Example 2) (140 mg) in methylene chloride (2 ml). The mixture was stirred at room temperature for one hr, and triethylamine (0.05 ml) was then added thereto. The mixture was post-treated by a conventional method and subjected to separation and purification to give ethyl 5-(4,5-dimethoxy-2-nitrobenzoyl)-2-(3-methoxypentan-3-yl)-2H-1,2,3-triazole-4-carboxylate (140 mg, 78%) as a yellow powder.

$^1$H-NMR (CDCl$_3$): δ 0.75–0.79 (6H, m), 1.45 (3H, t), 2.19–2.25 (4H, m), 2.97 (3H, s), 4.01 (3H, s), 4.04 (3H, s), 4.49 (2H, q), 7.10 (1H, s), 7.60 (1H, s). FABMS: m/z 451 (M$^+$+1).

(26b) In the same manner as in Example 3 (3b), ethyl 5-(2-amino-4,5-dimethoxybenzoyl)-2-(3-methoxypentan-3-yl)-2H-1,2,3-triazole-4-carboxylate (110 mg, 91° o) from ethyl 5-(4,5-dimethoxy-2-nitrobenzoyl)-2-(3-methoxypentan-3-yl)-2H-1,2,3-triazole-4-carboxylate (130 mg) prepared in step (26a).

$^1$H-NMR (CDCl$_3$): δ 0.87 (6H, t), 1.26 (3H, t), 2.33–2.45 (4H, m), 3.13 (3H, s), 3.61 (31, s), 3.90 (3H, s), 4.33 (2H, q), 6.15 (1H, s), 6.49 (2H, brs), 6.74 (1H, s). FABMS: m/z 421 (M$^+$+1).

(26c) Ethyl 5-(2-amino-4,5-dimethoxybenzoyl)-2-(3-methoxypentan-3-yl)-2H-1,2,3-triazole-4-carboxylate (80 mg) was dissolved in isopropyl alcohol (1.5 ml) under an argon atmosphere. Potassium tert-butoxide (25 mg) was added to the solution. The mixture was stirred at room temperature for 15 min. The mixture was post-treated by a conventional method and subjected to separation and purification to give the title compound (35 mg, 49%) as a yellow powder.

$^1$H-NMR (CDCl$_3$): δ 0.87 (6H, t), 2.42 (2H, q), 2.53 (2H, q), 3.13 (3H, s), 4.00 (3H, s), 4.03 (3H, s), 6.66 (1H, s), 7.90 (1H, s), 9.14 (1H, brs). FABMS: m/z 374 (M$^+$).

Example 27

2-(4-Ethoxyheptan-4-yl)-7,8-dimethoxy-4 (5H), 10-dioxo-2H-1,2,3-triazolo[4,5-c][1]benzazepine (27a) Ethyl 5-(4,5-dimethoxy-2-nitrobenzoyl)-1H-1,2,3-triazole-4-carboxylate (Synthesis Example 2) (140 mg) and p-toluenesulfonic acid monohydrate (2 mg) were suspended in methylene chloride (2 ml) under an argon atmosphere. 4-Heptane (0.14 ml) and triethyl orthoformate (0.17 ml) were added to the suspension. The mixture was stirred at room temperature for 2 hr. Further, p-toluenesulfonic acid monohydrate (4.5 mg) was added thereto. The mixture was stirred at room temperature for 2 hr. The mixture was post-treated by a conventional method and subjected to separation and purification to give ethyl 2-(4-ethoxyheptan-4-yl)-5-(4,5-dimethoxy- 2-nitrobenzoyl)-2H-1,2,3-triazole-4-carboxylate (160 mg, 82%) as a yellow powder.

$^1$H-NMR (CDCl$_3$): δ 0.90 (6H, t), 1.00–1.15 (2H, m), 1.04 (3H, t), 1.26–1.28 (2H, m), 1.44 (3H, t), 2.05–2.21 (4H, m), 3.10 (2H, q), 4.01 (3H, s), 4.04 (3H, s), 4.48 (2H, q), 7.08 (1H, s), 7.61 (1H, s). EIMS: m/z 492 (M$^+$).

(27b) In the same manner as in Example 3 (3b), ethyl 5-(2-amino-4,5-dimethoxybenzoyl)-2-(4-ethoxyheptan-4-yl)-2H-1,2,3-triazole-4-carboxylate (160 mg, 90%) was prepared as a yellow oil from ethyl 2-(4-ethoxyheptan-4-yl)-5-(4,5-dimethoxy-2-nitrobenzoyl)-2H-1,2,3-triazole-4-carboxylate (190 mg) prepared in step (27a).

$^1$H-NMR (CDCl$_3$): δ 0.95 (6H, t), 1.10–1.19 (2H, m), 1.11 (3H, t), 1.25 (3H, t), 1.35–1.38 (2H, m), 2.24–2.42 (4H, m), 3.25 (2H, q), 3.61 (3H, s), 3.90 (3H, s), 4.32 (2H, q), 6.15 (1H, s), 6.50 (2H, brs), 6.74 (1H, s). EIMS: m/z 462 (M$^+$).

(27c) In the same manner as in Example 26 (26c), the title compound (75 mg, 60%) was prepared as a yellow crystal powder from ethyl 5-(2-amino-4,5-dimethoxybenzoyl)-2-(4-ethoxyheptan-4-yl)-2H-1,2,3-triazole-4-carboxylate (143 mg) prepared in step (27b).

$^1$H-NMR (CDCl$_3$): δ 0.96 (6H, t), 1.11–1.19 (2H, m), 1.13 (3H, t), 1.34–1.43 (2H, m), 2.30–2.38 (2H, m), 2.44–2.52 (2H, m), 3.28 (2H, q), 4.00 (3H, s), 4.05 (3H, s), 6.80 (1H, s), 7.90 (1H, s), 9.68 (1H, brs). FABMS: m/z 417 (M$^+$+1).

Example 28

2-(Ethoxymethyl)-7,8-dimethoxy-4(5H), 10-dioxo-2H-1,2,3-triazolo[4,5-c][1]benzazepine (28a) Ethyl 5-(4,5-dimethoxy-2-nitrobenzoyl)- 1H-1,2,3-triazole-4-carboxylate (Synthesis Example 2) (210 mg) and p-toluenesulfonic acid mohohydrate (62 mg) were suspended in methylene chloride (5 ml) under an argon atmosphere. Diethoxymethane (0.5 ml) was added to the suspension. The mixture was stirred at 80° C. for 2 hr. The mixture was post-treated by a conventional method and subjected to separation and purification to give ethyl 2-(ethoxymethyl)-5-(4,5-dimethoxy-2-nitrobenzoyl)-2H-1,2,3-triazole-4-carboxylate (242 mg, 99%) as a yellow powder.

$^1$H-NMR (CDCl$_3$): δ 1.17 (3H, t), 1.45 (3H, t), 3.55 (2H, q), 4.00 (3H, s), 4.03 (3H, s), 4.49 (2H, q), 5.62 (2H, s), 7.05 (1H, s), 7.64 (1H, s). EIMS: m/z 408 (M$^+$).

(28b) In the same manner as in Example 3 (3b), ethyl 5-(2-amino-4,5-dimethoxybenzoyl)-2-(ethoxymethyl)-2H-1,2,3-triazole-4-carboxylate (178 mg, 88%) was prepared as a yellow oil from ethyl 2-(ethoxymethyl)-5-(4,5-dimethoxy-2-nitrobenzoyl)-2H-1,2,3-triazole-4-carboxylate (220 mg) prepared in step (28a).

$^1$H-NMR (CDCl$_3$): δ 1.21 (3H, t), 1.26 (3H, t), 3.63 (3H, s), 3.70 (2H, q), 3.90 (3H, s), 4.43 (2H, g), 5.78 (2H, s), 6.15 (1H, s), 6.50 (2H, brs), 6.73 (1H, s). EIMS: m/z 378 (M$^+$).

(28c) In the same manner as in Example 26 (26c), the title compound (116 mg, 92%) was prepared as a yellow powder from ethyl 5-(2-amino-4,5-dimethoxybenzoyl)-2-(ethoxymethyl)-2H-1,2,3-triazole-4-carboxylate (142 mg) prepared in step (28b).

$^1$H-NMR (DMSO-d$_6$): δ 1.12 (3H, t), 3.64 (2H, q), 3.83 (3H, s), 3.85 (3H, s), 5.94 (2H, s), 7.13 (1H, s), 7.65 (1H, s), 11.2 (1H, brs). EIMS: m/z 332 (M$^+$).

Example 29

2-(Isopropoxymethyl)-7,8-dimethoxy-4 (5H), 10-dioxo-2H-1,2,3-triazolo[4,5-c][1]benzazepine (29a) In the same manner as in Example 19 (19a), paraformaldehyde (42 mg), and isopropyl alcohol (0.092 ml) were used respectively instead of propionaldehyde and 1,1'-carbonyldiimidazole. Thus, ethyl 2-(isopropoxymethyl)-5-(4,5-dimethoxy-2-nitrobenzoyl)-2H-1,2,3-triazole-4-carboxylate (215 mg, 85%) was prepared as a light yellow oil from ethyl 5-(4,5-dimethoxy-2-nitrobenzoyl)-1H-1,2,3-triazole-4-carboxylate (Synthesis Example 2) (210 mg).

$^1$H-NMR (CDCl$_3$): δ 1.17 (6H, d), 1.45 (3H, t), 3.74–3.80 (1H, m), 4.00 (3H, s), 4.03 (3H, s), 4.49 (2H, q), 5.63 (2H, s), 7.04 (1H, s), 7.64 (1H, s). EIMS: m/z 422 (M$^+$).

(29b) In the same manner as in Example 3 (3b), ethyl 5-(2-amino-4,5-dimethoxybenzoyl)-2-(isopropoxymethyl)-2H-1,2,3-triazole-4-carboxylate (190 mg) was prepared as a yellow oil from ethyl 2-(isopropoxymethyl)-5-(4,5-dimethoxy-2-nitrobenzoyl)-2H-1,2,3-triazole-4-carboxylate (200 mg) prepared in step (29a).

$^1$H-NMR (CDCl$_3$): δ 1.17 (6H, d), 1.26 (3H, t), 3.63 (3H, s), 3.80–3.90 (1H, m), 3.90 (3H, s),4.43 (2H, q), 5.80 (2H, s), 6.16 (1H, s), 6.50 (2H, brs), 6.72 (1H, s). EIMS: m/z 392 (M$^+$).

(29c) In the same manner as in Example 26 (26c), the title compound (110 mg, 70%) was prepared as a yellow powder from ethyl 5-(2-amino-4,5-dimethoxybenzoyl)-2-(isopropoxymethyl)-2H-1,2,3-triazole-4-carboxylate (180 mg) prepared in step (26b).

$^1$H-NMR (DMSO-d$_6$): δ 1.12 (6H, d), 3.84 (3H, s), 3.85 (3H, s), 3.93–3.95 (1H, m), 5.96 (2H, s), 7.18 (1H, s), 7.66 (1H, s), 11.1 (1H, brs) EIMS: m/z 346 (M$^+$).

Example 30

2-(1-(1,3-Diethoxy-2-propoxycarbonyloxy)-2-methylpropyl)-7,8-dimethoxy-4(5H), 10-dioxo-2H-1,2,3-triazolo[4,5-c][1]benzazepine (30a) In the same manner as in Example 19 (19a), provided that isobutyl aldehyde (0.078 ml) was used instead of propionaldehyde, ethyl 2-(1-(1-imidazolylcarbonyloxy)-2-methylpropyl)-5-(4,5-dimethoxy-2-nitrobenzoyl)-2H-1,2, 3-triazole-4-carboxylate (252 mg, 61%) was prepared from ethyl 5-(4,5-dimethoxy-2-nitrobenzoyl)-1H-1,2,3-triazole-4-carboxylate (Synthesis Example 2) (280 mg).

$^1$H-NMR (CDCl$_3$): δ 0.82 (3H, d), 1.12 (3H, d), 1.44 (3H, t), 2.64–2.81 (1H, m), 4.01 (3H, s), 4.04 (3H, s), 4.50 (2H, q), 6.67 (1H, d), 7.08 (2H, m), 7.41 (1H, s), 7.59 (1H, s), 8.14 (1H, m). LCMS:m/z 517 (M$^+$+1).

(30b) In the same manner as in Example 19 (19b), provided that 1,3-diethoxy-2-propanol (0.6 ml) was used instead of 3-pentanol, ethyl 2-(1-(1,3-diethoxy-2-propoxycarbonyloxy)-2-methylpropyl)-5-(4,5-dimethoxy-2-nitrobenzoyl)-2H-1,2,3-triazole-4-carboxylate (165 mg, 44%) was prepared as a light yellow oil from ethyl 2-(1-(1-imidazolylcarbonyloxy)-2-methylpropyl)-5-(4,5-dimethoxy-2-nitrobenzoyl)-2H-1,2,3-triazole-4-carboxylate (325 mg) prepared in step (30a).

$^1$H-NMR (CDCl$_3$): δ 0.71 (3H, d), 1.08–1.25 (9H, m), 1.45 (3H, t), 2.49–2.61 (1H, m), 3.38–3.63 (8H, m), 4.01 (3H, s), 4.04 (3H, s), 4.50 (2H, q), 4.92–4.94 (1H, m), 6.38 (1H, d), 7.06 (1H, s), 7.62 (1H, s). LCMS: m/z 597 (M$^+$+1).

(30c) In the same manner as in Example 3 (3b), ethyl 5-(2-amino-4,5-dimethoxybenzoyl)-2-(1-(1, 3-diethoxy-2-propoxycarbonyloxy)-2-methylpropyl)-2H-1,2,3-triazole-4-carboxylate (177 mg, 78%) was prepared as a light yellow oil from ethyl 2-(1-(1,3-diethoxy-2-propoxycarbonyloxy)-2-methylpropyl)-5-(4,5-dimethoxy-2-nitrobenzoyl)-2H-1,2, 3-triazole-4-carboxylate (240 mg) prepared in step (30b).

$^1$H-NMR (CDCl$_3$): δ 0.85 (3H, d), 1.08–1.21 (9H, m), 1.29 (3H, t), 2.75–2.81 (1H, m), 3.40–3.72 (11H, m), 3.91 (3H, s), 4.34 (2H, q), 4.92–4.97 (1H, m), 6.15 (1H, s), 6.50 (2H, brs), 6.54 (1H, d), 6.79 (1H, s). LCMS: m/z 567 (M$^+$+1).

(30d) In the same manner as in Example 3 (3c), the title compound (65 mg, 40%) was prepared as light yellow crystal powder from ethyl 5-(2-amino-4,5-dimethoxybenzoyl)-2-(1-(1,3-diethoxy-2-propoxycarbonyloxy)-2-methylpropyl)-2H-1,2,3-triazole-4-carboxylate (175 mg) prepared in step (30c).

$^1$H-NMR (CDCl$_3$): δ 0.85 (3H, t), 1.09 (3H, t), 1.16–1.19 (6H, m), 2.75–2.85 (1H, m), 3.38–3.66 (8H, m), 4.00 (3H, s), 4.04 (3H, s), 4.88–4.93 (1H, m), 6.68 (1H, s), 6.70 (1H, d), 7.88 (1H, s), 9.31 (1H, s). FABMS: m/z 521 (M$^+$+1).

Example 31

7,8-Dimethoxy-2-(1-(2-(2-methoxyethoxy) ethoxycarbonyloxy)-2-methylpropyl)-4(5H), 10-dioxo-2H-1,2,3-triazolo[4,5-c][1]benzazepine (31a) In the same manner as in Example 19 (19b), provided that diethylene glycol monomethyl ether (3.6 ml) was used instead of 3-pentanol and trifluoroacetic acid (3.8 ml) was added, ethyl 2-(1-(2-( 2-methoxyethoxy) ethoxycarbonyloxy)-2-methylpropyl)-5-(4,5-dimethoxy-2-nitrobenzoyl)-2H-1,2,3-triazole-4-carboxylate (8.82 g, 52%) was prepared from ethyl 2-(1-(1-imidazolylcarbonyloxy)-2-methylpropyl)-5-(4,5-dimethoxy-2-nitrobenzoyl)-2H-1,2,3-triazole-4-carboxylate (13.0 g) prepared in step (30a).

$^1$H-NMR (CDCl$_3$): δ 0.72 (3H, d), 1.07 (3H, d), 1.44 (3H, t), 2.50–2.65 (1H, m), 3.36 (3H, s), 3.50–3.55 (2H, m), 3.60–3.65 (2H, m), 3.65–3.75 (2H, m), 4.01 (3H, s), 4.04 (3H, s), 4.20–4.35 (2H, m), 4.49 (2H, q), 6.35 (1H, d), 7.07 (1H, s), 7.62 (1H, s).

(31b) In the same manner as in Example 3 (3b), ethyl 5-(2-amino-4,5-dimethoxy)-2-(1-(2-(2-methoxyethoxy) ethoxycarbonyloxy)-2-methylpropyl)-2H-1,2,3-triazole-4-carboxylate (1.14 g, 100%) was prepared from ethyl 2-(1-(2-(2-methoxyethoxy) ethoxycarbonyloxy)-2-methylpropyl)-5-(4,5-dimethoxy-2-nitrobenzoyl)-2H-1,2,3-triazole-4-carboxylate (1.15 g) prepared in step (31a).

$^1$H-NMR (CDCl$_3$): δ 0.85 (3H, d), 1.15 (3H, d), 1.29 (3H, t), 2.70–2.85 (1H, m), 3.36 (3H, s), 3.50–3.55 (2H, m), 3.60–3.65 (2H, m), 3.64 (3H, s), 3.69–3.75 (2H, m), 3.90 (3H, s), 4.35 (2H, q), 4.20–4.40 (2H, m), 6.14 (1H, s), 6.49 (2H, s), 6.53 (1H, d), 6.78 (1H, s).

(31c) In the same manner as in Example 3 (3c), the title compound (750 mg, 75%) was prepared as a light yellow crystal powder from ethyl 5-(2-amino-4,5-dimethoxy)-2-(1-(2-(2-methoxyethoxy)ethoxycarbonyloxy)-2-methylpropyl)-2H-1,2,3-triazole-4-carboxylate (1.11 mg) prepared in step (31b).

$^1$H-NMR (CDCl$_3$): δ 0.86 (3H, d), 1.17 (3H, d), 2.75–2.90 (1H, m), 3.35 (3H, s), 3.50–3.55 (2H, m), 3.60–3.65 (2H, m), 3.71 (2H, t), 4.00 (3H, s), 4.07 (3H, s), 4.26 (1H, dt), 4.34 (1H, dt), 6.68 (1H, d), 6.85 (1H, s), 7.88 (1H, s), 9.94 (1H, s).

Example 32

2-(1-(1,3-Diethoxy-2-propoxycarbonyloxy)-2-methylpropyl)-8-isopropoxy-7-methoxy-4(5H), 10-dioxo-2H-1,2,3-triazolo[4,5-c][1]benzazepine (32a) In the same manner as in Synthesis Example 2, ethyl 5-(5-isopropoxy-4-methoxy-2-nitrobenzoyl)-1H-1,2,3-triazole-4-carboxylate (1.47 g, 78%) was prepared from an about 1:1 mixture (2.49 g) of ethyl 4-(5-isopropoxy-4-methoxy-2-nitrobenzoyl)-1-(4-methoxybenzyl)-1H-1,2,3-triazole-5-carboxylate (Synthesis Example 3, b-1) and ethyl 5-(5-isopropoxy-4-methoxy-2-nitrobenzoyl)-1-(4-methoxybenzyl)-1H-1,2,3-triazole-4-carboxylate (Synthesis Example 3, b-2).

$^1$H-NMR (CDCl$_3$): δ 1.43 (9H, d), 4.00 (3H, s), 4.47 (2H, q), 4.65–4.80 (1H, m), 7.00 (1H, s), 7.66 (1H, s).

(32b) p-Toluenesulfonic acid monohydrate (57 mg) and isobutyl aldehyde (0.41 ml) were added to a solution of ethyl 5-(5-isopropoxy-4-methoxy-2-nitrobenzoyl)-1H-1,2,3-triazole-4-carboxylate (1.14 g), prepared in step (32a), in methylene chloride solution (17 ml) at −20° C. The mixture was stirred at that temperature for one hr. 1,1'-Carbonyldiimidazole (732 mg) was added to the reaction solution. Further, one hr after that, 1,3-diethoxy-2-propanol (4.70 ml) was added thereto. The reaction solution was cooled to −30° C. Trifluoroacetic acid (0.70 ml) was added thereto. The temperature was raised to room temperature, followed by stirring for 25 hr. 0.5 M hydrochloric acid was added to the reaction solution under ice cooling to stop the reaction, and separation was then carried out. The organic layer was washed five times with a 7% aqueous sodium hydrogencarbonate solution. The solvent was evaporated under reduced pressure. Diethyl ether and water were added to the residue. The organic layer after the separation was successively washed twice with water, with 0.5 M hydrochloric acid, twice with water, and then with 20% saline. The solvent was evaporated under reduced pressure. The residue was purified by column chromatography on silica gel (ethyl acetate/hexane) to give a crude product of ethyl 2-(1-(1,3-diethoxy-2-propoxycarbonyloxy)-2-methylpropyl)-5-(5-isopropoxy-4-methoxy-2-nitrobenzoyl)-2H-1,2,3-triazole-4-carboxylate (1.15 g).

$^1$H-NMR (CDCl$_3$): δ 0.71 (3H, d), 1.07 (3H, d), 1.10 (3H, t), 1.15 (3H, t), 1.41–1.47 (9H, m), 2.54–2.65 (1H, m), 3.40–3.64 (8H, m), 4.01 (3H, s), 4.49 (2H, q), 4.68–4.76 (1H, m), 4.90–4.96 (1H, m), 6.39 (1H, d), 7.03 (1H, s), 7.61 (1H, s). EIMS: m/z 624 (M$^+$).

(32b) In the same manner as in Example 3 (3b), ethyl 5-(2-amino-5-isopropoxy-4-methoxybenzoyl)-2-(1-(1,3-diethoxy-2-propoxycarbonyloxy)-2-methylpropyl)-2H-1,2,3-triazole-4-carboxylate (1.08 g, 100%) was prepared from ethyl 2-(1-(1,3-diethoxy-2-propoxycarbonyloxy)-2-methylpropyl)-5-(5-isopropoxy-4-methoxy-2-nitrobenzoyl)-2H-1,2,3-triazole-4-carboxylate (1.12 g) prepared in step (32a).

$^1$H-NMR (CDCl$_3$): δ 0.85 (3H, d), 1.13 (3H, t), 1.18 (3H, t), 1.23 (6H, 2d), 1.26 (3H, t), 1.49 (3H, d), 2.73–2.82 (1H, m), 3.40–3.68 (8H, m), 4.09–4.17 (1H, m), 4.33 (2H, q), 4.93–5.00 (1H, m), 6.13 (1H, s), 6.46 (2H, s), 6.56 (1H, d), 6.83 (1H, s). EIMS: m/z 594 (M$^+$).

(32c) In the same manner as in Example 3 (3c), the title compound (634 mg, 65% in two steps) was prepared from ethyl 5-(2-amino-5-isopropoxy-4-methoxybenzoyl)-2-(1-(1,3-diethoxy-2-propoxycarbonyloxy)-2-methylpropyl)-2H-1,2,3-triazole-4-carboxylate (1.08 g) prepared in step (32b).

$^1$H-NMR (CDCl$_3$): δ 0.85 (3H, d), 1.08 (3H, t), 1.17 (3H, d), 1.18 (3H, t), 1.42 (6H, d), 2.78–2.90 (1H, m), 3.36–3.66 (8H, m), 4.03 (3H, s), 4.68–4.79 (1H, m), 4.90–5.00 (1H, m)), 6.70 (1H, d), 6.79 (1H, s), 7.90 (1H, s), 9.74 (1H, s). EIMS: m/z 548 (M+).

Example 33

8-Isopropoxy-2-(1-isopropoxycarbonyloxy-2-methylpropyl)-7-methoxy-4 (5H), 10-dioxo-2H-1,2,3-triazolo[4,5-c][1]benzazepine (33a) Isobutyl aldehyde (2.9 ml), sodium iodide (3.18 g), potassium carbonate (11.69 g), and isopropyl chloroformate (7.2 ml) were added in that order under an argon atmosphere at room temperature to a solution of ethyl 5-(5-isopropoxy-4-methoxy-2-nitrobenzoyl)-1H-1,2,3-triazole-4-carboxylate (8.01 g), prepared in step (32a), in acetone (150 ml). The mixture was stirred at that temperature for 19.5 hr. Water was added to the reaction mixture to stop the reaction. The mixture was extracted with ethyl acetate. The organic layer was washed with 20% saline and dried over anhydrous magnesium sulfate. The solvent was evaporated. The resultant mixture was purified by column chromatography on silica gel (hexane/ethyl acetate) to give ethyl 2-(1-isopropoxycarbonyloxy-2-methylpropyl)-5-(5-isopropoxy-4-methoxy-2-nitrobenzoyl)-2H-1,2,3-triazole-4-carboxylate (10.12 g, 89%).

$^1$H-NMR (CDCl$_3$): δ 0.72 (3H, d), 1.05 (3H, d), 1.26 (3H, d), 1.28 (3H, d), 1.44 (3H, t), 2.57 (1H, m), 4.00 (3H, s), 4.49 (2H, q), 4.72 (1H, m), 4.85 (1H, sept.), 6.36 (1H, d), 7.01 (1H, s), 7.60 (1H, s). TSPMS: 537 (M+ +1).

(33b) In the same manner as in Example 3 (3b), ethyl 5-(2-amino-5-isopropoxy-4-methoxybenzoyl)-2-(1-isopropoxycarbonyloxy-2-methylpropyl)-2H-1,2,3-triazole-4-carboxylate was prepared from ethyl 2-(1-isopropoxycarbonyloxy-2-methylpropyl)-5-(5-isopropoxy-4-methoxy-2-nitrobenzoyl)-2H-1,2,3-triazole-4-carboxylate (10.12 g) prepared in step (33a).

$^1$H-NMR (CDCl$_3$): δ 0.85 (3H, d), 1.15 (3H, d), 1.22 (6H, d), 1.2–1.4 (9H, m), 2.76 (1H, d), 3.87 (3H, s), 4.10 (1H, m), 4.30 (2H, m), 4.88 (1H, sept.), 6.13 (1H, s), 6.53 (1H, d), 6.81 (1H, s). TSPMS: 507 (M+ +1).

(33c) A solution of ethyl 5-(2-amino-5-isopropoxy-4-methoxybenzoyl)-2-(1-isopropoxycarbonyloxy-2-methylpropyl)-2H-1,2,3-triazole-4-carboxylate, prepared in step (33b), in acetic acid (100 ml) was stirred at 90° C. for 3.5 hr under an argon atmosphere. The reaction mixture was concentrated. Toluene was added to the concentrate, and the solution was then again concentrated. The concentrate was extracted with methylene chloride, followed by washing twice with a 7% aqueous sodium hydrogencarbonate solution and once with 10% saline. The organic layer was concentrated. The solvent was evaporated. The resultant mixture was washed twice with isopropyl alcohol and purified by column chromatography (chloroform/ethyl acetate) to give the title compound (4.02 g, 45% in two steps).

$^1$H-NMR (CDCl$_3$): δ 0.85 (3H, s), 1.16 (3H, d), 1.26 (3H, d), 1.31 (3H, d), 1.42 (6H, d), 2.81 (1H, m), 4.03 (3H, s), 4.74 (1H, sept.), 4.86 (1H, sept.), 6.68 (1H, d), 6.76 (1H, s) 7.90 (1H, s), 9.64 (1H, brs) FABMS: 461 (M+ +1).

The title compounds of Examples 1 to 33 have the following respective chemical formulae.

TABLE 1

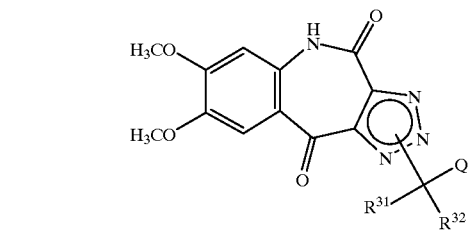

| Example | R$^{31}$ (or R$^{32}$) | R$^{32}$ (or R$^{31}$) | Q |
|---|---|---|---|
| 1 | H | CH$_3$ | OCO$_2$CH(CH$_3$)$_2$ |
| 2 | H | H | OCOC(CH$_3$)$_3$ |

TABLE 2

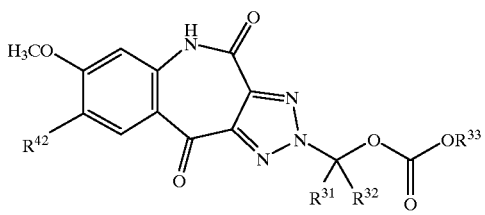

| Example | R$^{42}$ | R$^{31}$ (or R$^{32}$) | R$^{32}$ (or R$^{31}$) | R$^{33}$ |
|---|---|---|---|---|
| 3 | OCH$_3$ | H | H | CH$_2$CH$_3$ |
| 4 | OCH$_3$ | H | H | CH$_2$CH(CH$_3$)$_2$ |
| 5 | OCH$_3$ | H | H | (CH$_2$)$_5$CH$_3$ |
| 6 | OCH$_3$ | H | H | (CH$_2$)$_3$CH$_3$ |
| 7 | OCH$_3$ | H | H | CH(CH$_3$)$_2$ |
| 17a | OCH$_3$ | H | H | C$_6$H$_4$NO$_2$-p |
| 19 | OCH$_3$ | H | CH$_2$CH$_3$ | CH(CH$_2$CH$_3$)$_2$ |
| 20 | OCH$_3$ | H | CH(CH$_3$)$_2$ | CH(CH$_3$)$_2$ |
| 30 | OCH$_3$ | H | CH(CH$_3$)$_2$ | CH(CH$_2$OCH$_2$CH$_3$)$_2$ |
| 31 | OCH$_3$ | H | CH(CH$_3$)$_2$ | (CH$_2$CH$_2$O)$_2$CH$_3$ |
| 32 | OCH(CH$_3$)$_2$ | H | CH(CH$_3$)$_2$ | CH(CH$_2$OCH$_2$CH$_3$)$_2$ |
| 33 | OCH(CH$_3$)$_2$ | H | CH(CH$_3$)$_2$ | CH(CH$_3$)$_2$ |

TABLE 3

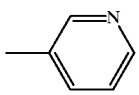

| Example | R³¹ (R³²) | R³² (R³¹) | R³⁴ |
|---|---|---|---|
| 8 | H | H | $C_6H_5$ |
| 9 | H | H | $(CH_2)_{10}CH_3$ |
| 10 | H | H | $(CH_2)_{14}CH_3$ |
| 11 | H | H | $(CH_2)_3Cl$ |
| 12 | H | H | $C_6H_4NH_2$-p |
| 13 | H | H | 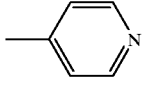 |
| 14 | H | H | 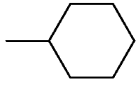 |
| 15 | H | $CH_3$ | $CH(CH_3)_2$ |
| 16 | H | H | $CH_2C_6H_4OCH_3$-p |
| 21 | H | H | $CH_3$ |
| 22 | H | H | $CH(CH_3)_2$ |
| 23 | H | H | $(CH_2)_2CH_3$ |
| 24 | H | H | $(CH_2)_2CO_2H$ |
| 25 | H | H | (cyclohexyl) |

Preparation Example 1 Preparation of Tablet

The compound of Example 20 (50.0 g), lactose (139.0 g), hydroxypropylcellulose (HPC-SL: 6.0 g), calcium carmellose (4.0 g), and purified water (9.0 g) were intimately mixed with one another. The mixture was granulated, dried, and subjected to granule size regulation. Magnesium stearate (1.0 g) was added to and intimately mixed with the granule, followed by tabletting to prepare tablets containing 50 mg of the compound, prepared in Example 20, per tablet.

Preparation Example 2 Preparation of Subtilized Granule

The compound of Example 20 (50.0 g), lactose (420 g), hydroxypropylcellulose (HPC-SL: 15 g), calcium carmellose (10 g), and purified water (30 g) were intimately mixed with one another. The mixture was granulated, dried, subjected to granule size regulation, and screened. Magnesium stearate (5.0 g) was added to and intimately mixed therewith to prepare subtilized granules containing 100 mg of the compound of Example 20 per g of the preparation.

Pharmacological Test Example

The compound of Synthesis Example 1, the compound of Example 7, and the compound of Example 20 were suspended or dissolved in a 0.5% aqueous methylcellulose solution. The resultant solutions were orally administered in an equimolar amount to dogs and rats. After the administration, the amount of each compound contained in plasma of each animal individual was quantitatively determined by HPLC. The results were as summarized in Table 5. The absorption in each specimen was assayed by the area under a medicament level of plasma vs time curve (AUC). As a result, AUCs obtained by the compounds of Examples 7 and 20 as prodrugs were 3 to 4 times higher for the dog and 3 to 7 times higher for the rat compared with the compound of Synthesis Example 1 as an activator body.

TABLE 4

| Example | R³¹ (R³²) | R³² (R³¹) | Q |
|---|---|---|---|
| 13c | H | H | Cl |
| 15c | H | $CH_3$ | Cl |
| 17 | H | H | $OCONH((CH_2)_2N(CH_3)_2)$ |
| 18 | H | H | $OPO(OCH_2CH_3)_2$ |
| 26 | $CH_2CH_3$ | $CH_2CH_3$ | $OCH_3$ |
| 27 | $(CH_2)_2CH_3$ | $(CH_2)_2CH_3$ | $OCH_2CH_3$ |
| 28 | H | H | $OCH_2CH_3$ |
| 29 | H | H | $OCH(CH_3)_2$ |

TABLE 5

| Compound | AUC Dog (μmol.hr/L) | AUC Rat (μmol.hr/L) |
| --- | --- | --- |
| Synthesis Example 1 | 0.3 ± 0.1 | 0.2 ± 0.1 |
| Example 7 | 0.9 ± 0.1 | 0.6 ± 0.1 |
| Example 20 | 1.2 ± 0.3 | 1.4 ± 0.1 |

Acute toxicity test by single administration

The compound of Example 20 was homogeneously suspended in a 0.5% aqueous methylcellulose solution. The suspension was forcibly orally administered to ICR male mice (5 weeks old). As a result, all the mice survived and developed no abnormality at a dose of 2 g/kg of the compound of Example 20.

What is claimed is:

1. A compound represented by formula (I) or a physiologically acceptable salt or solvate thereof:

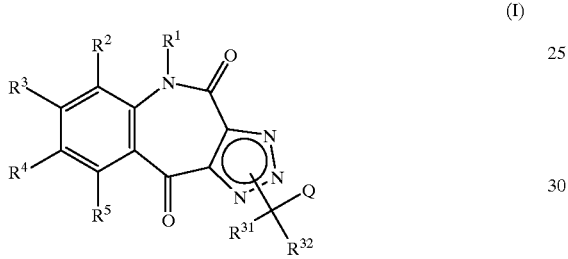

(I)

wherein $R^1$ represents a hydrogen atom, a hydroxyl group, $C_{1-4}$ alkyl, or phenyl $C_{1-4}$ alkyl;

$R^2$, $R^3$, $R^4$, and $R^5$, which may be the same or different, represent any one of the following (a) to (n):
(a) a hydrogen atom;
(b) a halogen atom;
(c) an optionally protected hydroxyl group;
(d) formyl;
(e) $C_{1-12}$ alkyl which may be substituted by a halogen atom;
(f) $C_{2-12}$ alkenyl which has one or more carbon—carbon double bonds and may be substituted by
  (1) a halogen atom,
  (2) cyano,
  (3) —$COR^9$ wherein $R^9$ represents a hydrogen atom or $C_{1-6}$ alkyl,
  (4) —$COOR^{10}$ wherein $R^{10}$ represents a hydrogen atom or $C_{1-6}$ alkyl,
  (5) —$CONR^{11}R^{12}$ wherein $R^{11}$ and $R^{12}$, which may be the same or different, represent
    (i) a hydrogen atom,
    (ii) $C_{1-6}$ alkyl which may be substituted by amino optionally substituted by $C_{1-4}$ alkyl, phenyl optionally substituted by $C_{1-4}$ alkyl which may be substituted by a saturated five- to seven-membered heterocyclic ring containing one or two nitrogen atoms (the nitrogen atoms may be substituted by $C_{1-4}$ alkyl), or a saturated or unsaturated five- to seven-membered heterocyclic ring,
    (iii) phenyl which may be substituted by carboxyl, or
    (iv) a saturated or unsaturated five to seven-membered heterocyclic ring,
  (6) a saturated or unsaturated five- to seven-membered heterocyclic ring which may be substituted by $C_{1-4}$ alkyl or may form a bicyclic ring fused with another ring;
(g) $C_{1-2}$ alkoxy which may be substituted by
  (1) a halogen atom,
  (2) a hydroxyl group,
  (3) cyano,
  (4) $C_{3-7}$ cycloalkyl,
  (5) phenyl,
  (6) $C_{1-4}$ alkoxy,
  (7) phenoxy,
  (8) amino which may be substituted by $C_{1-4}$ alkyl,
  (9) —$COR^{13}$ wherein $R^{13}$ represents a hydrogen atom, $C_{1-6}$ alkyl, phenyl optionally substituted by halogen or $C_{1-4}$ alkoxy, or phenyl $C_{1-4}$ alkyl,
  (10) —$COOR^{14}$ wherein $R^{14}$ represents a hydrogen atom or $C_{1-6}$ alkyl,
  (11) —$CONR^{15}R^{16}$ wherein $R^{15}$ and $R^{16}$, which may be the same or different, represent a hydrogen atom or $C_{1-6}$ alkyl which may be substituted by a saturated or unsaturated five- to seven-membered heterocyclic ring, or
  (12) a saturated or unsaturated five- to seven-membered heterocyclic ring which may be substituted by $C_{1-4}$ alkyl or phenyl $C_{1-4}$ alkyl;
(h) —C=N—$OR^{16a}$ wherein $R^{16a}$ represents a hydrogen atom, $C_{1-6}$ alkyl, phenyl $C_{1-4}$ alkyl, or phenyl;
(i) —$(CH_2)mOR^{17}$ wherein m is an integer of 0 to 4, and $R^{17}$ represents a hydrogen atom, $C_{1-6}$ alkyl, or phenyl $C_{1-4}$ alkyl of which one or more hydrogen atoms on the benzene ring may be substituted by $C_{1-4}$ alkyl;
(j) —$(CH_2)k$—$COR^{18}$ wherein k is an integer of 1 to 4, and $R^{18}$ represents a hydrogen atom or $C_{1-4}$ alkyl;
(k) —$(CH_2)j$—$COOR^{19}$ wherein j is an integer of 0 to 4, and $R^{19}$ represents a hydrogen atom or $C_{1-6}$ alkyl;
(l) —$(CH_2)p$-$NR^{20}R^{21}$ wherein p is an integer of 1 to 4, and $R^{20}$ and $R^{21}$, which may be the same or different, represent
  (1) a hydrogen atom,
  (2) $C_{1-6}$ alkyl which may be substituted by amino optionally substituted by $C_{1-4}$ alkyl,
  (3) phenyl $C_{1-4}$ alkyl,
  (4) —$COR^{22}$ wherein $R^{22}$ represents a hydrogen atom or $C_{1-4}$ alkyl which may be substituted by carboxyl, or
  (5) —$SO_2R^{23}$ wherein $R^{23}$ represents $C_{1-4}$ alkyl or phenyl which may be substituted by a halogen atom;
(m) —$(CH_2)q$—$CONR^{24}R^{25}$ wherein q is an integer of 0 to 4, and $R^{24}$ and $R^{25}$, which may be the same or different, represent a hydrogen atom, a saturated or unsaturated five- to seven-membered heterocyclic ring, or $C_{1-6}$ alkyl which may be substituted by a saturated or unsaturated five- to seven-membered heterocyclic ring, or alternatively $R^{24}$ and $R^{25}$ may form a saturated or unsaturated five- to seven-membered heterocyclic ring together with a nitrogen atom to which they are attached (the heterocyclic ring may further contain at least one oxygen, nitrogen, or sulfur atom, may form a bicyclic ring fused with another ring, or may be substituted by $C_{1-4}$ alkyl); and
(n) —$NR^{26}R^{27}$ wherein $R^{26}$ and $R^{27}$, which may be the same or different, represent a hydrogen atom or —COR$^{28}$ wherein R$^{28}$ represents a hydrogen atom, C$_{1-6}$ alkyl, or phenyl which may be substituted by C$_{1-4}$ alkyl or C$_{1-6}$ alkoxy optionally substituted by phenyl;

R$^{31}$ and R$^{32}$, which may be the same or different, represent a hydrogen atom or C$_{1-6}$ alkyl which may be substituted by a halogen atom; and Q represents a group selected from the following groups (i) to (iv) or a halogen atom or C$_{1-6}$ alkoxy:

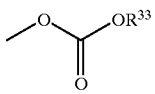

(i)

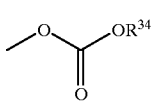

(ii)

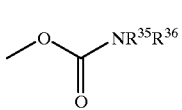

(iii)

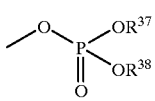

(iv)

wherein
R$^{33}$ represents
  C$_{1-6}$ alkyl which may be substituted by C$_{1-6}$ alkoxy optionally substituted by C$_{1-6}$ alkoxy, phenyl optionally substituted by C$_{1-6}$ alkoxy, amino, or nitro, or a saturated or unsaturated five- to seven-membered heterocyclic ring optionally substituted by C$_{1-6}$ alkoxy, amino, or nitro,
  phenyl which may be substituted by C$_{1-6}$ alkoxy, amino, or nitro, or
  a saturated or unsaturated five- to seven-membered heterocyclic ring which may be substituted by C$_{1-6}$ alkoxy, amino, or nitro, or
R$^{33}$ may form C$_{1-4}$ alkylene together with R$^{31}$ or R$^{32}$,
R$^{34}$ represents
  C$_{1-16}$ alkyl which may be substituted by a halogen atom, carboxyl, phenyl optionally substituted by C$_{1-6}$ alkoxy, amino, or nitro, or a saturated or unsaturated five- to seven-membered heterocyclic ring optionally substituted by C$_{1-6}$ alkoxy, amino, or nitro,
  phenyl which may be substituted by C$_{1-6}$ alkoxy, amino, or nitro, or
  a saturated or unsaturated five- to seven-membered heterocyclic ring which may be substituted by C$_{1-6}$ alkoxy, amino, or nitro,
R$^{35}$ and R$^{36}$, which may be the same or different, represent a hydrogen atom or C$_{1-6}$ alkyl which may be substituted by amino optionally substituted by C$_{1-4}$ alkyl or
R$^{35}$ and R$^{36}$ may form a saturated or unsaturated five- to seven-membered heterocyclic ring together with a nitrogen atom to which they are attached, and
R$^{37}$ and R$^{38}$, which may be the same or different, represent C$_{1-6}$ alkyl, provided that the group —CR$^{31}$R$^{32}$Q does not represent C$_{1-6}$ alkyl substituted by a halogen atom or C$_{1-6}$ alkoxy.

2. A compound according to claim 1, wherein R$^1$ represents a hydrogen atom and R$^2$, R$^3$, R$^4$, and R$^5$ represent a hydrogen atom or (g) C$_{1-12}$ alkoxy.

3. A compound according to claim 1, wherein R$^1$, R$^2$, and R$^5$ represent a hydrogen atom and R$^3$ and R$^4$ represent a hydrogen atom or (g) C$_{1-12}$ alkoxy.

4. A compound according to claim 1, wherein R$^1$, R$^2$, R$^4$, and R$^5$ represent a hydrogen atom and R$^3$ represents (g) C$_{1-12}$ alkoxy.

5. A compound according to claim 1, wherein R$^1$, R$^2$, R$^3$, and R$^5$ represent a hydrogen atom and R$^4$ represents (g) C$_{1-12}$ alkoxy.

6. A compound represented by formula (Ia) or a pharmacologically acceptable salt or solvate thereof:

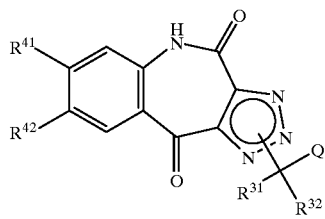

(Ia)

wherein R$^{41}$ and R$^{42}$, which may be the same or different, represent a hydrogen atom, optionally protected hydroxyl, C$_{1-6}$ alkoxy which may be substituted by a halogen atom, or C$_{1-6}$ alkyl which may be substituted by a halogen atom and R$^{31}$, R$^{32}$, and Q are as defined in claim 1, provided that the group —CR$^{31}$R$^{32}$Q does not represent C$_{1-6}$ alkyl substituted by a halogen atom or C$_{1-6}$ alkoxy.

7. A compound according to claim 6, wherein R$^{41}$ and R$^{42}$ represent C$_{1-6}$ alkoxy and Q represents group (i).

8. The compound according to claim 1, wherein the compound is selected from the group consisting of 2-(1-isopropoxycarbonyloxy-2-methylpropyl)-7,8-dimethoxy-4(5H), 10-dioxo-2H-1,2,3-triazolo[4,5-c][1]benzazepine, 2-(1-(1,3-diethoxy-2-propoxycarbonyloxy)-2-methylpropyl)-7,8-dimethoxy-4(5H), 10-dioxo-2H-1,2,3-triazolo[4,5-c][1]benzazepine, 2-(1-(1,3-diethoxy-2-propoxycarbonyloxy)-2-methylpropyl)-8-isopropoxy-7-methoxy-4(5H), 10-dioxo-2H- 1,2,3-triazolo[4,5-c][1]benzazepine, and 8-isopropoxy-2-(1-isopropoxycarbonyloxy-2-methylpropyl)-7-methoxy-4(5H), 10-dioxo-2H-1,2,3-triazolo[4,5-c][1]benzazepine, and salts thereof and solvates thereof.

9. A pharmaceutical composition comprising the compound according to any one of claims 1 to 8 or a pharmacologically acceptable salt or solvate thereof.

10. A method for the treatment of an allergic disease, comprising administering to mammals a therapeutically effective amount of the compound according to any one of claims 1 to 8 or a pharmacologically acceptable salt or solvate thereof together with a pharmaceutically acceptable carrier.

* * * * *